(12) United States Patent
Dahl et al.

(10) Patent No.: US 6,828,469 B2
(45) Date of Patent: Dec. 7, 2004

(54) COMPOSITIONS COMPRISING HEPTAMANTANE AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 383 days.

(21) Appl. No.: 10/012,334

(22) Filed: Dec. 12, 2001

(65) Prior Publication Data

US 2002/0143217 A1 Oct. 3, 2002

Related U.S. Application Data

(60) Provisional application No. 60/262,842, filed on Jan. 19, 2001, and provisional application No. 60/317,546, filed on Sep. 5, 2001.

(51) Int. Cl.[7] .............................. C07C 13/28; C07C 7/00
(52) U.S. Cl. ........................ 585/352; 585/16; 585/21; 585/800; 585/802; 585/803; 117/68; 117/69; 117/70
(58) Field of Search ........................ 585/803, 21, 16, 585/800, 352, 802; 117/68, 69, 70

(56) References Cited

U.S. PATENT DOCUMENTS

| 3,457,318 A | | 7/1969 | Capaldi |
| 3,832,332 A | | 8/1974 | Thompson |
| 4,952,748 A | | 8/1990 | Alexander |
| 4,952,749 A | | 8/1990 | Alexander |
| 4,952,757 A | | 8/1990 | Purcell et al. |
| 4,982,049 A | | 1/1991 | Alexander |
| 5,017,734 A | | 5/1991 | Baum |
| 5,019,665 A | | 5/1991 | Partridge |
| 5,126,274 A | * | 6/1992 | McIver et al. ............... 436/140 |
| 5,245,104 A | | 9/1993 | Cullick |
| 5,268,513 A | | 12/1993 | Shen |
| 5,298,666 A | | 3/1994 | Shen |
| 5,306,851 A | | 4/1994 | Wu |
| 5,334,228 A | * | 8/1994 | Ashjian et al. ............... 44/347 |
| 5,347,063 A | | 9/1994 | Shen |
| 5,369,213 A | | 11/1994 | Shen |
| 5,380,947 A | | 1/1995 | Chen |
| 5,382,684 A | | 1/1995 | Moini |

(List continued on next page.)

FOREIGN PATENT DOCUMENTS

| EP | 0399851 | 11/1996 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).

Balaban, et al., Systemic Classification and Nomenclature of Diamond Hydrocarbons–I, *Tetrahedron*, 34, pp. 3599–3606, (1978), no month.

Badziag, P., et al., "Nanometre–sized Diamonds are More Stable than Graphite", *Nature*, vol. 343, pp. 244–245, and 517 (Jan. 1990).

(List continued on next page.)

*Primary Examiner*—Elizabeth D. Wood
(74) *Attorney, Agent, or Firm*—Burns Doane Swecker & Mathis, LLP

(57) ABSTRACT

Disclosed are compositions comprising one or more heptamantanes. Specifically disclosed are compositions comprising 25 to 100 weight percent of one or more heptamantanes. Also disclosed are novel processes for the separation and isolation of heptamantane components into recoverable fractions from a feedstock containing at least a higher diamondoid component which contains one or more heptamantane components.

41 Claims, 120 Drawing Sheets

U.S. PATENT DOCUMENTS

| | | | |
|---|---|---|---|
| 5,397,488 | A | | 3/1995 | Chen |
| 5,410,092 | A | | 4/1995 | Shen |
| 5,414,189 | A | * | 5/1995 | Chen et al. ................. 585/801 |
| 5,430,193 | A | | 7/1995 | Shen |
| 5,461,184 | A | | 10/1995 | Swanson |
| 5,498,812 | A | | 3/1996 | Bradway |
| 5,576,355 | A | | 11/1996 | Chen |
| 6,235,851 | B1 | | 5/2001 | Ishii |

OTHER PUBLICATIONS

Bagrii, Ye, et al., "Catalytic Breakdown of Paraffinic Hydrocarbons in the Presence of Adamantanes", *Petrol. Chem USSR*, vol. 30, No. 2, pp. 131–134, (1990), no month.

Chung, et al., Recent Development in High–Energy Density Liquid Fuels, *Energy and Fuels, 13*, pp. 641–649, (1999), no month.

Dahl, J., et al., Diamondoid Hydrocarbons as Indicators of Natural Oil Cracking, *Nature, 399*, pp. 54–57 (1999), no month.

Drexler, Eric K., *Nanosystems: Molecular Machinery Manfacturing and Computation*, John Wiley & Sons, pp. 238–249, (1992), no month.

Fort, Jr., et al., Adamantane: Consequences of the Diamondoid Structure, *Chem. Rev., 64*, pp. 277–300, (1964), no month.

Hala, V.S., et al., "Analyse Unds erwendung on Pyrolyseol", *Jahrgang*, pp. 85–87, (Feb. 1997) In German–English Abstract on p. 85, considered to extent of abstract.

Landa, S., " Adamantane and Its Homologues", *Current Science*, Gangalore, India, Vo. 32, pp. 485–489 (1963), no month.

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel, 74*:10, pp. 1512–1521 (1995), no month.

McKervey, Synthetic Approaches to Large Diamondoid Hydrocarbonds, *Tetrahedron, 36*, pp. 971–992, (1980), no month.

Machacek, V., et al., "Let Od Objeveni Adamantanu", *Chemicke Listy/svazek*, pp. 753–761, (1982) Russian—English Abstract on p. 761, considered to extent of abstract no month.

Oya, A, et al., "Carbonization of Adamantanes to a Graphitizable Carbon", *Fuel*, vol. 60, pp. 667–669, (Aug. 1981).

Petrov, A., "Hydrocarbons of Adamantane Series as Indicies of Petroleum Catagensis Process", *Advances in Organic Geo Chemistry*, 6th International Meeting on Organic Geochemistry, pp. 517–522 (1973), no month.

Prusova, D., Liquid Chromatography of Adamantanes and Carbon Adsorbents, *J. Chrom*, 234, pp. 1–11, (1982), no month.

Rollman, L., et al., "Admantanes From Petroleum, with Zeolites", American Chemical Study, 210th ACS National Meeting, Abstract and paper, Aug. 20, 1995.

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2.18}.-O^{3.16}.O^{4.13}.O^{5.10}.O^{6.14}.O^{7.11}.O^{15.20}$]–Doco- sane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*vol. 114, No. 2, pp 497–505, (1992), no month.

Supryadkina, NY, et al., "Catalytic Dealkylation of Alkyladamantanes", *Petrol. Chem., USSR*, vol. 28, No. 2, pp. 103–110, (1988), no month.

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom.*, 270, pp. 199–205, (1983), no month.

Wingert, W., "G.C.–m.s. Analysis of Diamondoid Hydrocarbons in Smackover Petroleums", *Fuel*, vol. 71, pp. 37–42, (Jan. 1992).

* cited by examiner

Symmetrical
Heptamantanes

Enantiomeric
Heptamantanes

* Mirror plane indicating enantiomeric pair of pentamantanes

A) Peaks Cut and Sent to Column #2

Cut 3 Heptamantane 1

Cut 5 Heptamantane 2

Gerstel Column #1

B) Peaks Sent to Traps
Where Crystals of Heptamantane #1 (trap 2) and #2 (trap 4) formed Gerstel Column #2

Heptamantane 1

Heptamantane 2

A)

B)

A)

B)

Heptamantane #1 Crystals

Heptamantane #2
Crystals

A) Parr Reaction No. 5, Product from FSL 8691, Fraction #7 — Heptamantanes

GC Time (min.) →

B) Starting Material FSL 8691, Fraction #7

GC Time (min.) →

FIG. 15

| | 394 Heptamantanes | | | | | | 448 Heptamantane | | | | | | | |
|---|---|---|---|---|---|---|---|---|---|---|---|---|---|---|
| ODS HPLC Fraction # | 1 | 2 | 3 | 4 | 5 | 6 | 7 | 8 | 9 | 10 | 11 | 12 | 13 | 14 |
| | 15.07 | 15.63 | 17.40 | 17.42 | 17.78 | 17.86 | 17.89 | 18.05 | 18.20 | 18.22 | 18.26 | 18.28 | 18.35 | 18.37 |
| 40 | | | | | | | | | | | | | | |
| 41 | | 15.63 | | | | | | | | | | | | |
| 42 | | | | | | | | | | | | | | |
| 43 | | | | | | | | | | | | | | |
| 44 | | | | | | | | | | | | | | |
| 45 | 15.07 | | | | | | | | | | | | | |
| 46 | x | | | | | | | | | | | | | |
| 47 | | | | | | | | | | | | | | |
| 48 | | | | | | | | | | | | | | |
| 56 | | | | | | | | | | | | | | |
| 57 | | | | | | | | 18.01 | | | | | 18.33 | |
| 58 | | | | | | | | | | | | | x | |
| 59 | | | | | | | | x | 18.13 | | | | | |
| 60 | | | 17.38 | | | | | | x | | | | | |
| 61 | | | x | | | | | | 18.16 | | | | | |
| 62 | | | | | | | | | x | | | | | |
| 63 | | | | | | | | | | | | | | |
| 64 | | | | | 17.83 | | | | | | | | | |
| 65 | | | | 17.52 | | | | | | | | | | |
| 66 | | | | | | | | | | | | | | |
| 67 | | | | x | x | | | | | | | | | |
| 68 | | | | | | | | | | | | | | |
| 69 | | | | | | | | | | | | | | 18.35 |
| 70 | | | | | | | | | | | | | | x |
| 71 | | | | | | | | | | | | | | |
| 72 | | | | | | | | | | | | | | |
| 73 | | | | | | | | | | | | | 18.32 | |
| 74 | | | | | | | | | | | | | x | |
| 75 | | | | | 17.73 | | | | | | | | | |
| 76 | | | | | x | | | | 18.16 | | | | | |
| 77 | | | | | | | | | x | | | | | |
| 78 | | | | | | | | | | | | | | |
| 79 | | | | | | | | | | | | | | |
| 80 | | | | | | | | | | | | | | |
| 81 | | | | | | | | | | | | | | |
| 82 | | | | | | | | | | | | | | |
| 83 | | | | | | | | | | | | | | |
| 84 | | | | | | | | | | | | | | |
| 85 | | | | | | | | | | 18.22 | | | | |
| 86 | | | | | | | | | | x | | | | |
| 87 | | | | | | | | | | | | | | |
| 88 | | | | | | | | | | | | | | |
| 89 | | | | | 17.59 | | | | | | | | | |
| 90 | | | | | x | | | | | | | | x | |
| 91 | | | | | | | | | | | | | 18.32 | |
| 92 | | | | | | | | | | | | | | |
| 93 | | | | | | | | | | | | | | |
| 94 | | | | | | | | | | | | | | |
| 95 | | | | | | | | | | | | | | |
| 96 | | | | | | | | | | | | | | |
| 97 | | | | | | | | | | | | | | |
| 98 | | | | | | | | | | | | | | |
| 99 | | | | | | | | | | | | | | |
| 100 | | | | | | | | | | | | | | |

Numbers in cells are the individual heptamantane retention times in minutes in our GC/MS assay.

A)

B)

A)

B)

A)

B)

A)

B)

A)

B)

A)

B)

A)

B)

A)

B)

Name: [121321] Heptamantane
Formula: $C_{30}H_{34}$
Molecular Weight: 394.602
Molecular Weight (Exact): 394.2660513
Symmetry: $C_S$ Carbon Framework CPK Representation

[121321] Heptamantane
View into Specified Diamond Crystal Lattice Plane 111 110 100

Name: [123124] Heptamantane
Formula: $C_{30}H_{34}$
Molecular Weight: 394.602
Molecular Weight (Exact): 394.2660513
Symmetry: $C_S$ Carbon Framework CPK Representation

[123124] Heptamantane
View into Specified Diamond Crystal Lattice Plane

[123(4)21] Heptamantane
and its enantiomer

Formula: $C_{34}H_{40}$
Molecular Weight: 448.694
Molecular Weight (Exact): 448.3130015

Carbon Framework

CPK Representation

[123(4)21] Heptamantane
and its enantiomer
View into Specified Diamond Crystal Lattice Plane 111      110      100

[123(2)41] Heptamantane
and its enantiomer

Formula: $C_{34}H_{40}$
Molecular Weight 448.694
Molecular Weight (Exact) 448.3130015

Carbon Framework

CPK Representation

[123(2)41] Heptamantane
and its enantiomer
View into Specified Diamond Crystal Lattice Plane

[121342] Heptamantane

Formula: $C_{34}H_{40}$
Molecular Weight 448.694
Molecular Weight (Exact) 448.3130015

[121342] Heptamantane
View into Specified Diamond Crystal Lattice Plane 111  110  100

Name: [121212] Heptamantane
Formula: $C_{34}H_{40}$
Molecular Weight: 448.694
Molecular Weight (Exact): 448.313015
Symmetry: $C_{2v}$ Carbon Framework CPK Representation

[121212] Heptamantane
View into Specified Diamond Crystal Lattice Plane
111    110    100

[1212(3)4] Heptamantane

Formula: $C_{34}H_{40}$
Molecular Weight 448.694
Molecular Weight (Exact) 448.3130015

Carbon Framework

CPK Representation

[1212(3)4] Heptamantane
View into Specified Diamond Crystal Lattice Plane 111  110  100

[121(23)4] Heptamantane

Formula: $C_{34}H_{40}$
Molecular Weight 448.694
Molecular Weight (Exact) 448.3130015

Carbon Framework

CPK Representation

[121(23)4] Heptamantane
View into Specified Diamond Crystal Lattice Plane

[12(34)12] Heptamantane

Formula: $C_{34}H_{40}$
Molecular Weight 448.694
Molecular Weight (Exact) 448.313015

Carbon Framework

CPK Representation

[12(34)12] Heptamantane
View into Specified Diamond Crystal Lattice Plane

[12(12)34] Heptamantane

Formula: $C_{34}H_{40}$
Molecular Weight: 448.694
Molecular Weight (Exact): 448.3130015

Carbon Framework

CPK Representation

[12(12)34] Heptamantane
View into Specified Diamond Crystal Lattice Plane

[1(2)3(1,2)4] Heptamantane
and its enantiomer

Formula: $C_{34}H_{40}$
Molecular Weight: 448.694
Molecular Weight (Exact): 448.3130015

Carbon Framework

CPK Representation and its enantiomer
[1(2)3(1,2)4] Heptamantane
View into Specified Diamond Crystal Lattice Plane

[121(2)34] Heptamantane
and its enantiomer

Formula: $C_{34}H_{40}$
Molecular Weight 448.694
Molecular Weight (Exact) 448.3130015

Carbon Framework

CPK Representation

[121(2)34] Heptamantane
and its enantiomer

View into Specified Diamond Crystal Lattice Plane

[121(3)23] Heptamantane
and its enantiomer

Formula: $C_{34}H_{40}$
Molecular Weight: 448.694
Molecular Weight (Exact): 448.3130015

Carbon Framework

CPK Representation

[121(3)23] Heptamantane
and its enantiomer
View into Specified Diamond Crystal Lattice Plane

[121(3)24] Heptamantane
and its enantiomer

Formula: $C_{34}H_{40}$
Molecular Weight: 448.694
Molecular Weight (Exact): 448.3130015

Carbon Framework

CPK Representation

[121(3)24] Heptamantane
and its enantiomer
View into Specified Diamond Crystal Lattice Plane

[121(3)41] Heptamantane
and its enantiomer

Formula: $C_{34}H_{40}$
Molecular Weight: 448.694
Molecular Weight (Exact): 448.3130015

Carbon
Framework

CPK
Representation

[121(3)41] Heptamantane
and its enantiomer
View into Specified Diamond Crystal Lattice Plane

[121(3)43] Heptamantane
and its enantiomer

Formula: $C_{34}H_{40}$
Molecular Weight 448.694
Molecular Weight (Exact) 448.313015

Carbon Framework

CPK Representation and its enantiomer
[121(3)43] Heptamantane
View into Specified Diamond Crystal Lattice Plane

[121(3)21] Heptamantane
and its enantiomer

Formula: $C_{32}H_{40}$
Molecular Weight: 448.694
Molecular Weight (Exact): 448.3130015

Carbon Framework

CPK Representation

[121(3)21] Heptamantane
and its enantiomer
View into Specified Diamond Crystal Lattice Plane 111　　　110　　　100

[121213] Heptamantane
and its enantiomer

Formula: $C_{34}H_{40}$
Molecular Weight  448.694
Molecular Weight (Exact)  448.3130015

Carbon Framework

CPK Representation

[121213] Heptamantane
and its enantiomer
View into Specified Diamond Crystal Lattice Plane

[121232]A Heptamantane
and its enantiomer

Formula: $C_{34}H_{40}$
Molecular Weight: 448.694
Molecular Weight (Exact): 448.3130015

Carbon Framework

CPK Representation

[121213] Heptamantane
and its enantiomer
View into Specified Diamond Crystal Lattice Plane

[121234] Heptamantane
and its enantiomer

Formula: $C_{34}H_{40}$
Molecular Weight 448.694
Molecular Weight (Exact) 448.3130015

Carbon Framework

CPK Representation

[121234] Heptamantane
and its enantiomer
View into Specified Diamond Crystal Lattice Plane 111 110 100

[1213(1)4] Heptamantane
and its enantiomer

Formula: $C_{34}H_{40}$
Molecular Weight  448.694
Molecular Weight (Exact)  448.3130015

Carbon Framework

CPK Representation

[1213(1)4] Heptamantane
and its enantiomer
View into Specified Diamond Crystal Lattice Plane

[121312] Heptamantane
and its enantiomer

Formula: $C_{34}H_{40}$
Molecular Weight: 448.694
Molecular Weight (Exact): 448.3130015

Carbon Framework

CPK Representation

[121312] Heptamantane
and its enantiomer
View into Specified Diamond Crystal Lattice Plane

[121314] Heptamantane
and its enantiomer

Formula: $C_{34}H_{40}$
Molecular Weight: 448.694
Molecular Weight (Exact): 448.3130015

Carbon Framework

CPK Representation

[121314] Heptamantane and its enantiomer
View into Specified Diamond Crystal Lattice Plane 111   110   100

[121343] Heptamantane
and its enantiomer

Formula: $C_{34}H_{40}$
Molecular Weight: 448.694
Molecular Weight (Exact): 448.3130015

Carbon Framework

CPK Representation

[121343] Heptamantane
and its enantiomer
View into Specified Diamond Crystal Lattice Plane 111 110 100

[1232(1)4] Heptamantane
and its enantiomer

Formula: $C_{32}H_{40}$
Molecular Weight 448.694
Molecular Weight (Exact) 448.3130015

Carbon Framework

CPK Representation and its enantiomer
[1232(1)4] Heptamantane
View into Specified Diamond Crystal Lattice Plane

[123214] Heptamantane
and its enantiomer

Formula: $C_{34}H_{40}$
Molecular Weight 448.694
Molecular Weight (Exact) 448.3130015

Carbon Framework

CPK Representation

[123214] Heptamantane and its enantiomer
View into Specified Diamond Crystal Lattice Plane 111  110  100

[123231] Heptamantane
and its enantiomer

Formula: $C_{34}H_{40}$
Molecular Weight 448.694
Molecular Weight (Exact) 448.3130015

Carbon Framework

CPK Representation

[123231] Heptamantane
and its enantiomer
View into Specified Diamond Crystal Lattice Plane

[123234] Heptamantane
and its enantiomer

Formula: $C_{34}H_{40}$
Molecular Weight: 448.694
Molecular Weight (Exact): 448.3130015

Carbon Framework

CPK Representation

[123234] Heptamantane
and its enantiomer
View into Specified Diamond Crystal Lattice Plane

[123241] Heptamantane
and its enantiomer

Formula: $C_{32}H_{40}$
Molecular Weight 448.694
Molecular Weight (Exact) 448.3130015

Carbon Framework

CPK Representation

[123241] Heptamantane
and its enantiomer
View into Specified Diamond Crystal Lattice Plane 111   110   100

[1(2)3(1)24] Heptamantane
and its enantiomer

Formula: $C_{34}H_{40}$
Molecular Weight 448.694
Molecular Weight (Exact) 448.3130015

Carbon Framework

CPK Representation

[1(2)3(1)24] Heptamantane
and its enantiomer
View into Specified Diamond Crystal Lattice Plane

[1(2)31(3)4] Heptamantane
and its enantiomer

Formula: $C_{34}H_{36}$
Molecular Weight 448.694
Molecular Weight (Exact) 448.3130015

Carbon Framework

CPK Representation and its enantiomer
[1(2)31(3)4] Heptamantane
View into Specified Diamond Crystal Lattice Plane

[1(2)3132] Heptamantane
and its enantiomer

Formula: $C_{34}H_{40}$
Molecular Weight: 448.694
Molecular Weight (Exact): 448.3130015

Carbon Framework

CPK Representation

[1(2)3132] Heptamantane
and its enantiomer
View into Specified Diamond Crystal Lattice Plane

[1(2)3134] Heptamantane
and its enantiomer

Formula: $C_{34}H_{40}$
Molecular Weight 448.694
Molecular Weight (Exact) 448.3130015

Carbon Framework

CPK Representation and its enantiomer
[1(2)3134] Heptamantane
View into Specified Diamond Crystal Lattice Plane

[1(2)3142] Heptamantane
and its enantiomer

Formula: $C_{34}H_{40}$
Molecular Weight 448.694
Molecular Weight (Exact) 448.3130015

Carbon Framework

CPK Representation and its enantiomer
[1(2)3142] Heptamantane
View into Specified Diamond Crystal Lattice Plane

[12(1)3(2)4] Heptamantane
and its enantiomer

Formula: $C_{34}H_{40}$
Molecular Weight: 448.694
Molecular Weight (Exact): 448.3130015

Carbon Framework

CPK Representation

[12(1)3(2)4] Heptamantane
and its enantiomer
View into Specified Diamond Crystal Lattice Plane

[12(1)324] Heptamantane
and its enantiomer

Formula: $C_{34}H_{40}$
Molecular Weight: 448.694
Molecular Weight (Exact): 448.3130015

Carbon Framework

CPK Representation

[12(1)324] Heptamantane and its enantiomer

View into Specified Diamond Crystal Lattice Plane 111  110  100

[12(1,3)42] Heptamantane
and its enantiomers

Formula: $C_{34}H_{40}$
Molecular Weight: 448.694
Molecular Weight (Exact): 448.3130015

Carbon Framework

CPK Representation and its enantiomer
[12(1,3)42] Heptamantane
View into Specified Diamond Crystal Lattice Plane

[12(1,3)43] Heptamantane
and its enantiomers

Formula: $C_{34}H_{40}$
Molecular Weight: 448.694
Molecular Weight (Exact): 448.313015

Carbon Framework

CPK Representation

[12(1,3)43] Heptamantane
and its enantiomer
View into Specified Diamond Crystal Lattice Plane

[12(13)32] Heptamantane
and its enantiomer

Formula: $C_{34}H_{40}$
Molecular Weight: 448.694
Molecular Weight (Exact): 448.3130015

Carbon Framework

CPK Representation

[12(13)32] Heptamantane and its enantiomer

View into Specified Diamond Crystal Lattice Plane 111  110  100

[12(13)34] Heptamantane
and its enantiomer

Formula: $C_{34}H_{40}$
Molecular Weight 448.694
Molecular Weight (Exact) 448.3130015

Carbon Framework

CPK Representation

[12(13)34] Heptamantane and its enantiomer

View into Specified Diamond Crystal Lattice Plane

[12(3)1(2)3] Heptamantane
and its enantiomers

Formula: $C_{34}H_{40}$
Molecular Weight 448.694
Molecular Weight (Exact) 448.3130015

Carbon Framework

CPK Representation and its enantiomer
[12(3)1(2)3] Heptamantane
View into Specified Diamond Crystal Lattice Plane 111        110        100

[12(3)1(2)4] Heptamantane
and its enantiomer

Formula: $C_{34}H_{40}$
Molecular Weight: 448.694
Molecular Weight (Exact): 448.3130015

Carbon Framework

CPK Representation and its enantiomer
[12(3)1(2)4] Heptamantane
View into Specified Diamond Crystal Lattice Plane

[12(3)1(3)4] Heptamantane
and its enantiomer

Formula: $C_{34}H_{40}$
Molecular Weight 448.694
Molecular Weight (Exact) 448.3130015

Carbon Framework

CPK Representation and its enantiomer
[12(3)1(3)4] Heptamantane
View into Specified Diamond Crystal Lattice Plane

[12(3)124] Heptamantane
and its enantiomer

Formula: $C_{34}H_{40}$
Molecular Weight: 448.694
Molecular Weight (Exact): 448.3130015

Carbon Framework

CPK Representation and its enantiomer
[12(3)124] Heptamantane
View into Specified Diamond Crystal Lattice Plane

[12(3)134] Heptamantane
and its enantiomer

Formula: $C_{34}H_{40}$
Molecular Weight: 448.694
Molecular Weight (Exact): 448.3130015

Carbon Framework

CPK Representation and its enantiomer

[12(3)134] Heptamantane
View into Specified Diamond Crystal Lattice Plane

[123412] Heptamantane
Formula: $C_{34}H_{40}$
Molecular Weight 448.694
Molecular Weight (Exact) 448.3130015

Carbon Framework

CPK Representation

[123412] Heptamantane
View into Specified Diamond Crystal Lattice Plane 111  110  100

[1212(1)3] Heptamantane
Formula: $C_{34}H_{40}$
Molecular Weight 448.694
Molecular Weight (Exact) 448.3130015

Carbon Framework

CPK Representation

[1212(1)3] Heptamantane
View into Specified Diamond Crystal Lattice Plane 111 110 100

[121(2)31] Heptamantane
Formula: $C_{34}H_{40}$
Molecular Weight 448.694
Molecular Weight (Exact) 448.3130015

Carbon Framework

CPK Representation

[121(2)31] Heptamantane
View into Specified Diamond Crystal Lattice Plane 111                110                100

COMPOSITIONS COMPRISING HEPTAMANTANE AND PROCESSES FOR THEIR SEPARATION

REFERENCE TO RELATED APPLICATIONS

This application claims priority under 35 USC §119(e) to U.S. Provisional Application Ser. No. 60/262,842 filed Jan. 19, 2001 and to U.S. Provisional Application Ser. No. 60/317,546 filed Sep. 5, 2001, both of which are incorporated by reference.

BACKGROUND OF THE INVENTION

Field of the Invention

This invention is directed to novel compositions comprising one or more heptamantanes. This invention is also directed to novel processes for the separation and isolation of heptamantane components into recoverable fractions from a feedstock containing at least one or more heptamantane components.

References

The following publications and patents are cited in this application as superscript numbers:

[1] Lin, et al., *Natural Occurrence of Tetramantane* ($C_{22}H_{28}$), *Pentamantane* ($C_{26}H_{32}$) *and Hexamantane* ($C_{30}H_{36}$) *in a Deep Petroleum Reservoir*, Fuel, 74(10):1512-1521 (1995)

[2] Alexander, et al., *Purification of Hydrocarbonaceous Fractions*, U.S. Pat. No. 4,952,748, issued Aug. 28, 1990

[3] McKervey, Synthetic *Approaches to Large Diamondoid Hydrocarbons*, Tetrahedron, 36:971-992 (1980).

[4] Wu, et al., *High Viscosity Index Lubricant Fluid*, U.S. Pat. No. 5,306,851, issued Apr. 26, 1994.

[5] Chung et al., *Recent Development in High-Energy Density Liquid Fuels*, Energy and Fuels, 13, 641-649 (1999).

[6] Sandia National Laboratories (2000), *World's First Diamond Micromachines Created at Sandia*, Press Release, (Feb. 22, 2000) www.Sandia.gov.

[7] Balaban et al., *Systematic Classification and Nomenclature of Diamondoid Hydrocarbons*—I, Tetrahedron. 34, 3599-3606 (1978).

[8] Chen, et al., *Isolation of High Purity Diamondoid Fractions and Components*, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

State of the Art

Heptamantanes are bridged-ring cycloalkanes. They are the face-fused heptamers of adamantane (tricyclo[3.3.1.1$^{3,7}$]decane). The compounds have a "diamondoid" topology, which means their carbon atom arrangement is superimposable on a fragment of the diamond lattice (FIG. 1). Heptamantanes possess seven of the "diamond crystal units" and therefore, it is postulated that there are one hundred sixty possible heptamantane structures. Among them, 85 of the one hundred sixty have the molecular formula $C_{34}H_{40}$ (molecular weight 448) and of these, 7 are symmetrical, having no enantiomers. Six have the molecular formula $C_{32}H_{36}$ (molecular weight 420) and 67 have the molecular formula $C_{33}H_{38}$ (molecular weight 434). There are two fully condensed heptamantanes having the molecular formula $C_{30}H_{34}$ (molecular weight 394).

Little or no published work is available for heptamantanes and higher molecular weight diamondoids. Heptamantane compounds have not been artificially synthesized or isolated and these compounds have been recently thought only to have a theoretical existence.[7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding practical applications of higher diamondoids and even less, if any information regarding heptamantanes. This fact is probably due to extreme difficulties encountered in their isolation and due to failed synthesis attempts. Lin and Wilk, for example, discuss the possible presence of pentamantanes in a gas condensate and further postulate that hexamantane may also be present.[1] The researchers postulate the existence of the compounds solely based on a mass spectrometric fragmentation pattern. They did not, however, report the isolation of a single pentamantane, hexamantane nor mention heptamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement routes employing Lewis acid catalysts, useful in synthesizing triamantane and lower diamondoids have been unsuccessful to synthesize other tetramantanes or pentamantanes. No attempt to synthesize or isolate heptamantanes has been reported.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

In addition, based on theoretical considerations, the heptamantanes have sizes in the nanometer range and, in view of the properties noted above, the inventors contemplate that such compounds would have utility in micro- and molecular-electronics and nanotechnology applications. In particular, the rigidity, strength, stability, variety of structural forms and multiple attachment sites shown by these molecules makes possible accurate construction of robust, durable, precision devices with nanometer dimensions. The various heptamantanes are three-dimensional nanometer sized units showing different diamond lattice arrangements. This translates into a variety of rigid shapes and sizes for the one hundred sixty heptamantanes. For example, [121212] heptamantane is rod shaped, [12(3,4)12] heptamantane has a cross-shaped structure while [121234] is "L" shaped and

[12132] is disc-shaped with one lobe. The two enantiomers of [121312] have left and right handed screw like structures. A variety of other shapes exist among the heptamantanes which may serve in applications which depend upon specific geometries. It has been estimated that MicroElectroMechanical Systems (MEMs) constructed out of diamond should last 10,000 times longer then current polysilicon MEMs, and diamond is chemically benign and would not promote allergic reactions in biomedical applications.[6] Again, the inventors contemplate that the various heptamantanes would have similar attractive properties. Furthermore, most of the heptamantanes (molecular weight 448 as well as the partially condensed 420 and 434) possess chirality, offering opportunities for making nanotechnology objects of great structural specificity and ones which have useful optical properties. Applications of these heptamantanes include molecular electronics, photonic devices, nanomechanical devices, and nanostructured polymers and other materials.

Notwithstanding these advantages of heptamantanes, the art, as noted above, fails to provide for compositions comprising heptamantanes or for processes that would lead to these compositions. In view of the above, there is an ongoing need in the art to provide for compositions comprising one or more heptamantanes.

SUMMARY OF THE INVENTION

This invention is directed to novel compositions comprising one or more heptamantane components.

Accordingly, in one of its composition aspects, this invention is directed to a composition comprising one or more heptamantane components wherein said composition comprises at least about 25 weight percent heptamantane components based on the total weight of the diamondoids in the composition.

In another of its composition aspects, the compositions preferably comprise one or more heptamantane components wherein the heptamantane components make up from about 50 to 100 weight percent, preferably about 70 to 100 weight percent, more preferably about 90 to 100 weight percent and even more preferably about 95 to 100 weight percent of the total weight of the diamondoids in the compositions.

In another of its composition aspects, the compositions comprise at least about 10 weight percent and preferably at least about 20 weight percent of heptamantanes based on the total weight of the composition. Other compositions of this invention contain from 50 to 100 weight percent, 70 to 100 weight percent, 95 to 100 weight percent and 99 to 100 weight percent of heptamantanes based on the total weight of the composition.

In another of its composition aspects, the compositions preferably comprise from about 70 to 100 weight percent, more preferably from about 90 to 100 weight percent, even more preferably from about 95 to 100 weight percent and most preferably from about 99 to 100 weight percent of a single heptamantane component, including isolated optical isomers thereof, based on the total weight of the composition.

Compositions are sufficiently enriched in heptamantane components the heptamantanes can form crystal structures. Accordingly, another aspect of this invention is directed to a composition comprising a heptamantane crystal. Since such heptamantane can co-crystallize, another aspect of this invention is directed to the co-crystals comprising crystals of at least two heptamantane components or a heptamantane component and another higher diamondoid component.

This invention is also directed to novel processes for the separation and isolation of heptamantane components into recoverable fractions from a feedstock containing one or more heptamantane components and nonheptamantane materials. These processes for recovering a composition enriched in heptamantane components entail removing at least a portion of the nonheptamantane materials which have a boiling point below the lowest boiling heptamantane component and utilizing a subsequent separation technique to recover heptamantane components from the resulting residue. Accordingly, this aspect is directed to processes which comprise:

a) selecting a feedstock comprising recoverable amounts of heptamantane components and nonheptamantane materials;

b) removing from the feedstock a sufficient amount of nonheptamantane materials that have boiling points below the boiling point of the lowest boiling point heptamantane component in the feedstock under conditions to form a treated feedstock enriched in heptamantane components which can be recovered;

c) recovering heptamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the heptamantane components in the treated feedstock can be thermally treated to pyrolyze at least a sufficient amount of non-diamondoid components therefrom under conditions to provide a thermally treated feedstock retaining recoverable amounts of heptamantane. Such a pyrolization step prior to step c) is useful for thermally degrading at least a portion of any materials remaining in the treated feedstock having a thermal stability lower than the heptamantane components in common hydrocarbonaceous feedstocks. This pyrolysis step can be carried out in step b) if desired.

In a preferred embodiment of this invention, directed to the chromatographic techniques, is employing high performance liquid chromatography using one or more columns, more preferably reverse phase. A more preferred method, is using columns exhibiting a different selectivity to the heptamantane components slated for enrichment. Alternatively, high performance liquid chromatography can be coupled with gas chromatography, such as preparative gas chromatography to further facilitate isolations.

BRIEF DESCRIPTION OF THE DRAWINGS

FIG. 7A, shows the first column cuts containing two of the heptamantanes from Feedstock B.

FIG. 7B, shows the second column peaks isolated and sent to the traps. From this procedure pure heptamantane components were isolated (FIGS. 8 and 9), heptamantane #1, the first heptamantane to elute in our GC/MS assay, and heptamantane #2 which is the second to elute.

FIG. 14B illustrates the GC of Feedstock B atmospheric distillation fraction #6, exemplified in Example 1, which was used as feedstock in pyrolytic processing.

FIG. 14A illustrates the GC of the product of the pyrolytic process.

FIG. 15 illustrates results of a preparative HPLC separation of Feedstock B distillate cut #7 pyrolysis product saturated hydrocarbon fraction showing HPLC fractions taken using octadecyl silane "ODS" columns and acetone mobile phase. Heptamantanes are numbered in order of their elution order on our GC/MS assay, and typical GC/MS retention times are listed.

DETAILED DESCRIPTION OF THE INVENTION

This invention is directed to compositions comprising one or more heptamantane components. However, prior to describing this invention in further detail, the following terms will first be defined.

Definitions

As used herein, the following terms have the following meanings.

Figure 1:
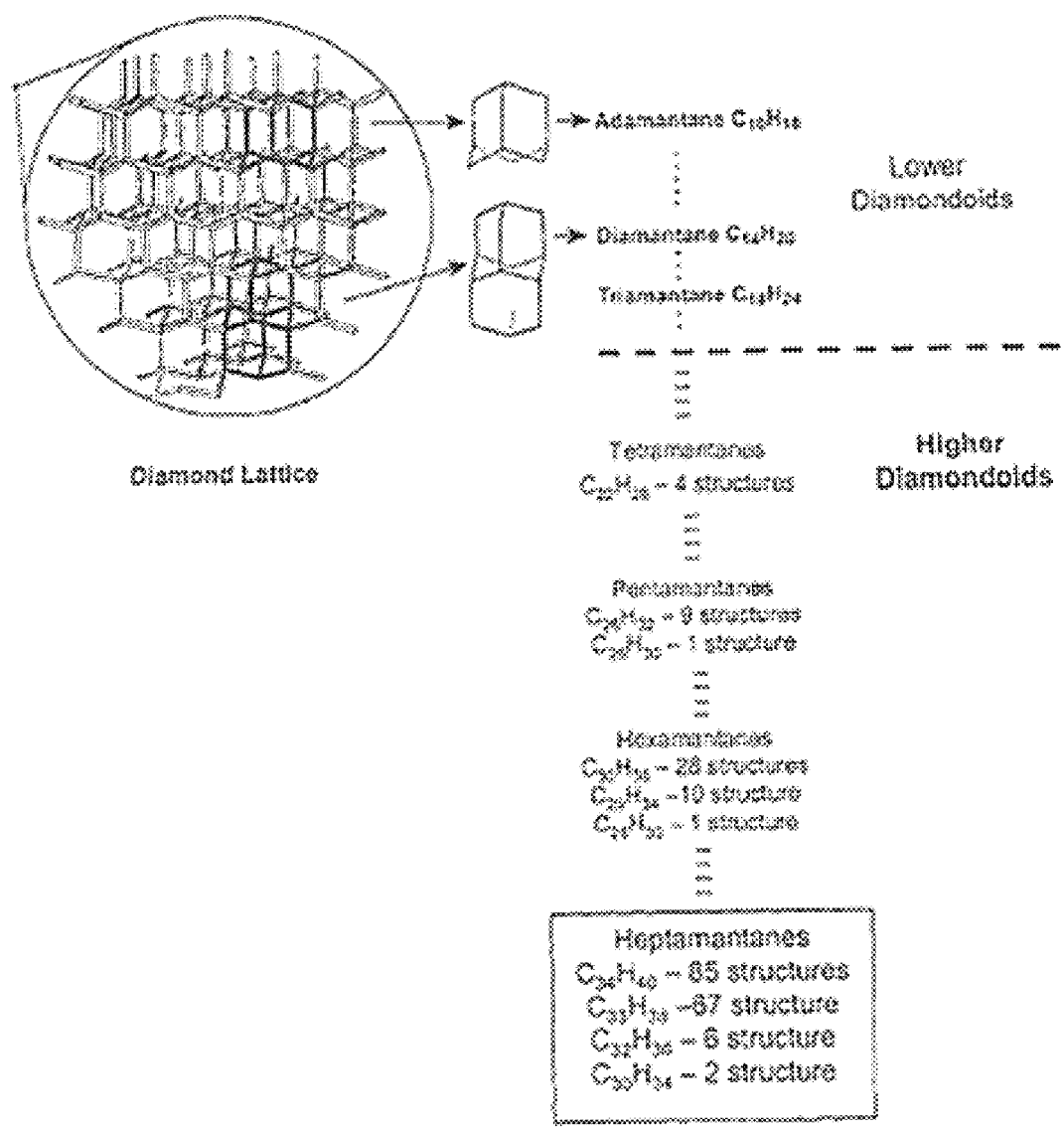
FIG. 1 illustrates the cage-shaped structure of diamondoids and their correlation to subunits of the diamond crystal lattice.

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "heptamantanes," "higher diamondoids" and "nonheptamantane higher diamondoids" as these terms are defined herein.

The terms "heptamantanes" refers to diamondoids that are the face-fused heptamers of adamantane. One hundred sixty possible unsubstituted heptamantane structures have been postulated. Among them, 85 of the one hundred sixty have the molecular formula $C_{34}H_{40}$ (molecular weight 448) and of these, 7 are symmetrical, having no enantiomers. Six have the molecular formula $C_{32}H_{36}$ (molecular weight 420) and 67 have the molecular formula $C_{33}H_{38}$ (molecular weight 434). There are two fully condensed unsubstituted heptamantanes having the molecular formula $C_{30}H_{34}$ (molecular weight 394). Each of the heptamantanes possesses a different structure. Heptamantanes include substituted materials as described for diamondoids, generally.

The term "heptamantane component" refers to any single such substituted or unsubstitued heptamantane, including optical isomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not heptamantane components are referred to as "nonheptamantane higher diamondoids."

The term "feedstock" or "hydrocarbonaceous feedstock" refers to hydro-carbonaceous materials comprising recoverable amounts of one or more heptamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. The latter is typically characterized as comprising components having a boiling point both below and above heptamantane components, which show molecular weights ranging from 394 to 448 and have a range of boiling points beginning at about 425° C. Typical feedstocks may also contain impurities such as sediment, metals including nickel and vanadium and other inorganics. They may also contain heteromolecules containing sulfur, nitrogen and the like. All of these materials which are not heptamantane components are referred to as "nonheptamantane materials or "nonpentamantane components."

The term "enriched" when used to describe the state of purity of one or more heptamantane components refers to such materials at least partially separated from nonheptamantane materials, and in the case of "enriched" individual heptamantane components, from other heptamantane components so as to be at a concentration at least 25 and preferably at least 100 times as great as the concentration exhibited in a feedstock. Preferably "enriched" heptamantane or "enriched" heptamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%, 95% or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate heptamantane components by removal of nonheptamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched heptamantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to enrich and isolate higher diamond compositions are set forth in U.S. Provisional Patent Application No. 60/262,842 filed Jan. 19, 2001; U.S. Provisional Patent Application No. 60/300,148 filed Jun. 21, 2001; U.S. Provisional Patent Application No. 60/307,063 filed Jul. 20, 2001; and U.S. Provisional Patent Application No. 60/312,563 filed Aug. 15, 2001. These applications are herein incorporated by reference in their entirety.

To obtain the heptamantane compositions described herein, a feedstock is selected such that said feedstock comprises recoverable amounts of heptamantane. Preferably, such feedstock comprises at least about 1 ppt (part per trillion) of heptamantanes components. It is understood, of course, that feedstocks having higher concentrations of heptamantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada.

The feedstocks used to obtain the compositions of this invention typically comprise nondiamondoid components having boiling points both below and above the heptamantane components as well as lower diamondoids and nonheptamantane higher diamondoids. A sufficient amount of these contaminants is removed from the feedstocks to provide treated feedstocks from which the heptamantane components can be enriched and recovered.

The removal of nondiamondoids, lower diamondoids and nonheptamantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nonheptamantane diamondoids having boiling points less than that of the lowest boiling point heptamantane component. Temperature profiles for distillation runs and the resulting distillation cuts can be determined on the basis of the heptamantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified heptamantane. The cuts, which are enriched in heptamantane or a particular heptamantane component of interest, are retained and may require further purification. For recovery of heptamantanes, the preferred distillation cuts are taken at atmosphere equivalent boiling point temperatures of from 350° to about 600° C., preferably from 395° to about 540° C., especially 395° to about 510° C. (atmospheric boiling points). It being understood that substituted heptamantanes may accordingly shift these preferred temperatures to higher temperatures due to the addition of substituent groups. Additional temperature refinements will allow for higher purity cuts for the heptamantane of interest. Other methods for the removal of contaminants and further purification of an enriched heptamantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours). The specific conditions employed are selected such that recoverable amounts of heptamantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a preferred embodiment, is not always necessary to facilitate the recovery, isolation or purification of the heptamantane components. Other separation methods may allow for the concentration of these heptamantane components to be sufficiently high in certain feedstocks that direct purification methods such as chromatography including preparative gas chromatography and high performance liquid chromatography and crystallization may be used to isolate heptamantane components.

Even after distillation or thermal degradation/distillation, further purification of the heptamantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated heptamantanes. These provisions can be combined. For example, preparative capillary gas chromatography can be coupled with high performance liquid chromatography as a first or subsequent separation method.

Further processing using these methods allow for more refined separations which can lead to a pure heptamantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the heptamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction", R. M. Smith, Elsevier Science, December 1997, incorporated herein by reference.

Compositions

This invention is directed to compositions comprising one or more heptamantane components wherein said compositions comprise at least about 25 weight percent heptamantane components based on the total weight of the diamondoids in the compositions. The compositions preferably comprise from about 50 to 100 weight percent, preferably about 70 to about 100 weight percent, more preferably about 90 to 100 weight percent and even more preferably about 95 to 100 weight percent heptamantane components based on the total weight of the diamondoids in the composition.

Such heptamantane-enriched compositions are obtained through the series of unit operations described above which can be used to concentrate heptamantanes to at least 25 times and more preferably at least 100 times the levels at which they occur in readily-available feedstocks. The total weight percent of heptamantane components in the compositions is preferably at least 10% by weight based upon the total weight of the composition. In a more preferred aspect the total weight percent of heptamantane components is from 50 to 100 weight percent, more preferably 70 to 100 weight percent and even more preferably 95 or 99 to 100 weight percent based upon the total weight percent of the composition.

In other aspects, the compositions comprise an enriched individual heptamantane component such that they contain from 70 to 100 weight percent, more preferably from 90 to 100 weight percent, even more preferably from 95 to 100 weight percent and most preferably from 99 to 100 weight percent of a single heptamantane component including isolated optical isomers thereof.

Heptamantane components occur with one hundred and sixty possible structures existing with four different molecular weights. This invention provides each of these heptamantane components as isolated material for the first time. In a most preferred embodiment, the composition aspects of this invention are directed to the two fully condensed heptamantanes having the molecular formula $C_{30}H_{34}$ (molecular weight 394) shown in FIGS. 25 through 28. These condensed and partially condensed heptamantanes can be named as in the referenced FIG.'s using the naming convention as outlined in Balaban et al.[7] Accordingly, this aspect is directed to compositions enriched in [121321] and/or [123124] heptamantane as well as isolated fractions of the molecular weight 394 heptamantane. Also these 394 heptamantanes can be optionally substituted, for example with methyl. In another preferred aspect, the compositions are directed to the eighty-five heptamantanes having the molecular formula $C_{34}H_{40}$ (molecular weight 448) and furthermore to the seven symmetrical isomers which have no enantiomers, see FIG. 25 and up. These materials and the 394 molecular weight heptamantanes are listed in the following table. This invention is also directed to the six heptamantanes having the molecular formula $C_{32}H_{36}$ (molecular weight 420) and sixty-seven having the molecular formula $C_{33}H_{38}$ (molecular weight 434). In the heptamantanes of molecular weight 420 there are a total of 2 symmetric: [12(31)41], [1(2)34(1)2]; and 2 asymmetric: [123(1)42], [123143]; heptamantanes. The asymmetric ones each have an enantiomer making the total number of mol. wt. 420 heptamantanes equal to six. In the heptamantanes of molecular weight 434, there are 5 symmetric: [121323], [123421], [12(13)41], [12(1,3)41], [1(2)31(2)3]; and 31 asymmetric heptamantanes of mol. wt. 434 represented by: [123134], [123142], [121231], [12(12)31], [121(2)32], [1213(1)2], [12(1)3(1)2], [12(1)314], [12(1)3(1)4], [12(1)321], [1213(2)4], [12(1)341], [121324][121341], [121(3)42], [12(1)342], [12(13)43], [123(1)23], [123132], [123(1)24], [1(2)3124], [123(1,2)4], [1(2)31(2)4], [12(3)132], [1231(3)4], [12(3)142], [1(2)3(1)42], [123(1)43], [123(2)14], [1234(1)2], [12(3)4(1)2]. Each asymmetric 4(1)2]. Each asymmetric mol. wt. 434 heptamantane has an enantiomer, so the total number of heptamantanes of mol. wt. 434 is 67. The composition aspects of this invention are directed to compositions comprising one or more of these heptamantanes and for the processes for recovering said compositions enriched with such heptamantane components.

Structure Figure Numbers for the 448 and 394 Molecular Weight Heptamantane

| Structure code # | FIG. Numbers | | Structure code | FIG. Numbers | |
|---|---|---|---|---|---|
| 123(4)21 | 29 | 30 | 121321 | 25 | 26 |
| 123(2)41 | 31 | 32 | 123124 | 27 | 28 |
| 1212(3)4 | 37 | 38 | 121342 | 33 | 34 |
| 121(2,3)4 | 39 | 40 | 121212 | 35 | 36 |
| 12(3,4)12 | 41 | 42 | 121213 | 59 | 60 |
| 12(12)34 | 43 | 44 | 121232 | 61 | 62 |
| 1(2)3(1,2)4 | 45 | 46 | 121234 | 63 | 34 |
| 121(2)34 | 47 | 48 | 121312 | 67 | 68 |
| 121(3)23 | 49 | 50 | 121314 | 69 | 70 |
| 121(3)24 | 51 | 52 | 121343 | 71 | 72 |
| 121(3)41 | 53 | 54 | 123214 | 75 | 76 |
| 121(3)43 | 55 | 56 | 123231 | 77 | 78 |
| 121(3)21 | 57 | 59 | 123234 | 79 | 80 |
| 1213(1)4 | 65 | 64 | 123241 | 81 | 82 |
| 1232(1)4 | 73 | 74 | 123412 | 115 | 116 |
| 1(2)3(1)24 | 83 | 84 | | | |
| 1(2)31(3)4 | 85 | 86 | | | |
| 1(2)3132 | 87 | 88 | | | |
| 1(2)3134 | 89 | 90 | | | |
| 1(2)3142 | 91 | 92 | | | |
| 12(1)324 | 93 | 94 | | | |
| 12(1)324 | 95 | 96 | | | |
| 12(1,3)42 | 97 | 98 | | | |
| 12(1,3)43 | 99 | 100 | | | |
| 12(13)32 | 101 | 102 | | | |
| 12(13)34 | 103 | 104 | | | |
| 12(3)1(2)3 | 105 | 106 | | | |
| 12(3)1(2)4 | 107 | 108 | | | |
| 12(3)1(3)4 | 109 | 110 | | | |
| 12(3)124 | 111 | 112 | | | |
| 12(3)134 | 113 | 114 | | | |
| 1212(1)3 | 117 | 118 | | | |
| 121(2)31 | 119 | 120 | | | |

This invention is also directed to mixtures of these isolated heptamantane components, as well as isolated substituted heptamantane components alone or together with non-substituted materials.

At the high heptamantane concentrations and purities achieved by the present invention, heptamantane components can form crystals. Accordingly, another aspect of this invention is directed to heptamantane crystals, whether crystals of a single heptamantane component, co-crystals comprising crystals of at least two heptamantane components or co-crystallize with other higher diamondoids, such as hexamantane components.

The heptamantanes recovered and isolated in this invention include substituted heptamantane components. These naturally-occurring substituted heptamantanes have similar properties to the unsubstituted heptamantane components described herein and are present in the feedstocks. Substituted heptamantanes may act as useful intermediates in various heptamantane applications or can be de-alkylated to yield the corresponding unsubstituted heptamantanes. Substituted heptamantanes contain 1 to 10 alkyl substituents, and more preferably 1 to 4 such substituents.

The most prevalent substituted heptamantanes in the feedstocks used are heptamantanes substituted with lower alkyls. The most prevalent of these are methyl and ethyl-substituted heptamantanes, including methyl, ethyl, dimethyl, and trimethyl heptamantanes.

Utility

These heptamantane-containing compositions are useful in micro- and molecular-electronics and nanotechnology applications. In particular, the rigidity, strength, stability, thermal conductivity, variety of structural forms and multiple attachment sites shown by heptamantanes makes possible accurate construction of robust, durable, precision devices with nanometer dimensions. These special structural characteristics set these compounds apart from acyclic molecules, from condensed-ring systems and even from bridged-ring counterparts. The great stability, nanometer size, variable yet rigid geometry, well defined distances for places of attachment, nonplanar bridgeheads lead to their unique features. Due to the rigidity, specialized geometry, 3-dimensional shape and nanometer size of the heptamantane components, it is expected that molecular aggregates and building blocks comprising them will enable construction and synthesis of a unprecedented array of desirable materials that will find applications in molecular electronic computing devices, reduced-size machines such as molecular robots and self-replicating manufacturing systems. Alternatively, the heptamantanes may be used as novel materials of construction with special chemical, optical, electric and thermal conductivity properties for coatings, film layering and other applications taking advantage of the diamond-like properties, etc.

In addition, heptamantane-containing compositions can also be used in a high-quality lubricant which exhibits a high Viscosity Index and a very low pour point.[4] When so employed, these lubricants comprise from about 0.1 to 10 weight percent heptamantanes.

Still further, these heptamantane-containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | |
|---|---|
| API = | American Petroleum Institute |
| ATM EQV = | atmospheric equivalent |
| EOR Traps = | end of run traps |
| FID = | flame ionization detector |
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

EXAMPLES

Example 1

Isolation of Heptamantane Components

The purpose of this example is to demonstrate procedures for the isolation of heptamantane components. These procedures employed Feedstock B and a pyrolysis step, however this procedure could be facilitated using other materials, such as Feedstock A, and without the pyrolysis step. After removal of lower boiling point nonheptamantane components (including some lower diamondoids and tetramantanes from the feedstock by distillation), the heptamantane components in this example were recovered by chromatography and crystallization. The distillation preferably can be operated to provide specific cuts, thus removing both lower and higher boiling point components, leaving only components within a desired boiling point range.

Figure 3:
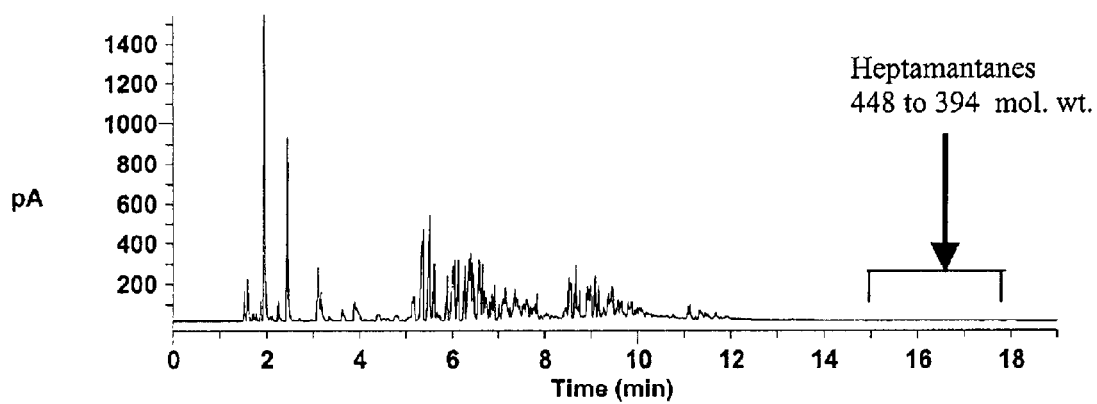
FIG. 3 illustrates the gas chromatogram of a gas condensate feedstock; one of the original feedstocks used in the Examples (Feedstock A). Heptamantanes are present at low concentrations, not detectable, but are shown in vacuum distillation fractions (FIG. 6).
Figure 4:
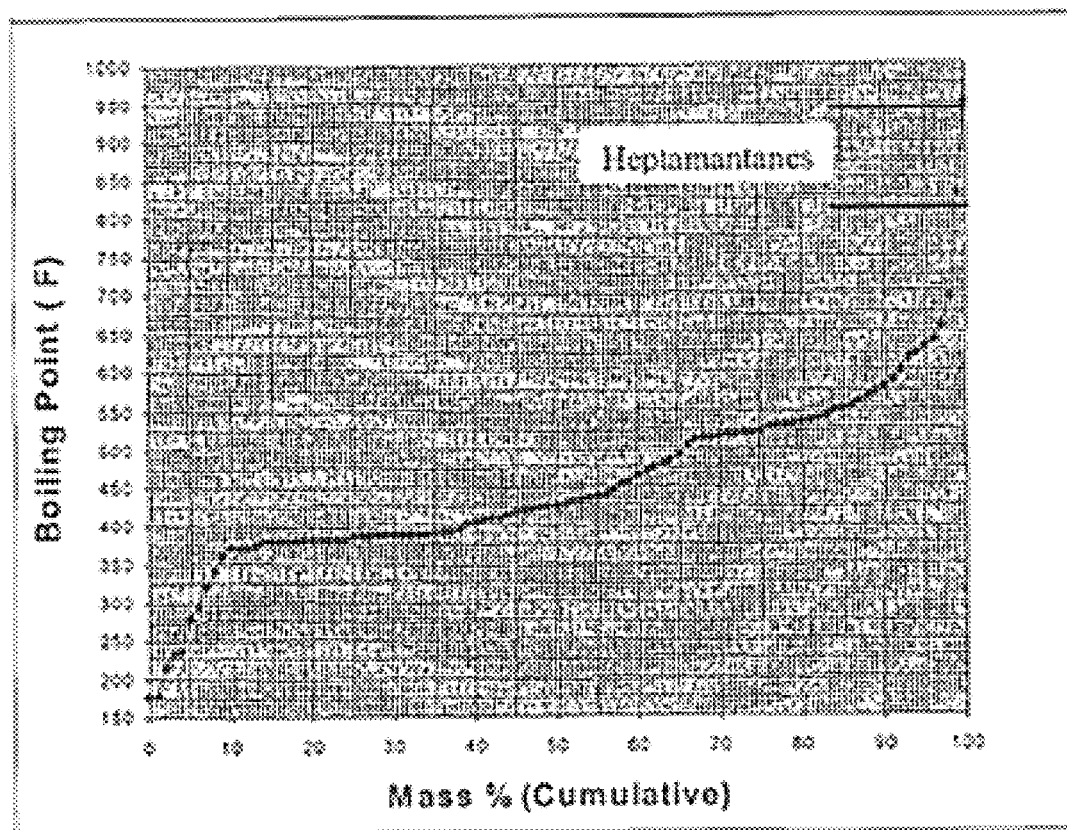
FIG. 4 illustrates a simulated distillation profile of a gas condensate feedstock containing petroleum byproducts used in the Examples (Feedstock B). Boiling points depicted are atmospheric equivalents. Heptamantanes were found in the atmospheric residue (650° F.+) of Feedstock B.

Step 1:

Suitable starting materials were obtained. These materials included a gas condensate, Feedstock A (a gas chromatogram of this material is depicted in FIG. 3), and a gas condensate containing petroleum byproducts Feedstock B (a high temperature simulated distillation profile of this type of material is depicted in FIG. 4). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2:

Samples from Feedstocks A and B were distilled into a number of fractions based on boiling points to separate the lower boiling point components (nondiamondoids and lower diamondoids) and to further concentrate and enrich heptamantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 5:
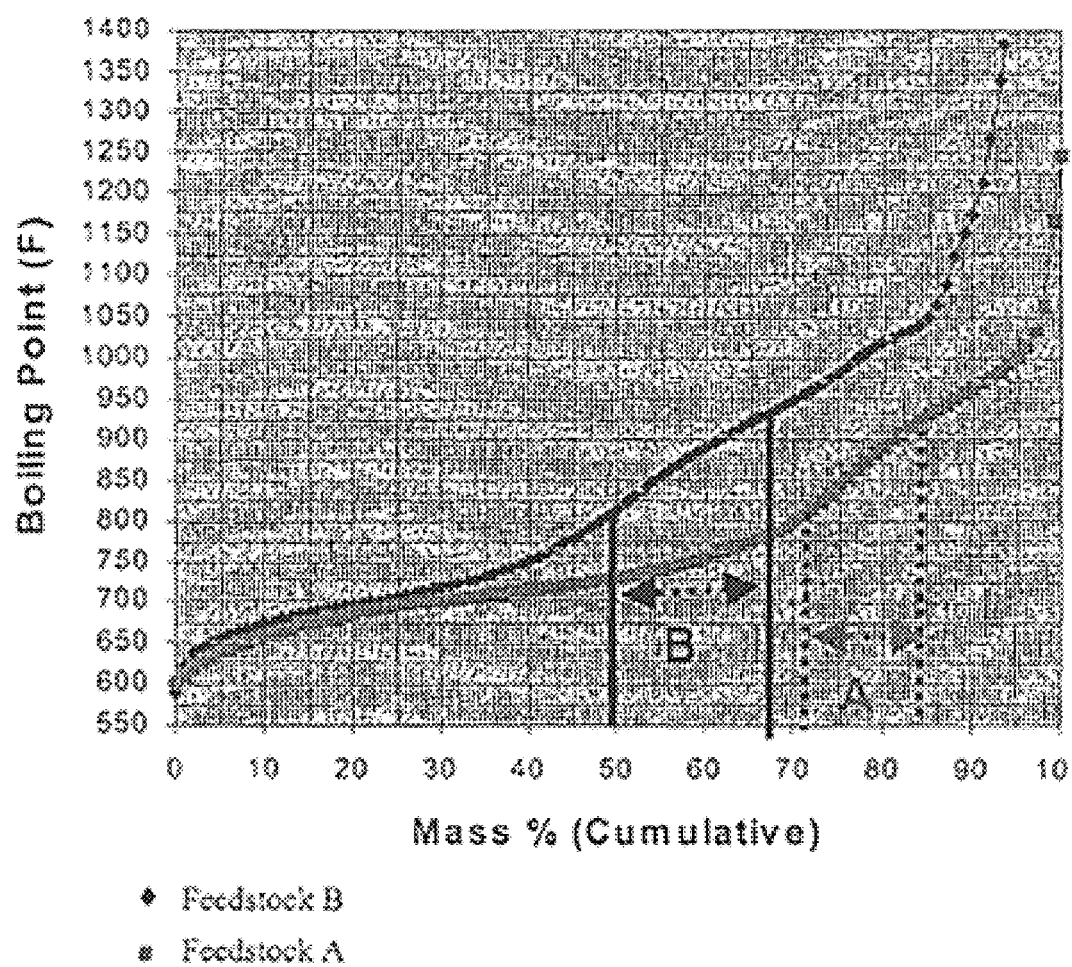
FIG. 5 illustrates a high temperature simulated distillation profile of atmospheric residue of diamondoid rich gas condensates; Feedstock A and Feedstock B. This Figure also illustrates the n-paraffin carbon number atmospheric equivalent boiling points. Labels A and B show the portions of each feedstock which contain the heptamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the heptamantane-containing fractions. In terms of atmospheric equivalent boiling points the heptamantanes were anticipated to be predominately within the range of 350° C. to about 6000° C. with a large portion within the range of 430° C. to about 510° C. The lower mass percent shown for the heptamantane-containing fractions of Feedstock B, as compared to Feedstock A was due to nondiamondoid materials in Feedstock B. The nondiamondoid material can be removed by subsequent processes such as pyrolysis.

Figure 6:
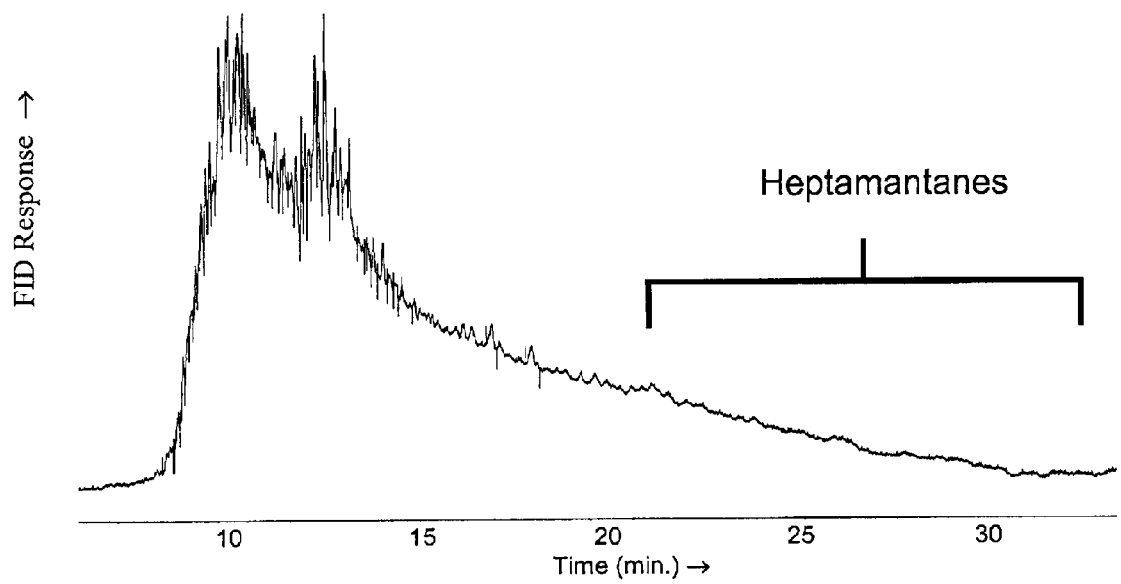
FIG. 6 illustrates gas chromatographic profiles of vacuum distillate residue containing heptamantanes and higher diamondoids from a gas condensate, Feedstock A.

A sample of gas condensate, Feedstock A was distilled into 38 fractions to remove lower diamondoids and concentrate higher diamondoids including heptamantanes as verified by GC (see FIG. 6). Fraction 38 was a recovered distillate, predominately boiling in the range of from 700 to 850° F. (atmospheric equivalent). The boiling points of these fractions are given as atmospheric equivalent temperatures, however, the actual distillation can occur at other pressures and corresponding temperatures.

Figure 12:
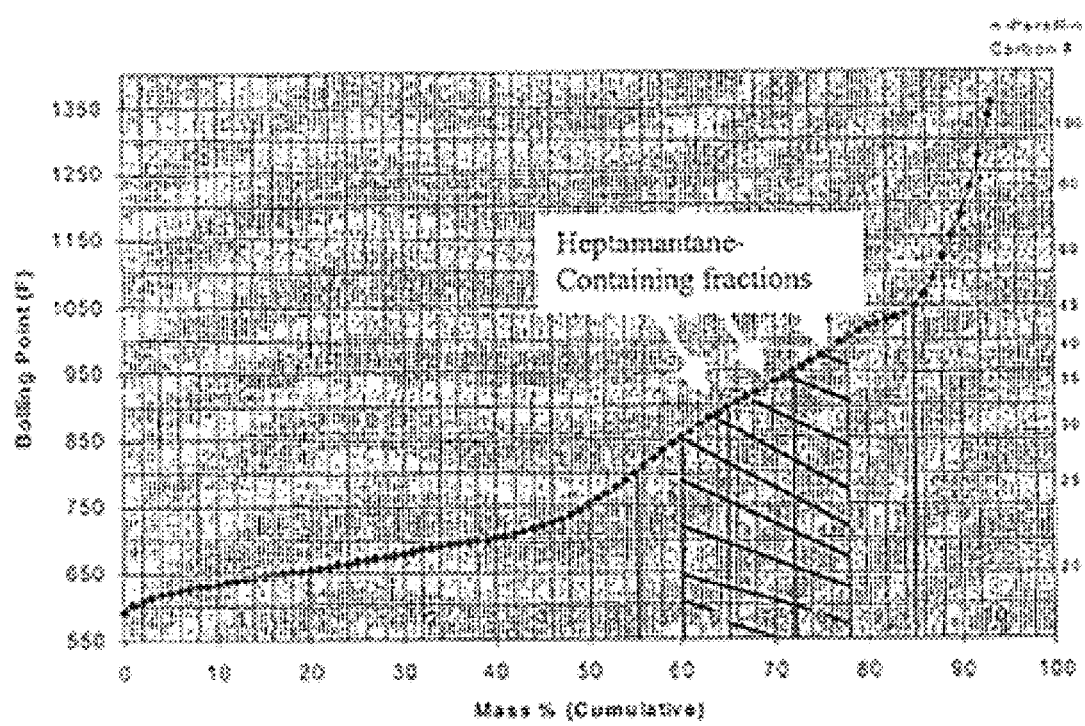
FIG. 12 illustrates a high temperature simulated distillation profile of Feedstock B using the atmospheric distillation 650° F.+bottoms as feedstock. This FIG. also illustrates the targeted cut points (1–10) for higher diamondoid isolations. Heptamantane components are contained primarily in distillate fractions 6 through 8.

Additionally, Feedstock B was distilled into fractions containing higher diamondoids guided by a high-temperature simulated-distillation curve (FIG. 12).

Figure 13:
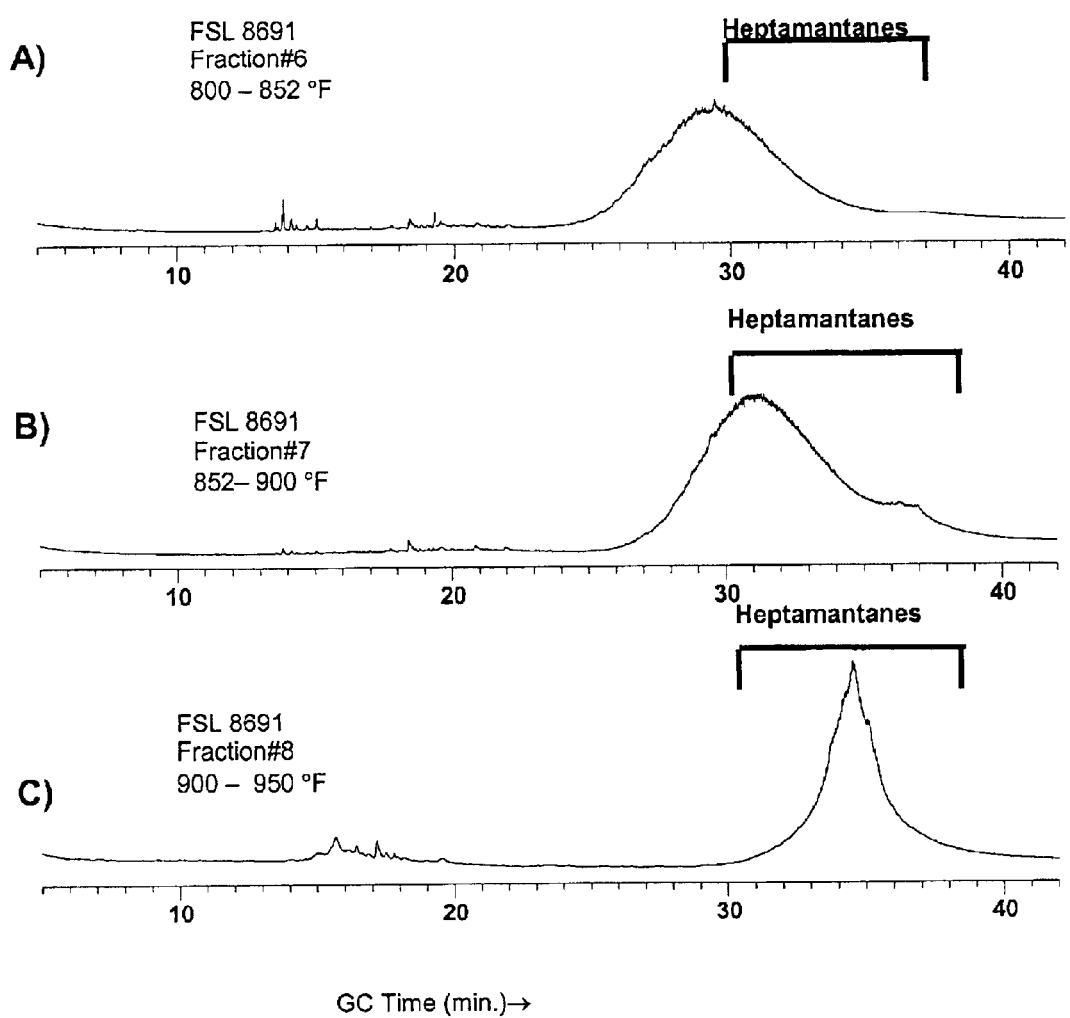
FIGS. 13(A, B, C) illustrates the gas chromatograms of vacuum distillate Fractions #6, #7, and #8 of Feedstock B atmospheric distillation 650° F.+bottoms illustrated in FIG. 12 and exemplified in Example 1.

Comparison of FIGS. 6 and 13 shows that Feedstock B contained impurities not present in Feedstock A. The feed to the high temperature distillation process was the atmospheric 650° F.+bottoms. Complete Feedstock B distillation reports are given in Tables 2A&B. Tables 3A&B, illustrate the distillation reports for Feedstock B 643° F.+distillation bottoms.

TABLE 2A

Distillation Report for Feedstock B
(FSL #8471)
Feedstock B
Column Used: Clean 9" x 1.4" Protruded Packed

| | VAPOR | DISTILLATION RECORD | | | | NORMALIZED | | ACTUAL | |
| --- | --- | --- | --- | --- | --- | --- | --- | --- | --- |
| CUT | TEMP ° F. ST - END | WEIGHT G | VOLUME ml @ 60° F. | API 60/60 | DENSITY @ 60° F. | WT PCT | VOL PCT | WT PCT | VOL PCT |
| 1 | 226 – 349 | 67.0 | 80 | 38.0 | 0.8348 | 7.61 | 8.54 | 7.39 | 8.26 |
| 2 | 349 – 491 | 507.7 | 554 | 22.8 | 0.9170 | 57.65 | 59.12 | 55.98 | 57.23 |
| 3 | 491 – 643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS 643 + | | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B
(FSL #8471)
Feedstock B
Column Used: Clean 9" x 1.4" Protruded Packed

| TEMPERATURE DEGREES F. | | | | | | | | | API GRAVITIES | |
| --- | --- | --- | --- | --- | --- | --- | --- | --- | --- | --- |
| VAPOR | | | | | | | | | OBSERVED | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | | START OVERHEAD | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | Cut 2 looks Milky, White crystals form in Run Down Line. Heat Lamp applied to drip tube. Cool to transfer btms to smaller flask. | | | | | | | |
| 208 | 437.7 | 323 | 10.000 | 3:1 | | | START OVERHEAD | | | |
| 378 | 643.3 | 550 | 10.000 | 3:1 | 3 | 268 | 269.6 | 9.9 | 75.0 | 9.1 |
| | | | Shutdown due to dry pot | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B
(FSL #8691)
Feedstock B - Atmospheric distillation resid 650° F. + bottoms
Column Used: Sarnia Hi Vac

| TEMPERATURE DEGREES F. | | | | | | | API GRAVITIES | | | |
|---|---|---|---|---|---|---|---|---|---|---|
| VAPOR | | | | | | | OBSERVED | | | |
| VLT | ATM EQV. | POT | PRESSURE TORR | REFLUX RATIO | CUT NO | VOL ml 60° F. | WEIGHT G | HYD RDG | TEMP ° F. | 60° F. |
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 3B

Distillation Report for Feedstock B-btms
(FSL #8691)
Feedstock B - Atmospheric distillation resid 650° F. + bottoms
Column Used: Sarnia HiVac

| CUT | VAPOR TEMP ST - END, ° F. | | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|---|
| 1 | 601 | – | 656 | 666.4 | 639 | 4.1 | 1.0435 | 20.12 | 19.38 | 20.03 | 19.40 |
| 2 | 656 | – | 702 | 666.9 | 646 | 5.6 | 1.0321 | 20.14 | 19.59 | 20.05 | 19.62 |
| 3 | 702 | – | 752 | 334.3 | 330 | 8.3 | 1.0122 | 10.09 | 10.01 | 10.05 | 10.02 |
| 4 | 752 | – | 800 | 167.7 | 173 | 14.5 | 0.9692 | 5.06 | 5.25 | 5.04 | 5.25 |
| 5 | 800 | – | 852 | 167.3 | 181 | 21.7 | 0.9236 | 5.05 | 5.49 | 5.03 | 5.50 |
| 6 | 852 | – | 900 | 167.1 | 181 | 21.9 | 0.9224 | 5.05 | 5.49 | 5.02 | 5.50 |
| 7 | 900 | – | 950 | 238.4 | 257 | 21.2 | 0.9267 | 7.25 | 7.79 | 7.17 | 7.80 |
| 8 | 950 | – | 976 | 85.4 | 91 | 18.9 | 0.9408 | 2.58 | 2.76 | 2.57 | 2.76 |
| 9 | 976 | – | 1000 | 80.8 | 85 | 18.2 | 0.9452 | 2.44 | 2.58 | 2.43 | 2.58 |
| 10 | 1000 | – | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.00 | 100.00 | 99.56 | 100.15 |
| LOSS | | | | 14.6 | −5 | | | | | 0.44 | −0.15 |
| FEED | | | | 3326.3 | 3293 | 8.6 | 1.0100 | | | 100.00 | 100.00 |
| BACK CALCULATED API & DENSITY | | | | | | 9.4 | 1.0039 | | | | |

TABLE 4

Elemental Composition of Feedstock B
Analyses on Feedstock B Atmospheric Distillation 650 + F Resid

| Measured | Value |
| --- | --- |
| Nitrogen | 0.991 wt % |
| Sulfur | 0.863 wt % |
| Nickel | 8.61 ppm |
| Vanadium | <0.2 ppm |

Table 4 illustrates data from elemental analyses of Feedstock B atmospheric distillation (650+° F.) residue including some of the identified impurities. Table 4 displays the weight percent nitrogen, sulfur, nickel and vanadium present within this feedstock. These materials are removed in subsequent steps.

Step 3:

The higher diamondoids enriched by the separations of Step 2 were further treated to isolate a heptamantane fraction. In one case the distillation fraction 38 of Feedstock A was passed through a silica-gel gravity liquid chromatographic column (using cyclohexane elution solvent) to remove polar compounds and asphaltenes and concentrate higher diamondoids. The use of silver nitrate impregnated silica gel (10% by weight $AgNO_3$) provides cleaner diamondoid-containing fractions by removing the free aromatic and polar components. Higher diamondoids elute in the first eluting cyclohexane fraction off the column (before aromatic hydrocarbons appeared in the column eluent column. While it is not necessary to use this chromatographic separation method, it facilitates subsequent steps.

Alternatively, pyrolysis products (as disclosed in Example 2) prepared using distillate fractions of Feedstock B could be passed through a silica-gel or $AgNO_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Step 4:

The eluent from the column chromatography was analyzed by GC/MS to determine the GC retention times of heptamantanes. Individual heptamantane components with molecular weight 394 and 448 were assigned a number according to their elution order on our GC/MS assay. For molecular weight 448 heptamantanes only the most abundant were selected, simply for convenience. Similar assays could be prepared for the other molecular weight heptamantanes, see Example 4. This assigned number was used to identify individual heptamantanes in subsequent analyses. Note that enantiomeric pairs are not resolved in this analysis and so these enantiomeric pairs (racemic mixtures) were assigned a single number. Typical GC/MS retention times for heptamantane components are shown in FIG. 15.

Figure 7:
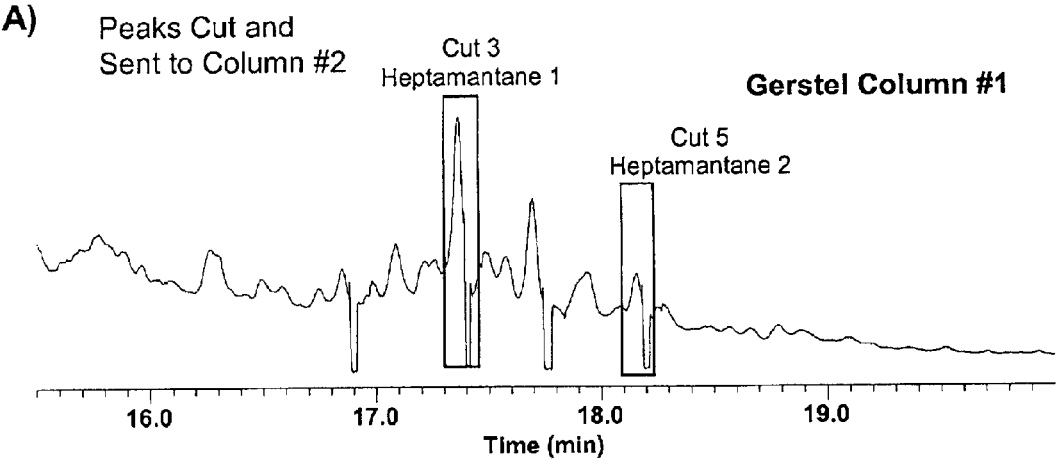
FIGS. 7(A, B) illustrates the preparative capillary gas chromatographic data for heptamantane isolations.
Figure 7:
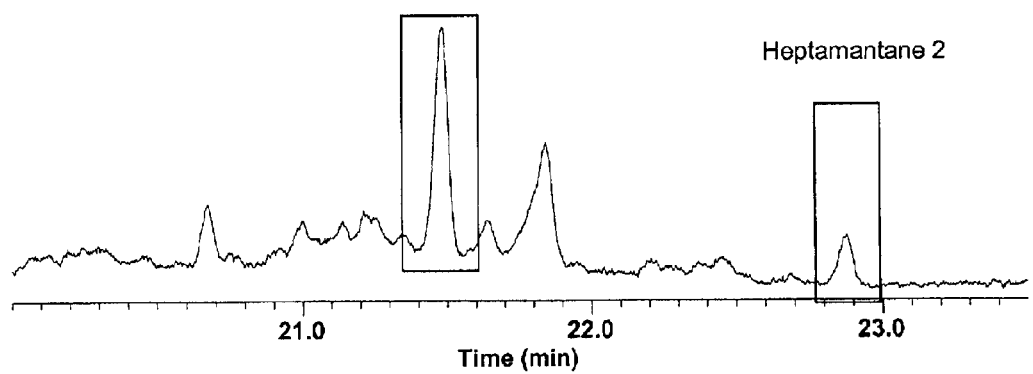

Step 5:

A two-column preparative capillary gas chromatograph was then used to isolate heptamantanes from the distillate fractions of Step 2 cleaned-up by the column chromatography of Step 3. The cut times for the heptamantanes were set for the first preparative capillary GC column, methyl silicone DB-1 equivalent, using the retention times and patterns from GC/MS assay (from step 4 above). An exemplary result is shown in the top of FIG. 7A, identified as "peak cut and sent to column 2" which contains two of the heptamantane from Feedstock B. The preparative capillary gas chromatograph used was manufactured by Gerstel, Inc., Baltimore, Md., USA. However, other gas chromatographs could be used.

Figure 8:
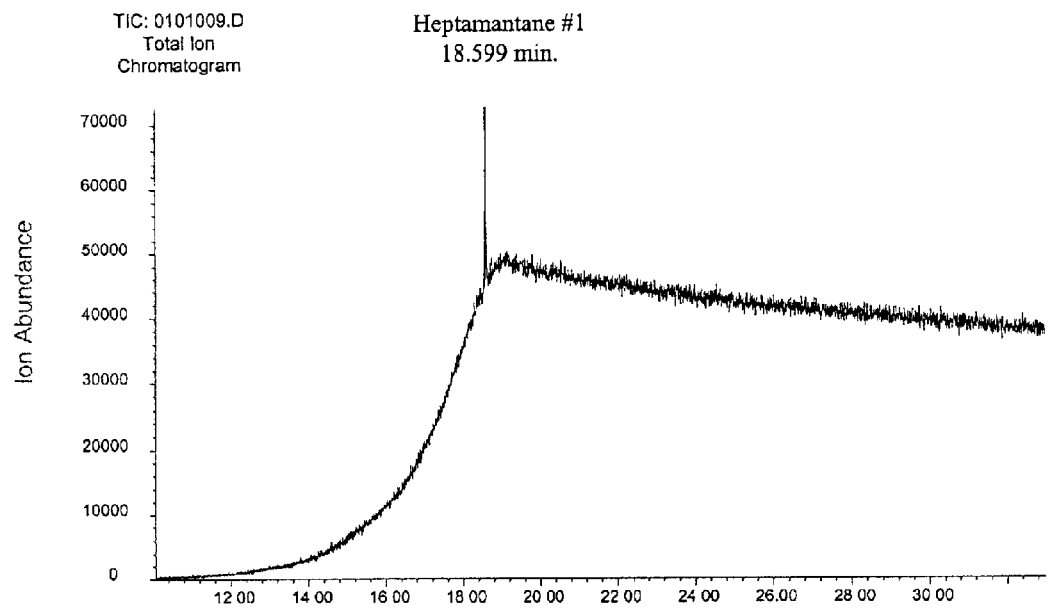
FIGS. 8(A, B) illustrates the GC/MS total ion chromatogram and mass spectrum of a heptamantane #1 isolated by preparative capillary gas chromatography.
Figure 8:
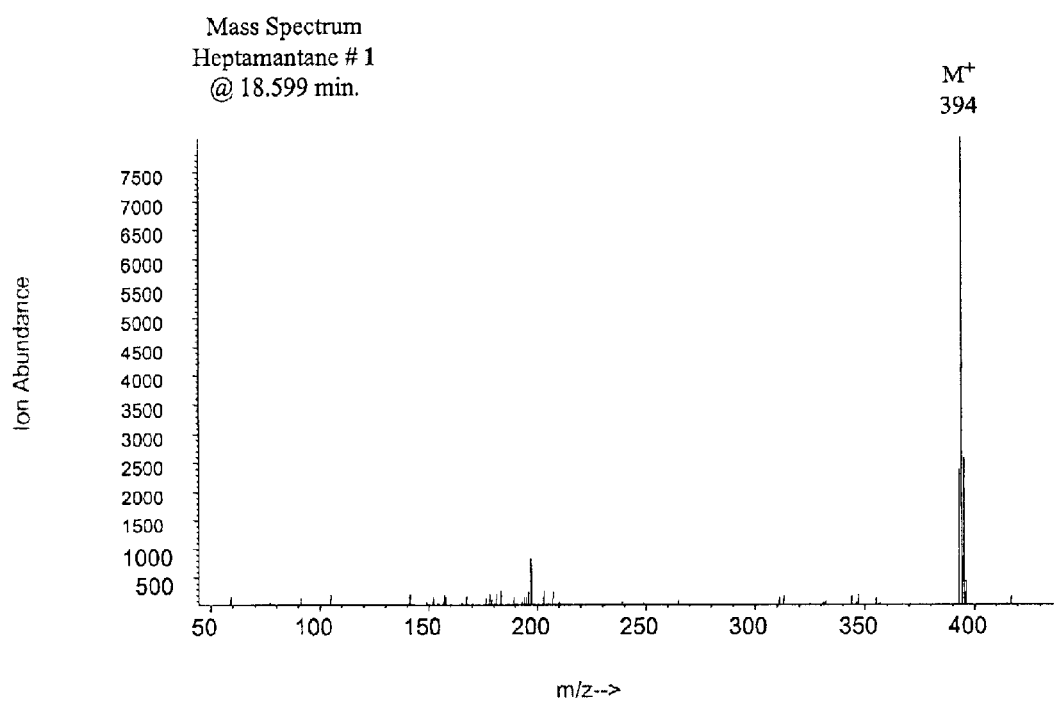
Figure 9:
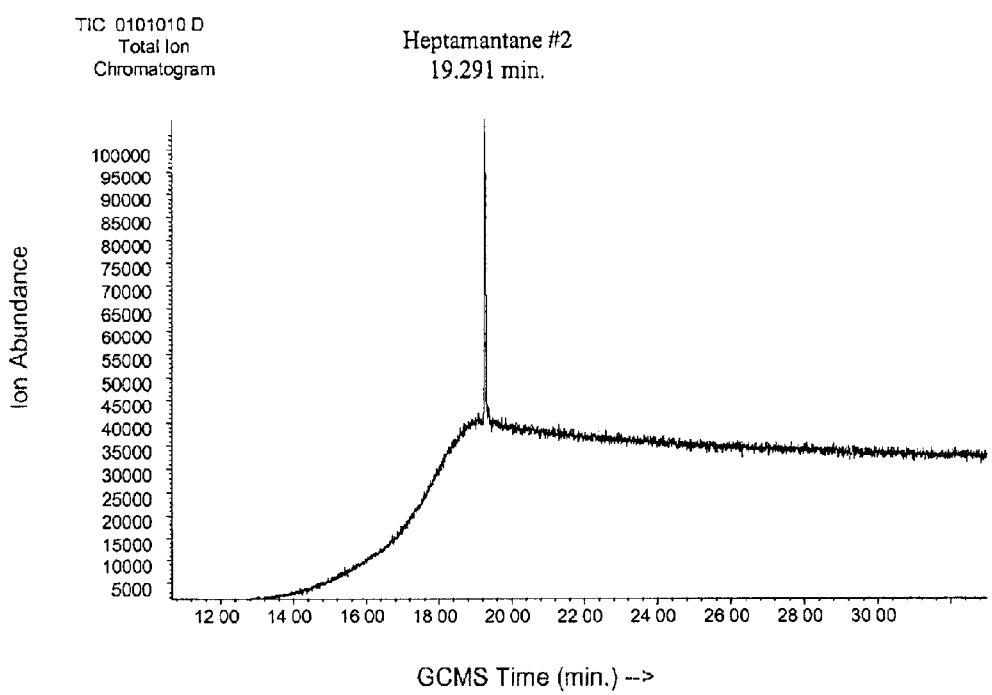
FIGS. 9(A, B) illustrates the GC/MS total ion chromatogram and mass spectrum of a heptamantane #2 highly concentrated by preparative capillary gas chromatography.
Figure 9:
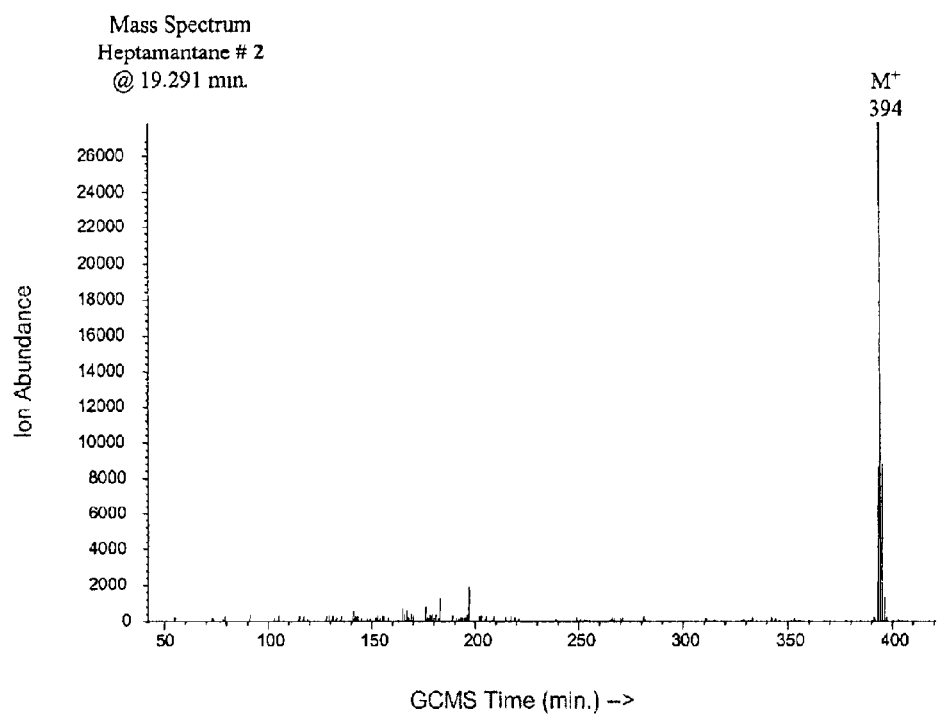

The first column was used to concentrate the heptamantanes by taking cuts that were then sent to the second column (see FIG. 7B illustrated for heptamantane components #1 and #2). The second column, phenyl-methyl silicone a DB-17 equivalent, further separated and purified the heptamantane components and then was used to isolate peaks of interest and retain them into individual vials (traps 1–6). GC trap fraction 2 was collected and further processed for the separation of heptamantane component #1. GC trap fraction 4 was collected and further processed for the separation of heptamantane component #2. Subsequent GC/MS analysis of trap #2 material (FIG. 8) showed it to be heptamantane component #1 based upon the earlier run GC/MS assay of step 4. Similarly, the GC analysis of trap #4 material (FIG. 9) showed it to be heptamantane component #2. This procedure could be repeated to isolate the other heptamantane components including the racemic pairs.

Figure 2:
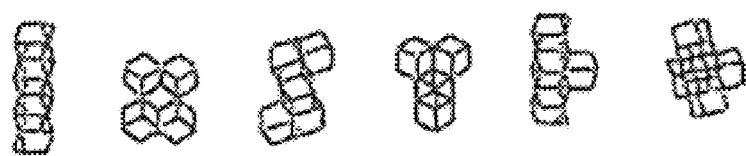
FIG. 2 illustrates the carbon framework example of a symmetrical and an enantiomeric heptamantane.
Figure 2:
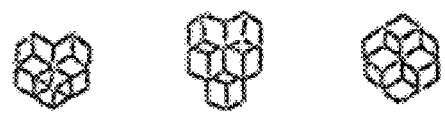
Figure 2:
Figure 2:
Figure 2:
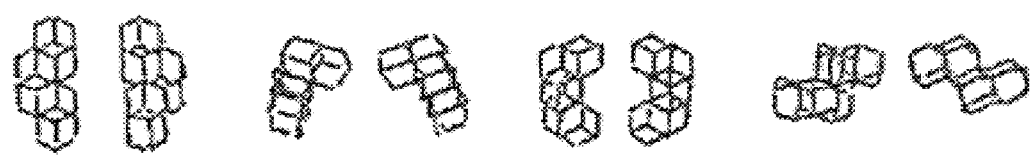
Figure 2:
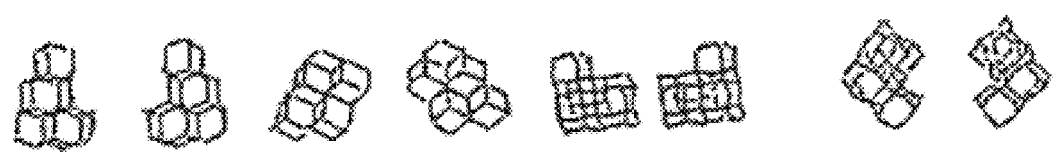
Figure 10:
FIG. 10 illustrates photomicrographs of heptamantane #1 crystals isolated from Feedstock B by preparative gas chromatography (FIGS. 7 and 8).
Figure 10:
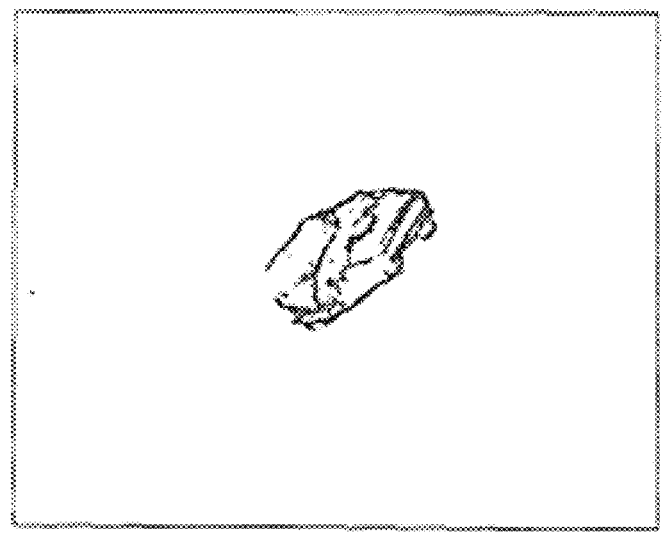
Figure 11:
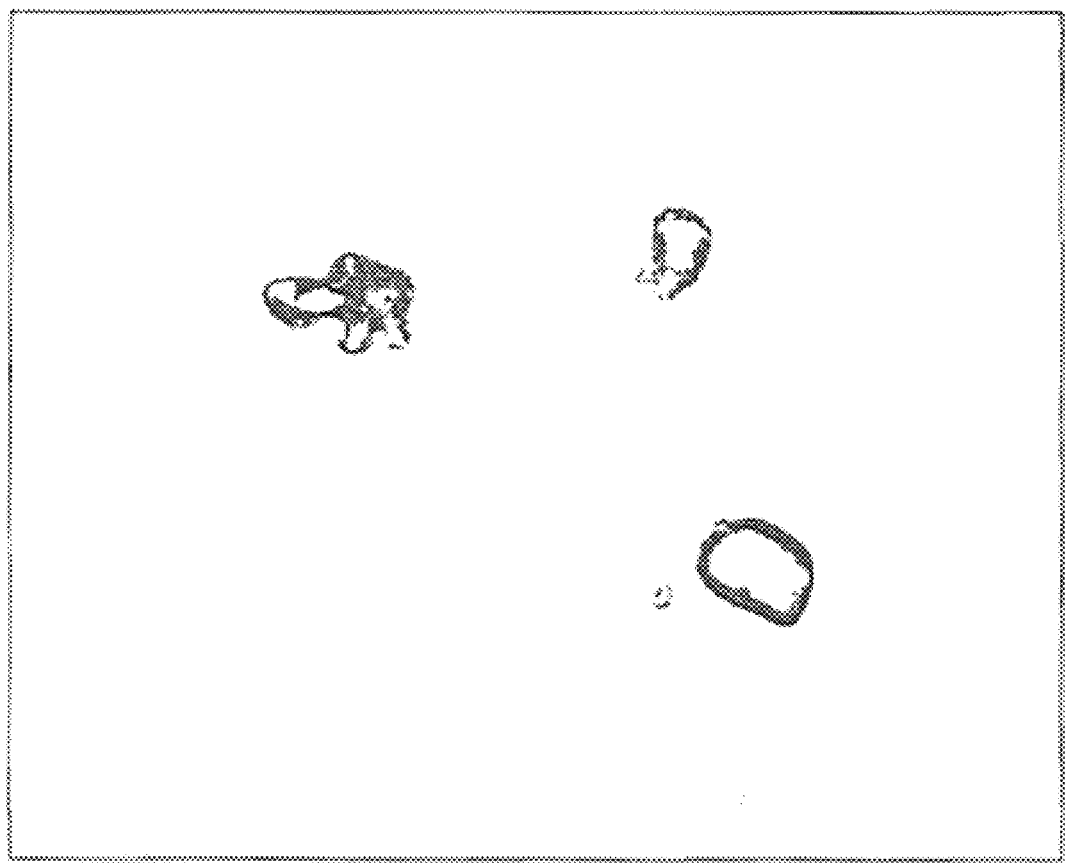
FIG. 11 illustrates a photomicrograph of heptamantane #2 crystals isolated from Feedstock B by preparative gas chromatography (FIGS. 7 and 9).

Step 6:

The highly concentrated heptamantane components were then allowed to crystallize either directly in the trap or from solution. Under the microscope at 30× magnification, crystals were visible in preparative GC trap fraction 2 (see FIG. 10). These crystals were perfectly clear and showed high refractive index. Crystals of heptamantane component #1 had never existed before this isolation. Where concentrations are not high enough for crystallization to occur, further concentration by preparative GC may be necessary. Examples of carbon framework structures of heptamantane components are shown in FIG. 2, including heptamantane having enantiomeric forms. Detailed structural drawings are given in FIGS. 25 through 120. FIG. 11 is a photomicrograph of heptamantane component #2 that crystallized in preparative GC trap 4. Crystals of heptamantane component #2 had never existed before this isolation.

Step 7:

After obtaining crystals of suitable size, non enantiomeric heptamantane materials could be sent for structural determination using X-ray diffraction. Enantiomeric heptamantanes can undergo further separations to resolve their two components.

Example 2

Enrichment of Heptamantanes Using Pyrolysis

A thermal degradation method using pyrolysis was developed to further purify distillate fractions such as distillate fractions #6–8 obtained from Feedstock B—Atmospheric distillation 650° F.+bottoms (Table 3 A/B) exploiting the great thermal stability of the heptamantanes relative to other crude oil components. FIGS. 13(A,B,C) respectively, shows the GC profiles of the distillate fractions #6–8 from Feedstock B—Atmospheric distillation 650° F.+bottoms (see FIG. 12 and Table 3A&B).

Removal of Non-Diamondoids Using Pyrolysis

Figure 14:
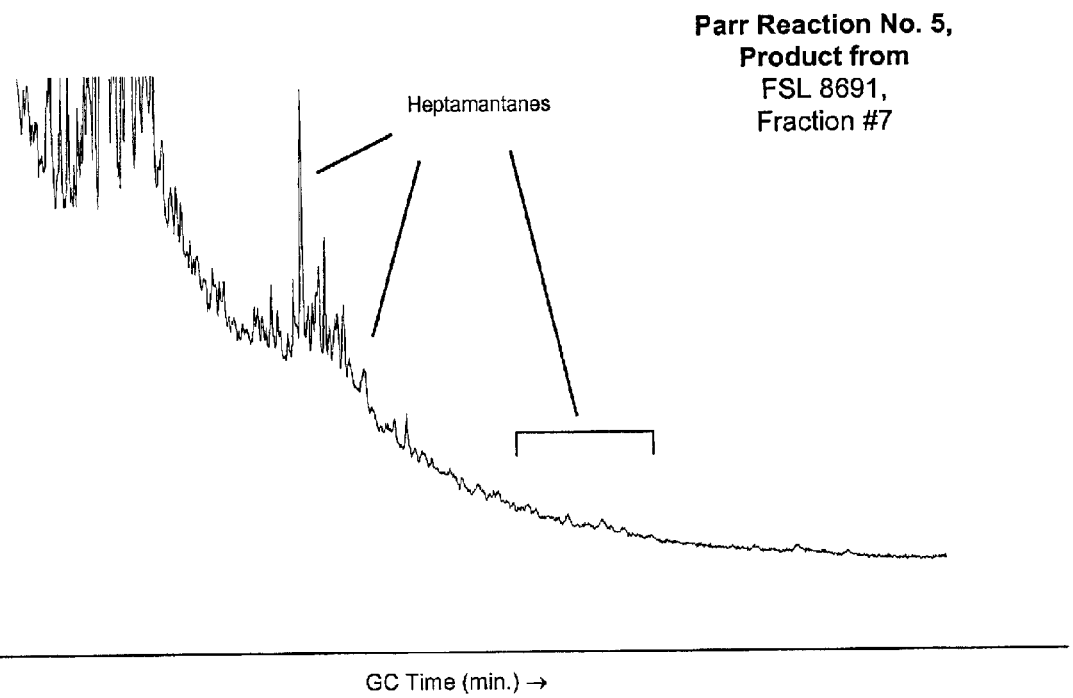
FIGS. 14(A, B) illustrates the gas chromatograms of the concentration of heptamantanes using pyrolysis.
Figure 14:
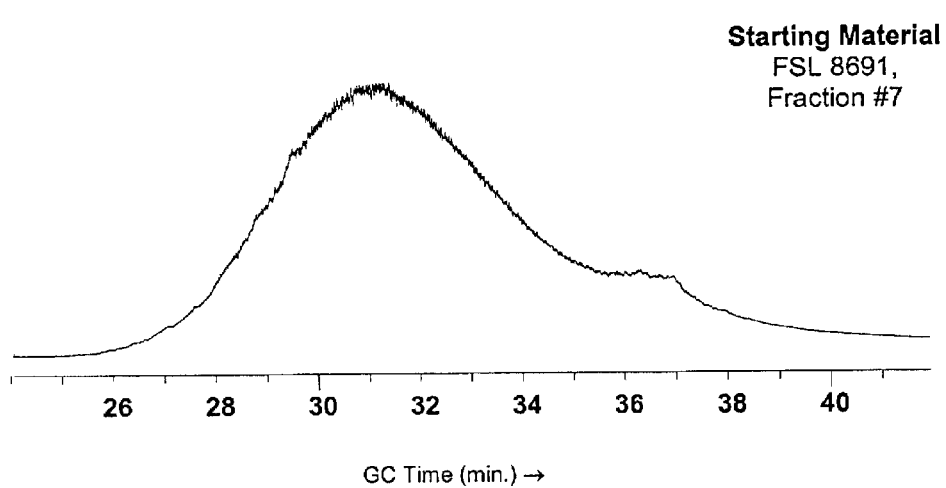

This method uses a reactor to pyrolyze and degrade a portion of the non-diamondoid components while enriching the diamondoids in the residue. Such reactors can operate at a variety of temperatures and pressures. FIGS. 14(A,B) illustrates this method and show a gas chromatogram of the Feedstock B 650° F.+distillation fraction 7 (Table 3, FIG. 13) before pyrolysis and the resulting pyrolysis product. Prior to pyrolysis, the heptamantane peaks are obscured by the presence of non-diamondoid components (FIG. 14B). Pyrolysis can be used to degrade the non-diamondoid components to easily removable gas and coke like solids. As shown in FIG. 14A, the heptamantane peaks are visible after pyrolysis.

A PARR® reactor, from PARR INSTRUMENT COMPANY, Moline, Ill., was used to process the distillation fractions obtained from vacuum distillation of a feedstream. For this example, Feedstock B 650° F.+distillation fraction 7 was used as a feedstock for pyrolysis. Pyrolysis was then conducted on 18.6 grams of this sample by heating the sample under vacuum in a vessel at 450° C. for 16.3 hours.

FIG. 14B shows the gas chromatogram of the distillation fraction and FIG. 14A shows the chromatograph of the products of the pyrolytic process. A comparison of the traces in FIGS. 14(A,B) show that the pyrolysis process has removed major non-diamondoid components leaving a residue enriched in heptamantane components.

Example 3

Isolation of Heptamantanes Using HPLC

In addition to the gas chromatography and pyrolysis methods described above, HPLC was also shown to provide sufficient enrichments of some heptamantanes to allow for their crystallization. In some cases, reverse-phase HPLC with acetone as mobile phase can be used to effect this purification. A preparative ODS HPLC run of Feedstock B distillate cut 6 pyrolysis product saturated hydrocarbon fraction was performed and the HPLC chromatogram recorded using a differential refractometer: results are shown in FIG. 15. Fractions where taken during the run as indicated in FIG. 15. Most heptamantanes were found by GS/MS analysis of the fractions to display a separate elution time on HPLC as indicated in FIG. 15. This is somewhat unexpected due to the similarity of the 448 molecular weight heptamantane isomers, but demonstrates the significant variation in properties of these heptamantanes based on differences in their carbon framework.

Figure 16:
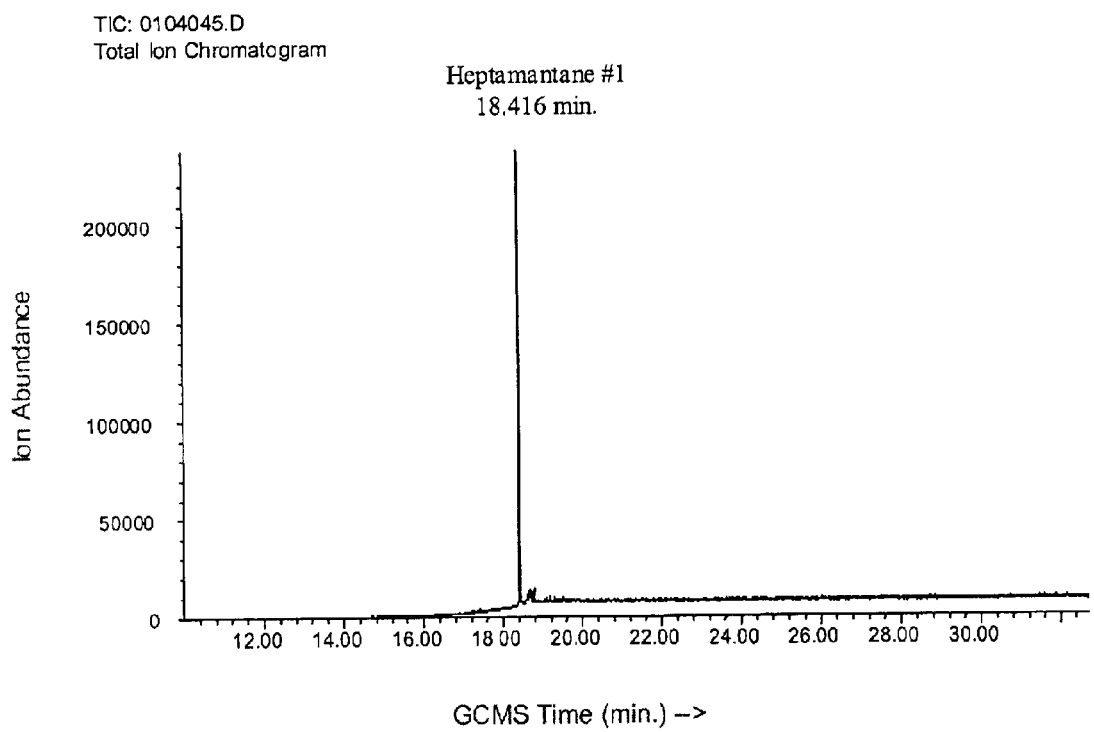
FIGS. 16(A, B) illustrates GC/MS total ion chromatogram (TIC) and mass spectrum of heptamantane component #1 in ODS HPLC fraction #45 (FIG. 15).
Figure 16:
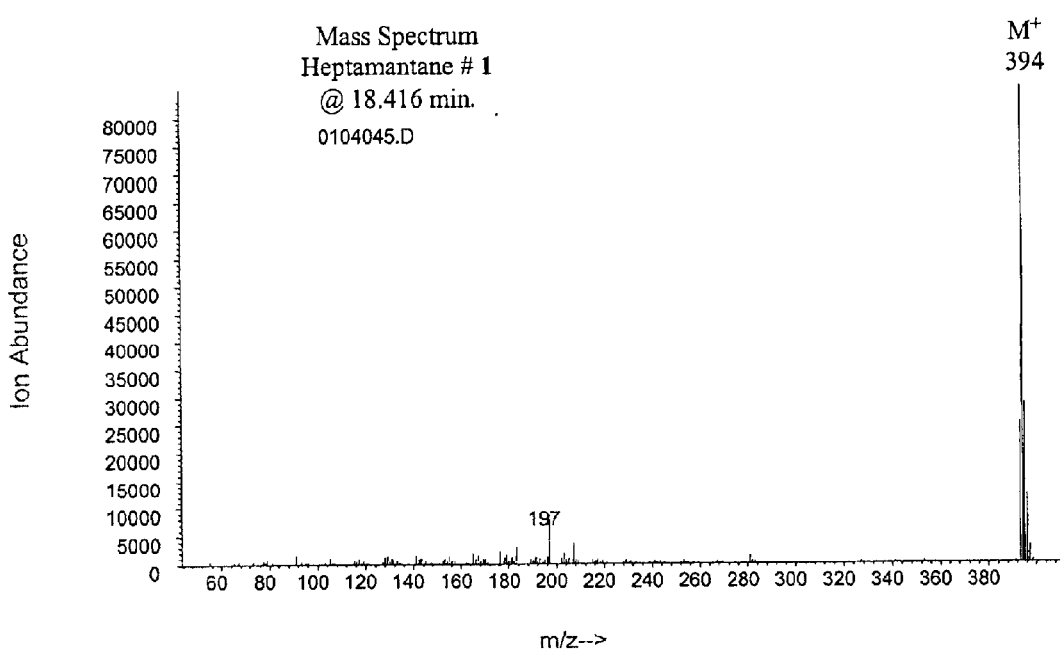
Figure 18:
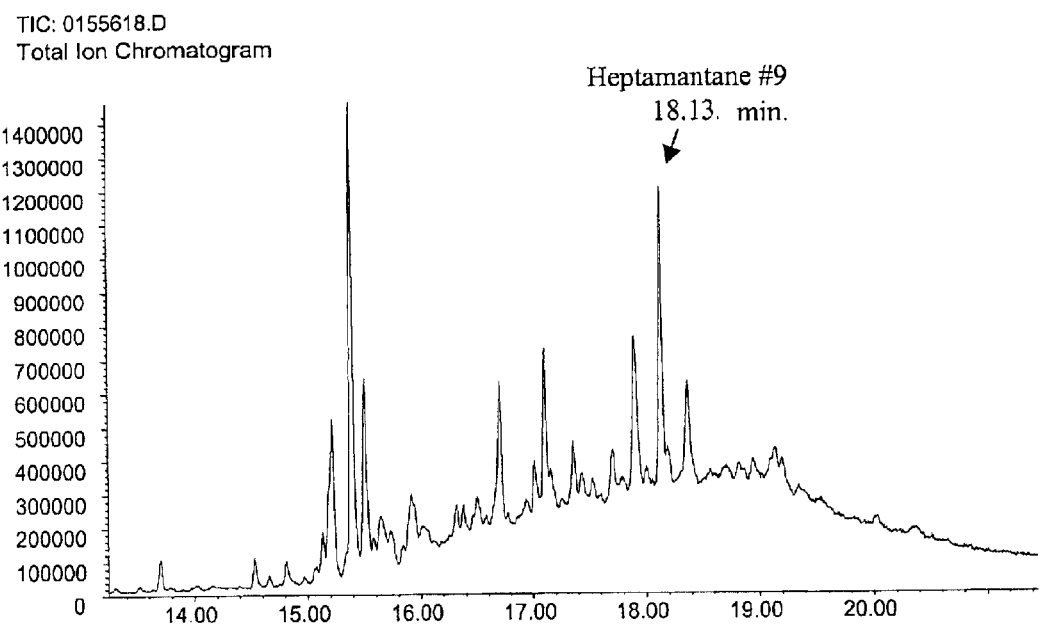
FIGS. 18(A, B) illustrates GC/MS total ion chromatogram (TIC) and mass spectrum of heptamantane component #9 in ODS HPLC fraction 61 (FIG. 15).
Figure 18:
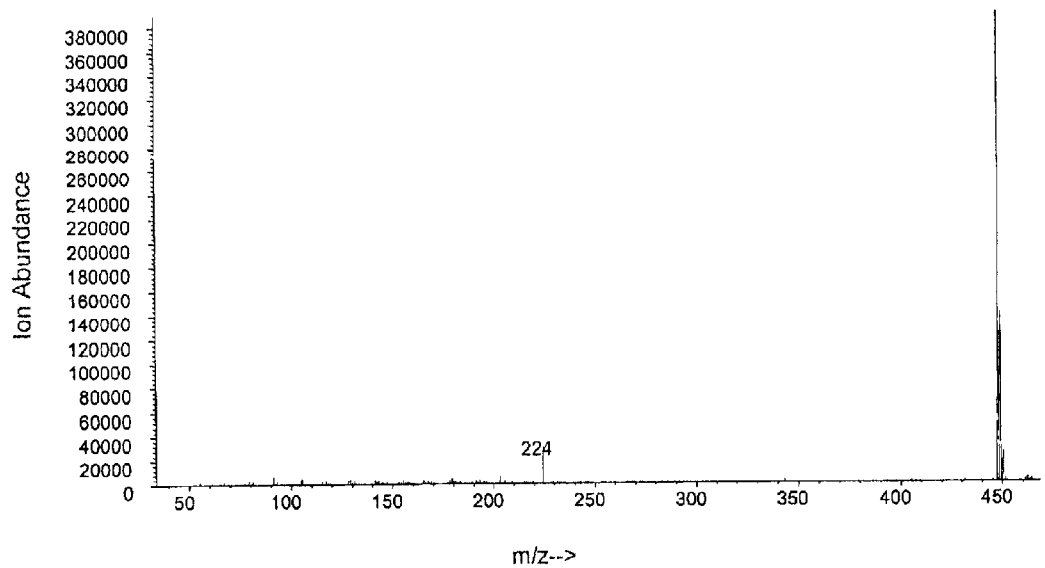
Figure 19:
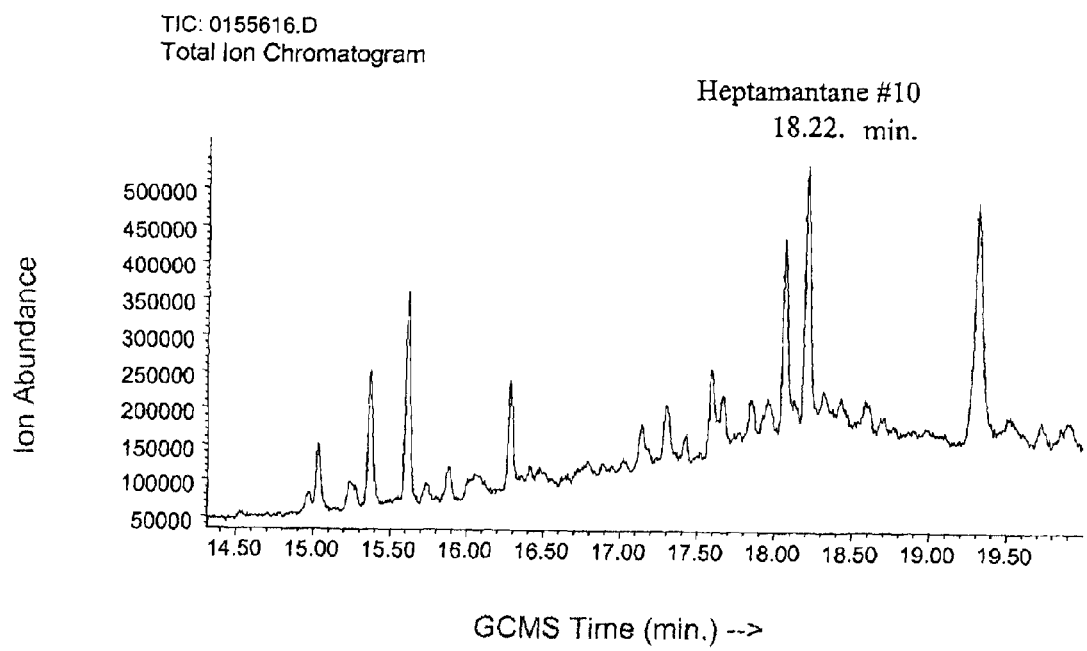
FIGS. 19(A, B) illustrates GC/MS total ion chromatogram (TIC) and mass spectrum of heptamantane component #10 in ODS HPLC fraction 87 (FIG. 15).
Figure 19:
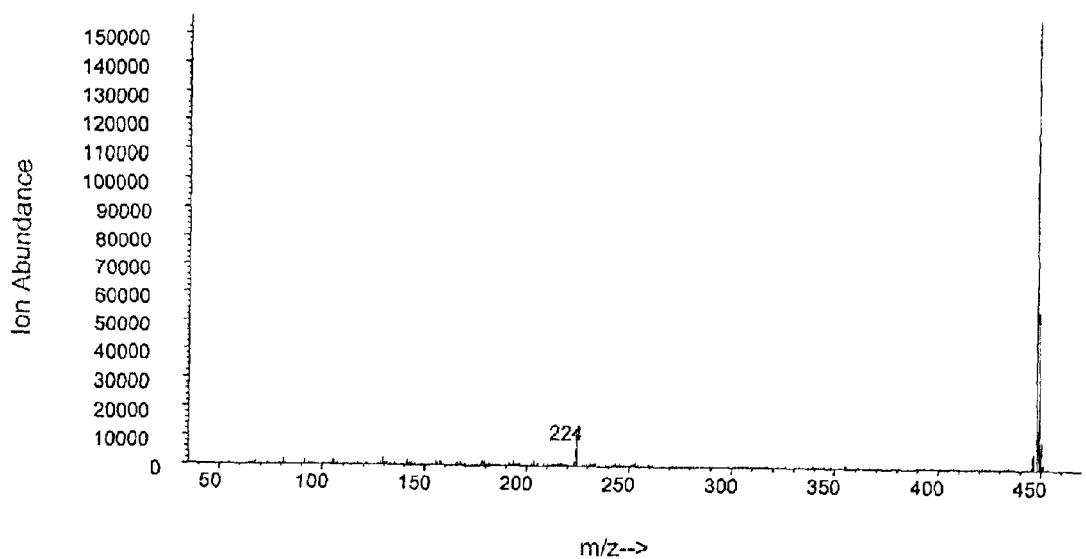
Figure 20:
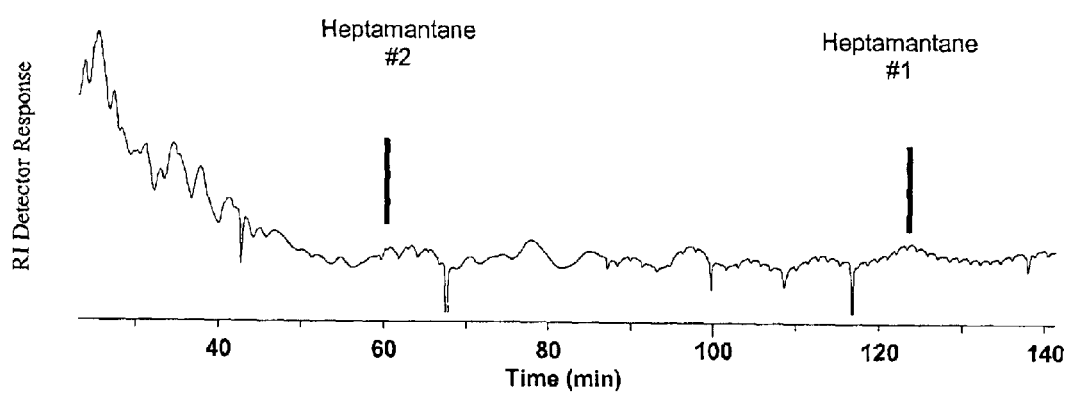
FIG. 20 illustrates results of a preparative HPLC separation of Feedstock B distillate cut pyrolysis product saturated hydrocarbon fraction showing HPLC fractions taken containing heptamantane #1 and #2 using Hypercarb columns and acetone mobile phase. Heptamantane components are numbered in order of their elution order on our GC/MS assay.
Figure 21:
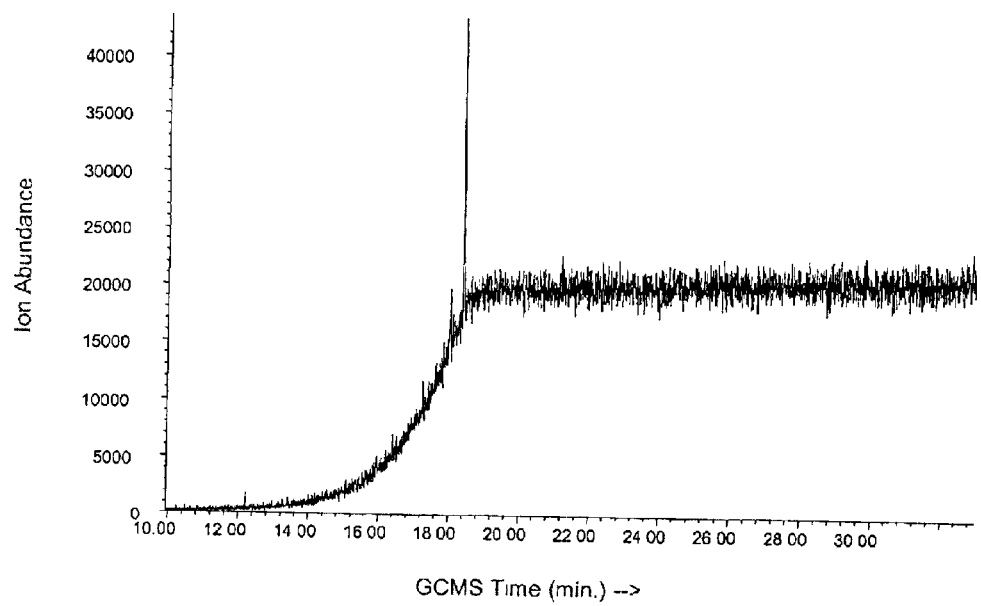
FIGS. 21(A, B) illustrates GC/MS total ion chromatogram (TIC) and mass spectrum of heptamantane #1 greatly enriched in Hypercarb HPLC fraction #55 (FIG. 20).
Figure 21:
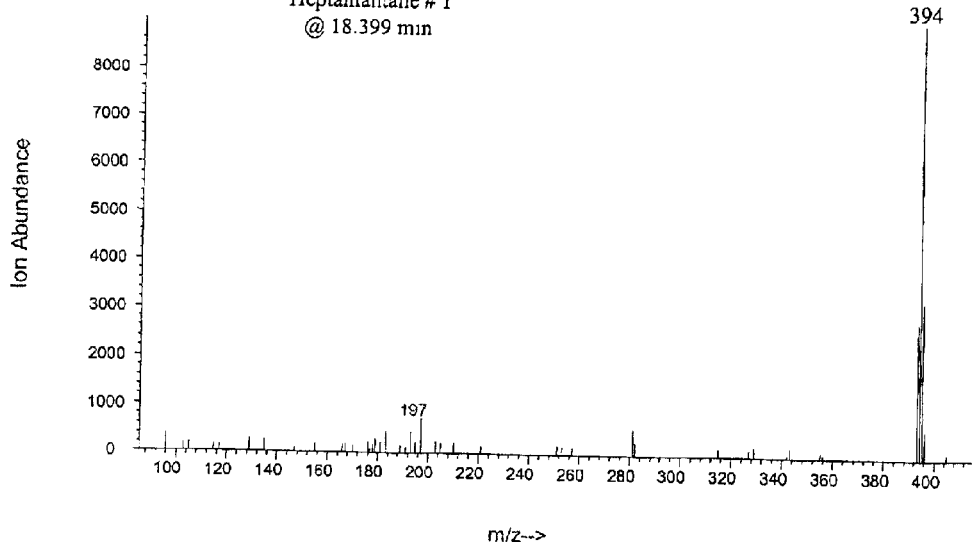

The HPLC columns used were two 50 cm×20 mm I. D. WHATMAN octadecyl silane (ODS) columns operated in series (Whatman columns are manufactured by Whatman Inc., USA). A 500 microliter sample of a solution of the cut 7 pyrolysis product saturated hydrocarbon fraction was injected into the columns. The columns were set-up using acetone at 5.00 ml/min as a mobile phase carrier. Some of the HPLC fractions reached the purity necessary for individual heptamantanes to crystallize as shown for heptamantane component # 1 in ODS HPLC fraction # 45 (FIG. 16). Others such as heptamantane component # 2 in ODS HPLC fraction # 41 (FIG. 17), heptamantane component # 9 in ODS HPLC fraction # 61 (FIG. 18), and heptamantane component #10 in ODS HPLC fraction # 87 (FIG. 19) may require further separation on HPLC systems with different selectivities. As an example, a HYPERCARB column (manufactured by Thermo Hypersil, Penn, USA) or other suitable column could be used to purify heptamantane components to concentrations necessary for them to crystallize. A preparative Hypercarb HPLC run of Feedstock B distillate cut 7 pyrolysis product saturated hydrocarbon fraction was performed and the HPLC chromatogram recorded using a differential refractometer: results are shown in FIG. 20. Fractions containing heptamantane components #1 and #2 where taken during the run as indicated in FIG. 20. The ODS and Hypercarb HPLC systems show different selectivities for the heptamantanes. Some of the Hypercarb preparative HPLC fractions reached the purity necessary for individual heptamantane components to crystallize as shown for heptamantane component # 1 in Hypercarb HPLC fraction # 55 (FIG. 21). The higher diamondoids in various HPLC fractions could be separated using further chromatographic techniques including preparative gas chromatography, additional HPLC runs using columns of different selectivity as outlined below. Additionally other techniques known in the crystallization art could be utilized including but not limited to fractional sublimation, progressive recrystalization or zone refining.

Example 4

Purification of Single Heptamantane Isomers

Figure 17:
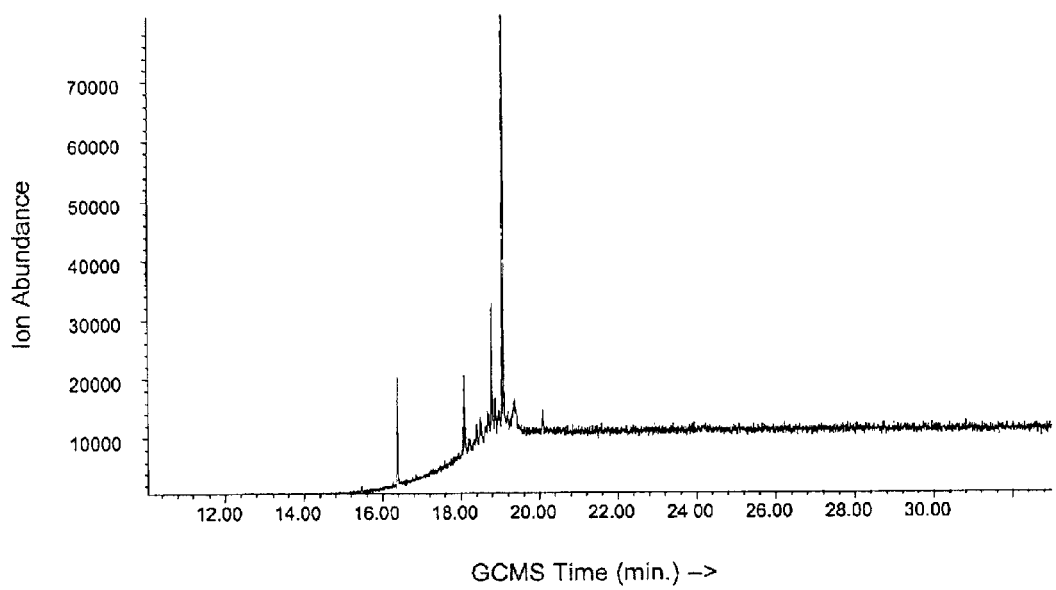
FIGS. 17(A, B) illustrates GC/MS total ion chromatogram (TIC) and mass spectrum of heptamantane component #2 in ODS HPLC fraction 41 (FIG. 15).
Figure 17:
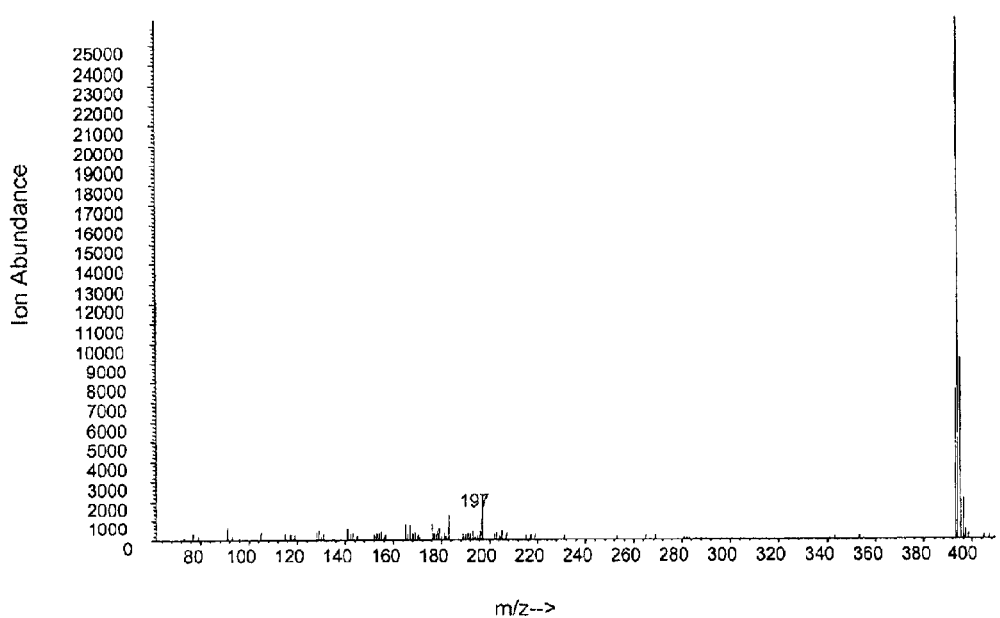

As shown in Example 3, heptamantanes can be isolated in high purity by using HPLC methods. In this example, HPLC columns of different selectivities were used in succession to isolate individual heptamantane components. FIG. 15 shows results of a preparative separation of the heptamantanes from distillation cut 7-pyrolysis product saturated hydrocarbon fraction using an octadecyl silane (ODS) HPLC column with acetone as a mobile phase. This first HPLC system consisted of two Whatman M20 10/50 ODS columns operated in series using acetone as mobile phase at 5.00 mL/min. The detector used was a differential refractometer. From this HPLC run, (FIG. 15) fraction 41 was taken for further purification on a second HPLC system. This fraction 41 contained heptamantane component #2 and various impurities (FIG. 17).

Further purification of ODS HPLC fraction 41 was achieved using a HYPERCARB stationary phase HPLC column having a different selectivity in the separation of various heptamantanes than the ODS column discussed above. FIG. 20 shows a preparative Hypercarb HPLC run for distillation cut 7 pyrolysis product saturated hydrocarbon indicating elution times of the individual heptamantane components #1 and #2 as noted on the chart (FIG. 20). By relying on the different elution order/times of these HPLC systems, fractions showing impurities or co-elution of higher diamondoids can be further purified by using an appropriate column with different selectivity.

Using this method, a 50 microliter sample of approximately 1 mg of ODS HPLC fraction 41 in acetone was injected into the Hypercarb column, 10 mm I.D.×250 mm, operated using acetone at 3.00 mL/min as mobile phase (@480 psi), and using a differential refractometer detector.

Figure 22:
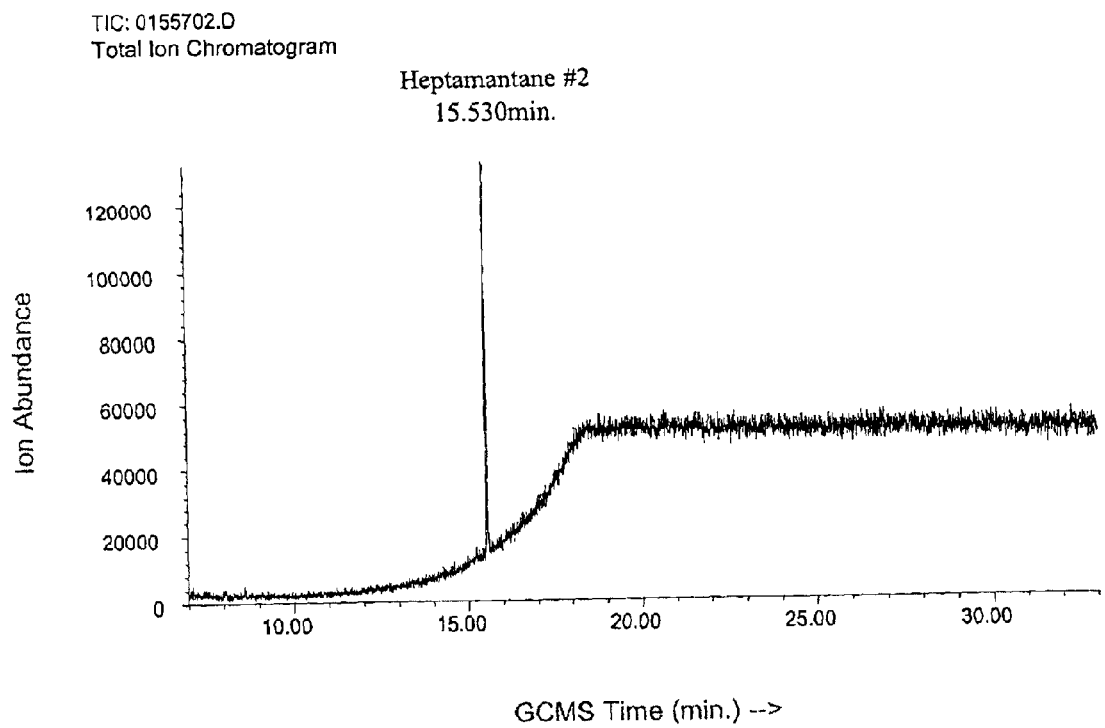
FIGS. 22(A, B) illustrates GC/MS total ion chromatogram (TIC) and mass spectrum of heptamantane #2 isolated using two different HPLC columns. Heptamantane #2 was isolated from ODS HPLC fraction #41 (FIG. 17) using the Hypercarb HPLC system.
Figure 22:
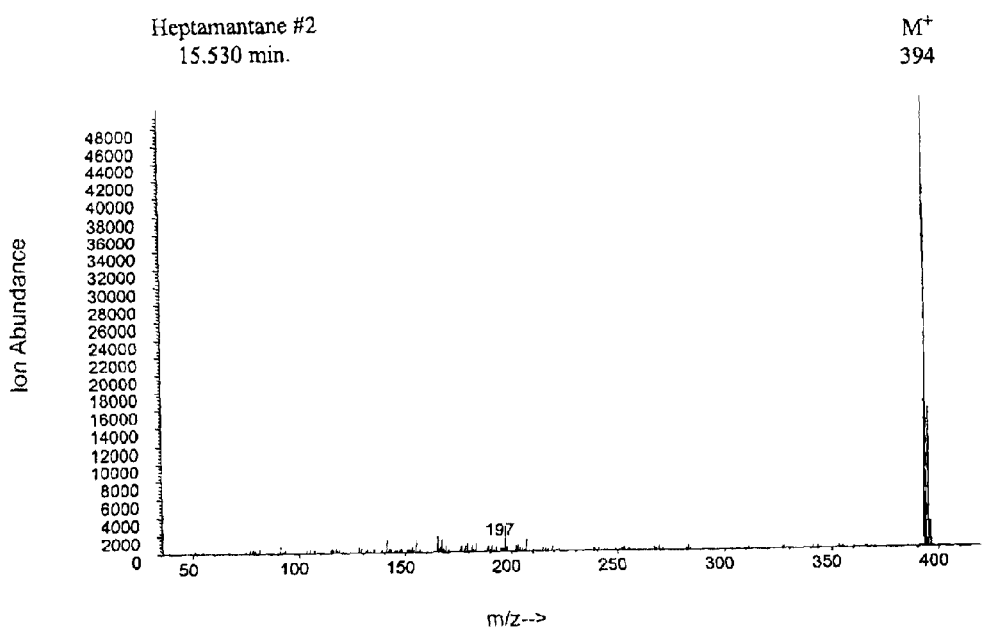

Using FIG. 20 as a guide, appropriate Hypercarb HPLC fractions were taken from this HPLC run thus obtaining high purity heptamantane component #2 demonstrated in FIG. 22. Other ODS HPLC fractions and Hypercarb HPLC cut points could be used to isolate the remaining heptamantanes. The ODS and Hypercarb columns can also be used in reverse order for this isolation. FIG. 22 shows the GC/MS total ion chromatogram (TIC) of the heptamantane component #2 containing Hypercarb HPLC fraction. The lower half of FIG. 22 illustrates the mass spectrum of the GC/MS peak, demonstrating the high purity of the isolated heptamantane #2.

Figure 23:
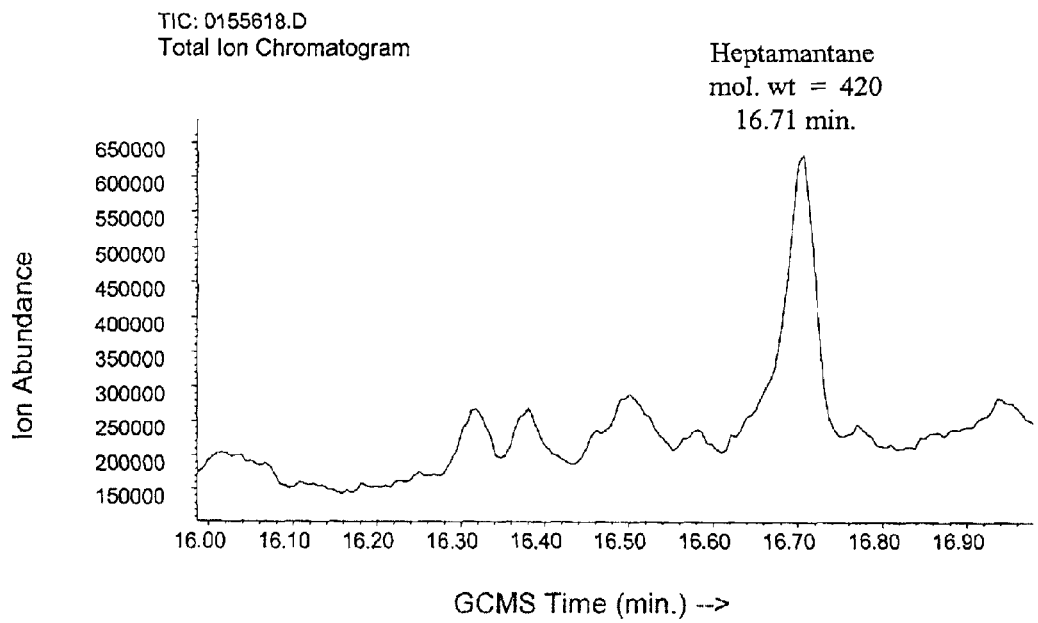
FIGS. 23 (A, B) illustrates GC/MS reconstructed ion chromatogram m/z 420 and mass spectrum of a partially condensed heptamantane component (mol. wt. 420) in the ODS HPLC fraction # 61.
Figure 23:
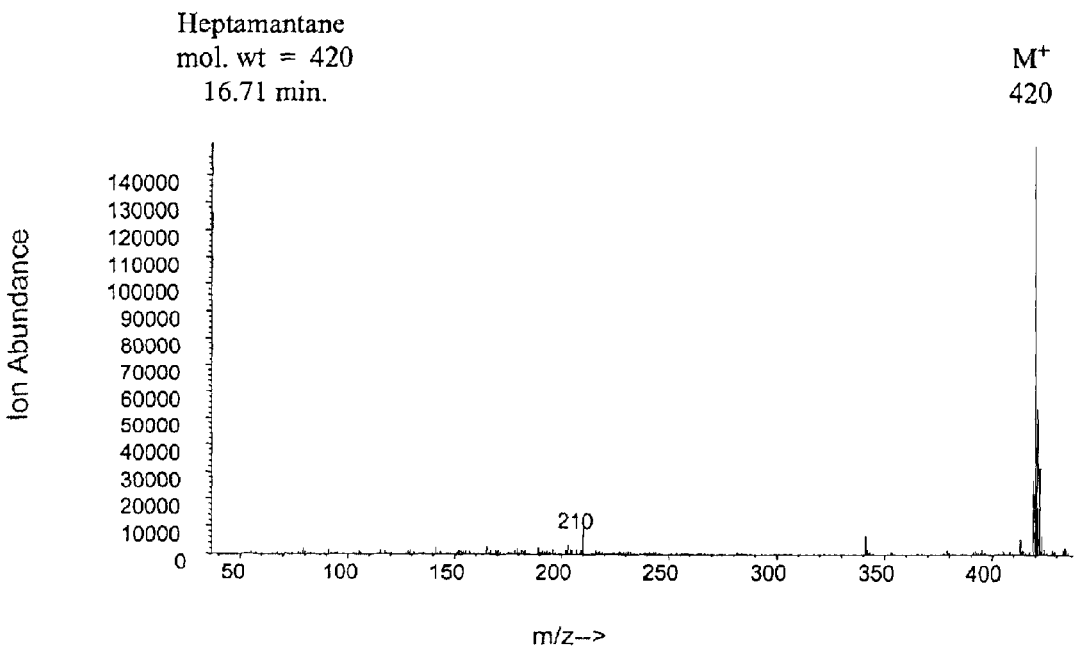

As indicated in FIG. 15, the various remaining ODS HPLC fractions containing other heptamantanes could be separated in the same way. By using similar methodology as above, i.e. fractionating heptamantane containing ODS fractions using the Hypercarb or other suitable column and collecting at corresponding elution times can lead to the isolation of the remaining heptamantanes in high purity. This is also true of the heptamantanes with molecular weights of 420 and 434, that are in much lower abundance in our feedstocks than heptamantane components showing molecular weights of 394 and 448. A heptamantane component of molecular weight 420 shows up in ODS HPLC fraction #61 (FIG. 23A) with a very strong molecular ion in the mass spectrum (in this case m/z 420, FIG. 23B) for the m/z 420 component running at 16.71 min. The mass spectrum, with its prominent molecular ion and low number and abundance of fragments is characteristic of a diamondoid component.

The enantiomeric heptamantanes are not resolved in GS/MS and therefore, these enantiomeric pairs are referenced within a single number. These enantiomers can be isolated by chiral separation methods.

Figure 25:
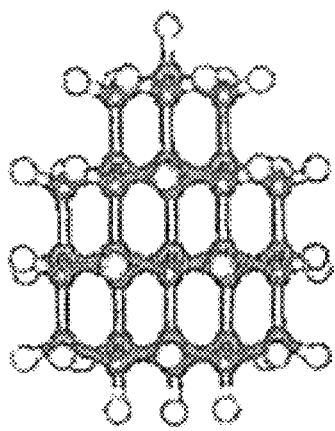
FIGS. 25 through 120 illustrate the structures with views into various diamond crystal lattice planes for each of the mol. wt. 394 and 448 heptamantane structures.
Figure 25:
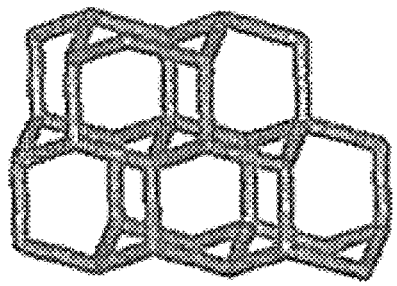
Figure 25:
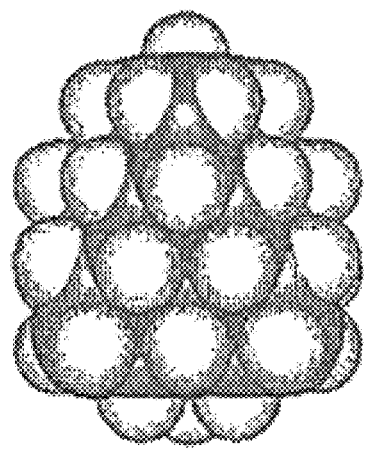
Figure 26:
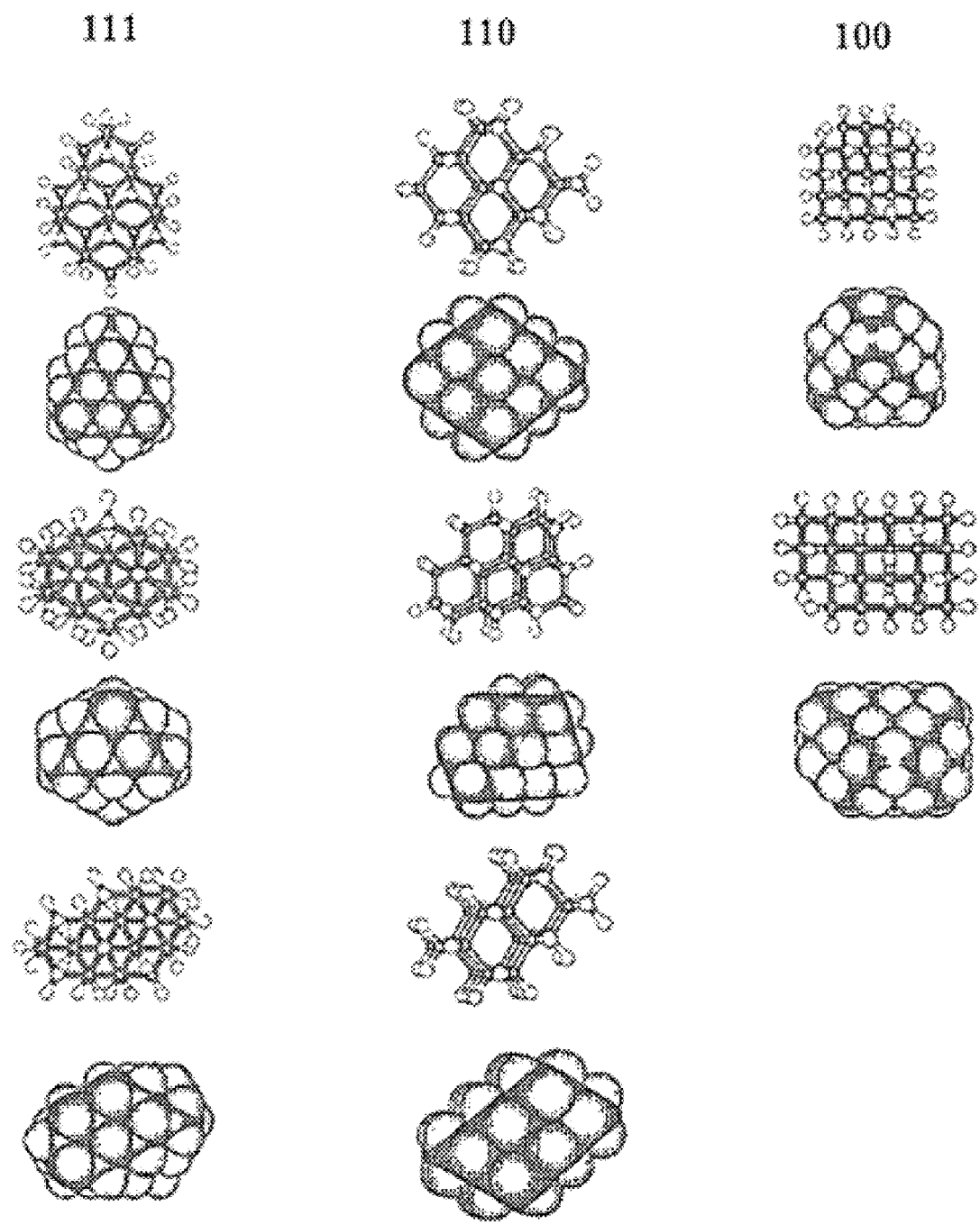
Figure 27:
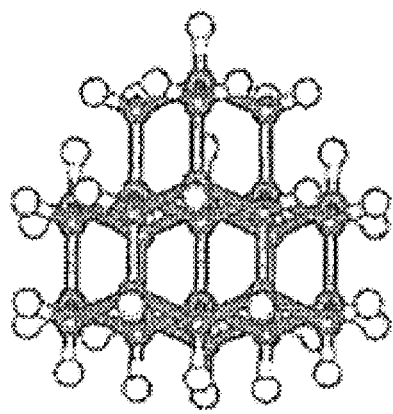
Figure 27:
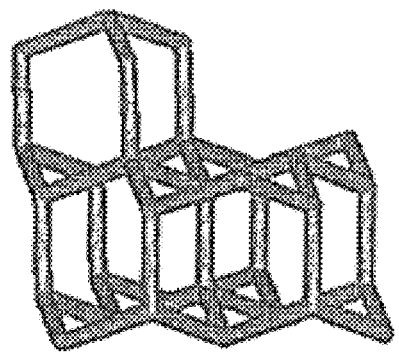
Figure 27:
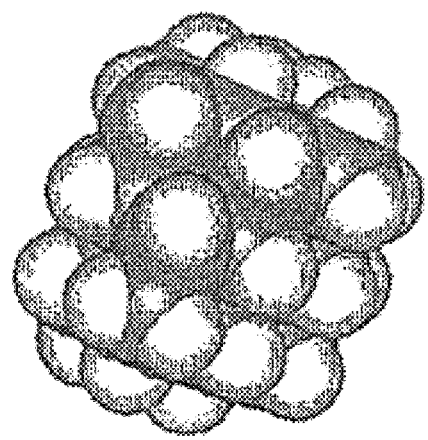
Figure 28:
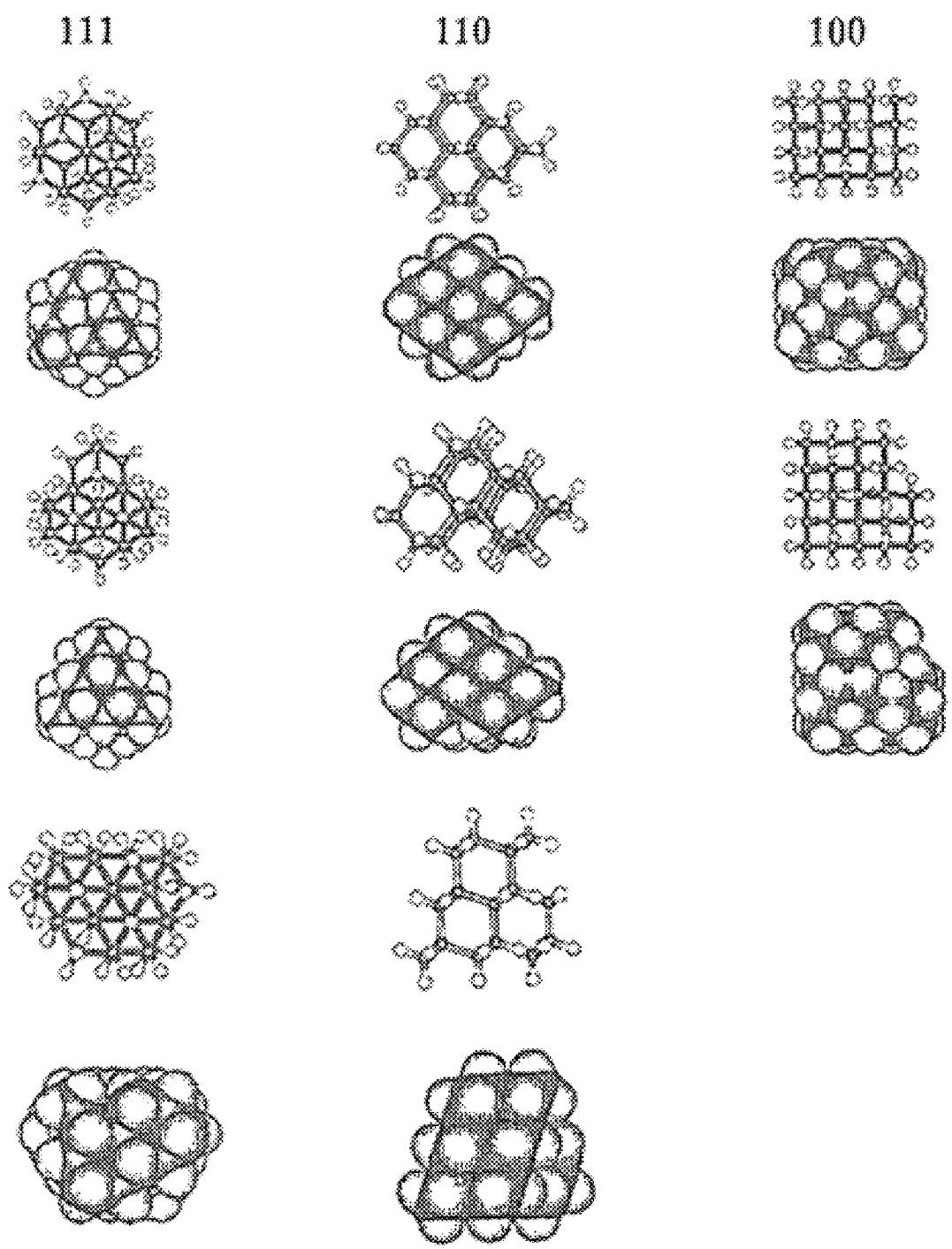
Figure 29:
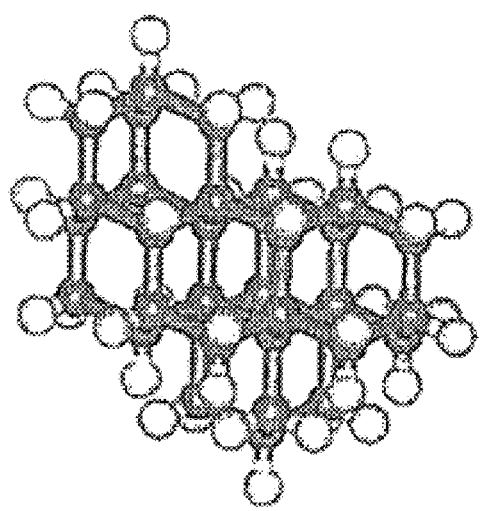
Figure 29:
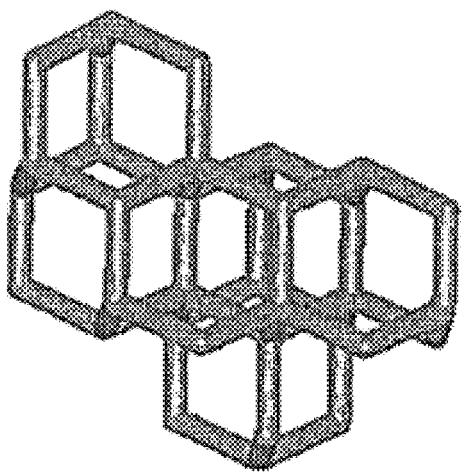
Figure 29:
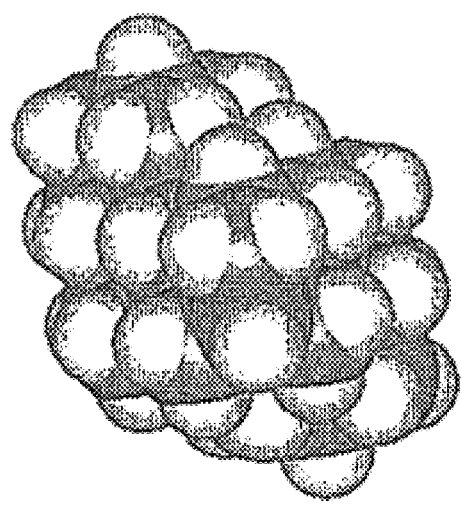
Figure 30:
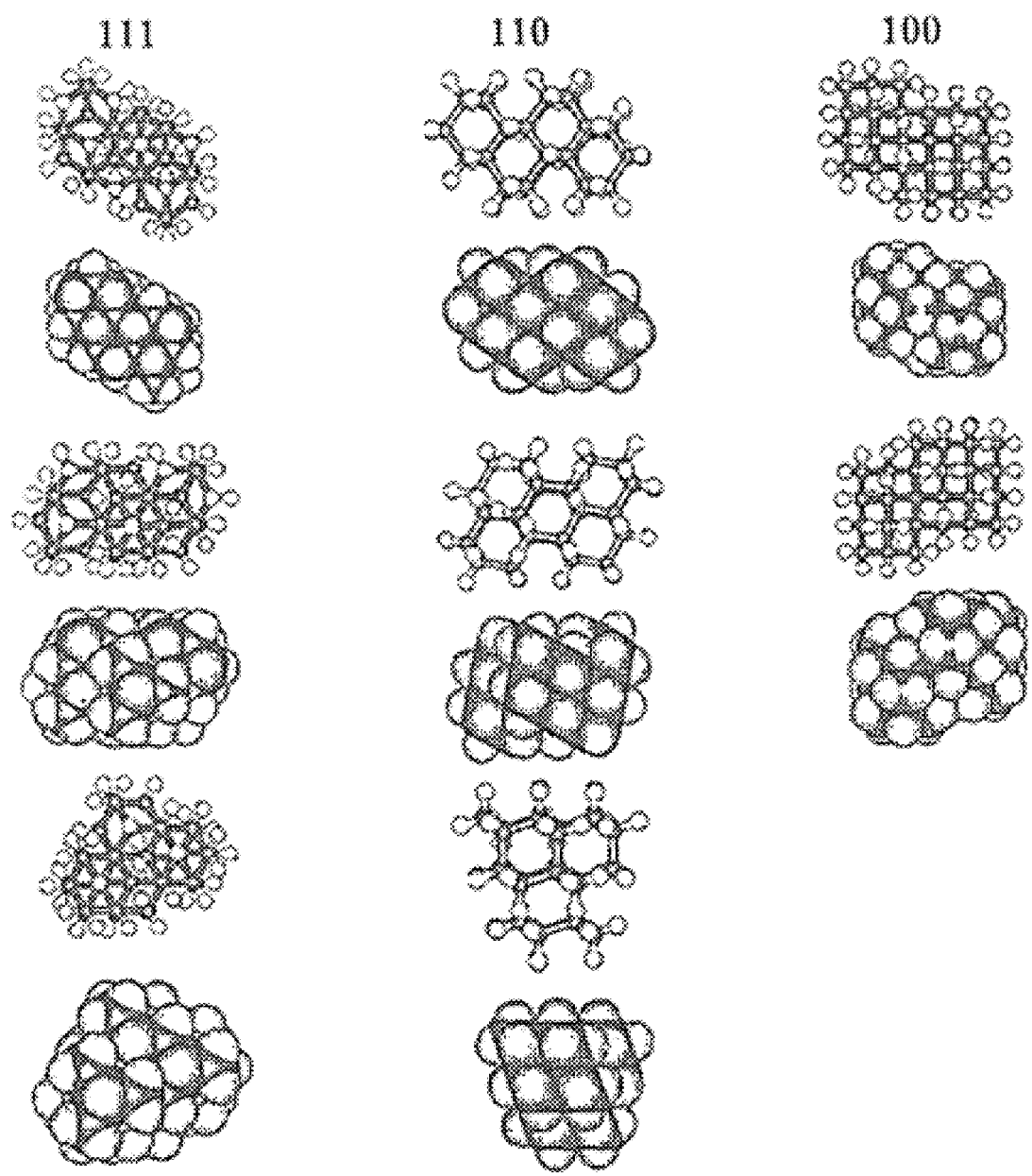
Figure 31:
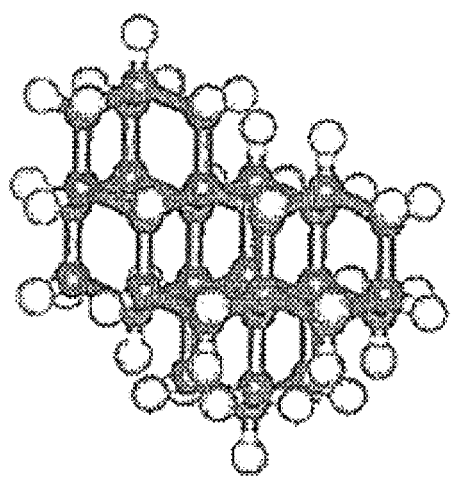
Figure 31:
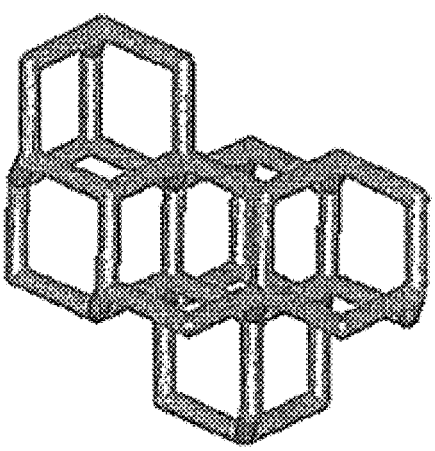
Figure 31:
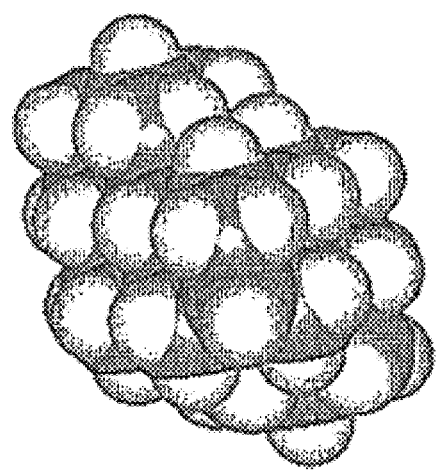
Figure 32:
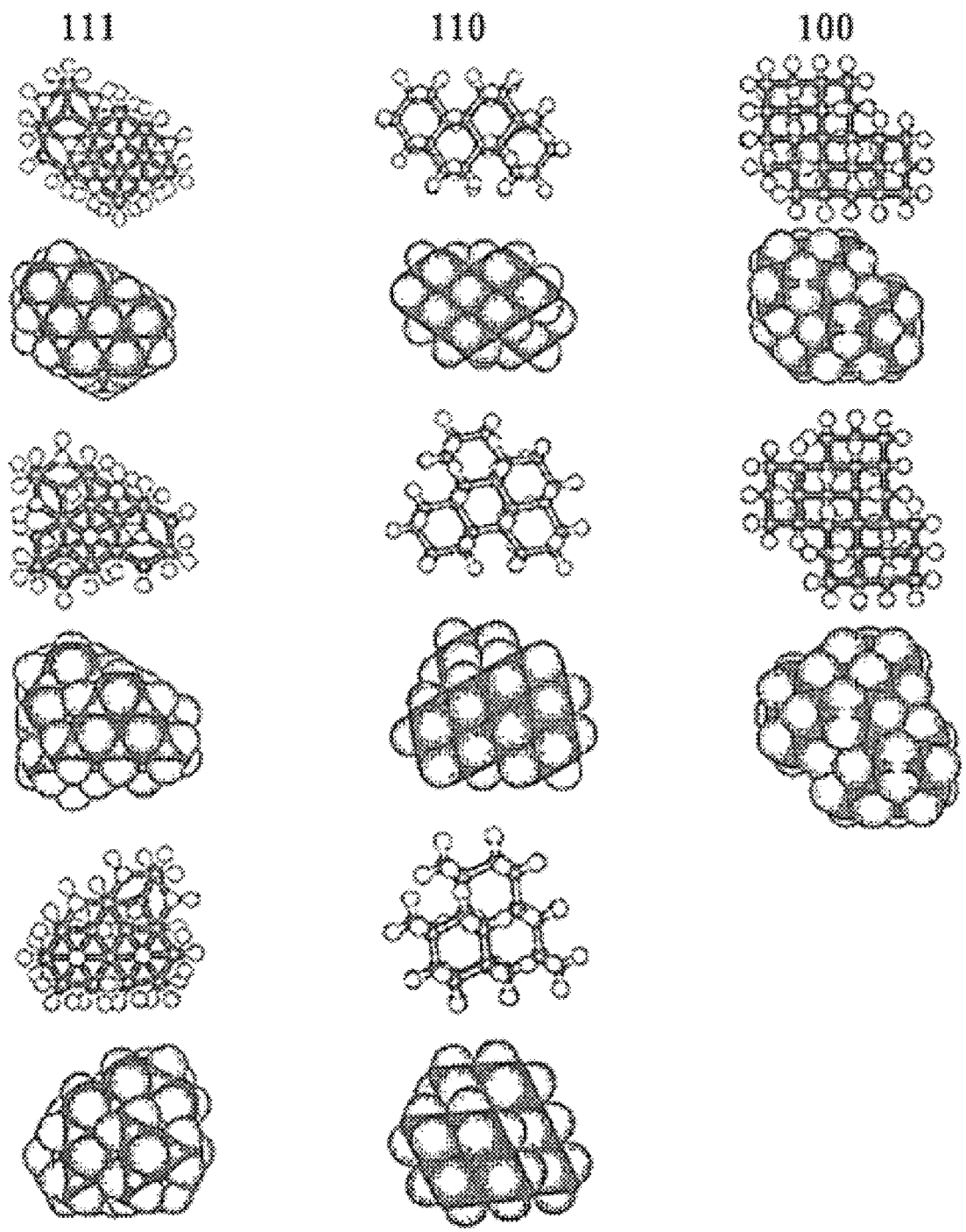
Figure 33:
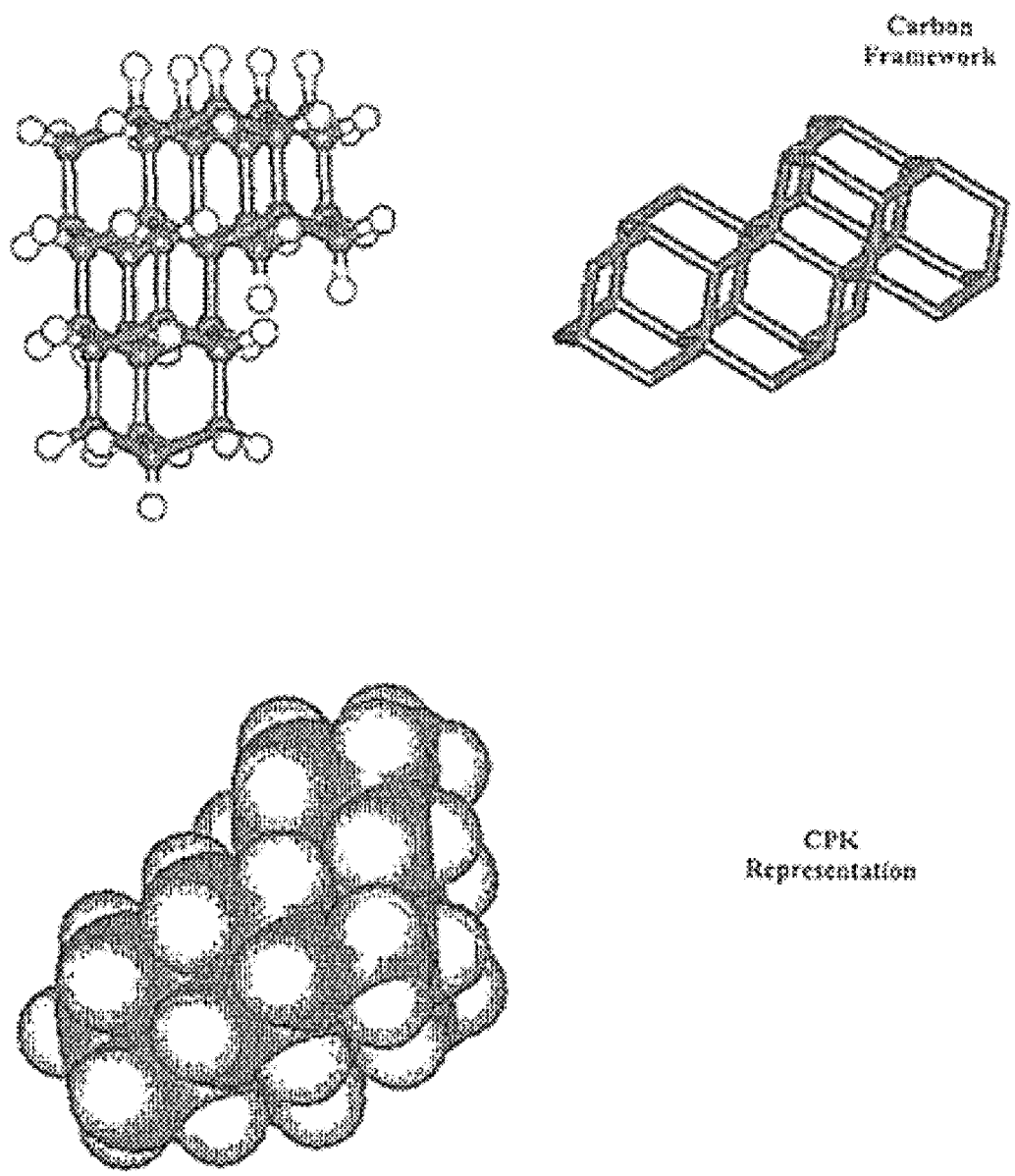
Figure 34:
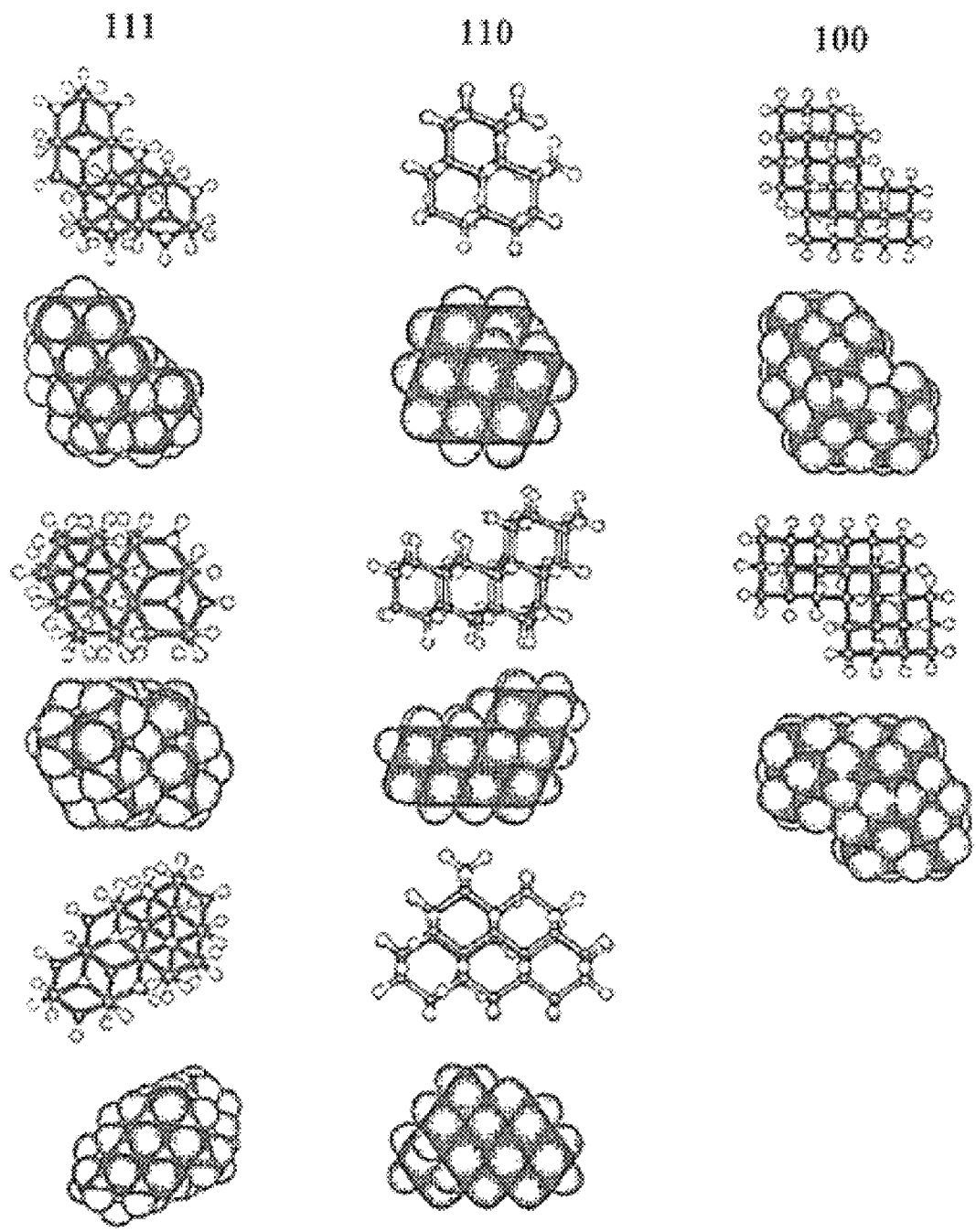
Figure 35:
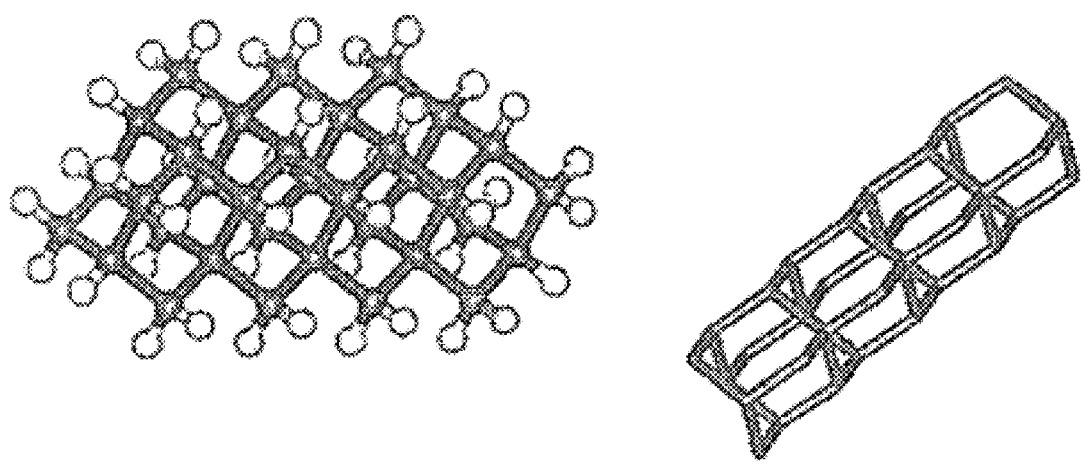
Figure 35:
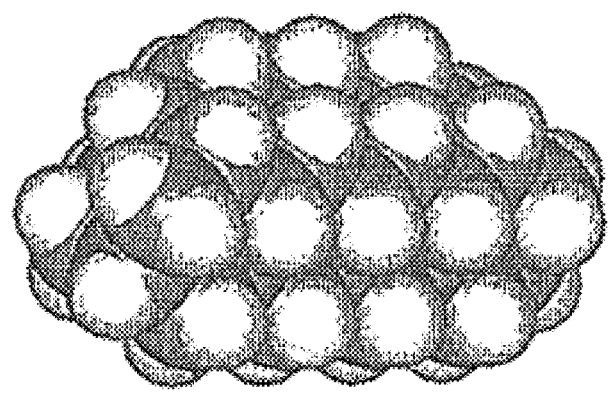
Figure 36:
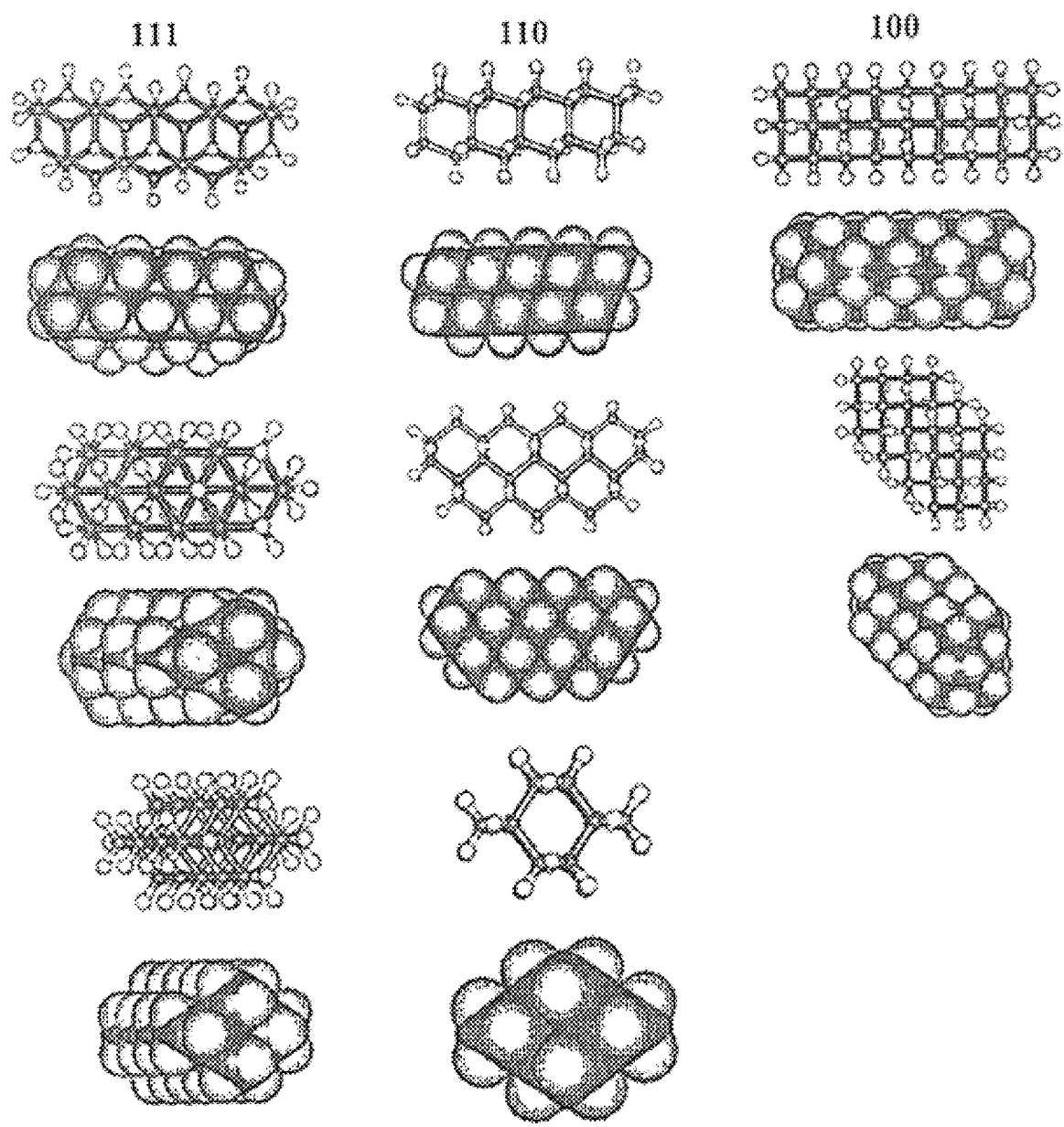
Figure 37:
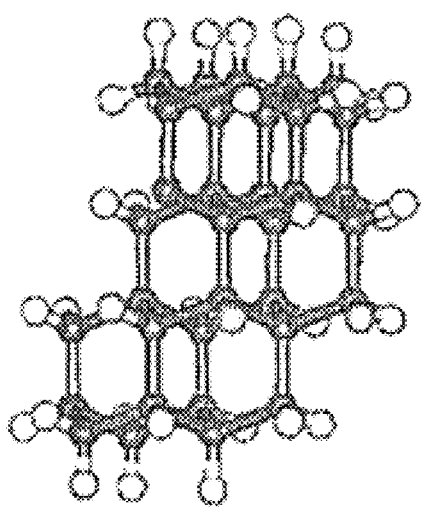
Figure 37:
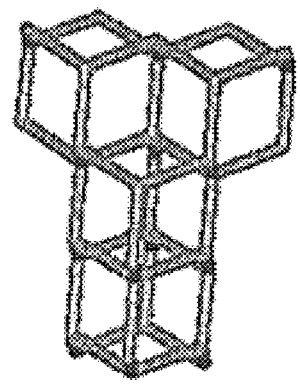
Figure 37:
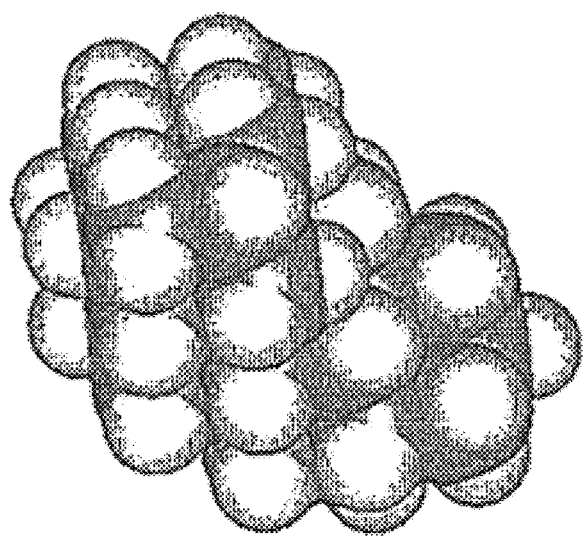
Figure 38:
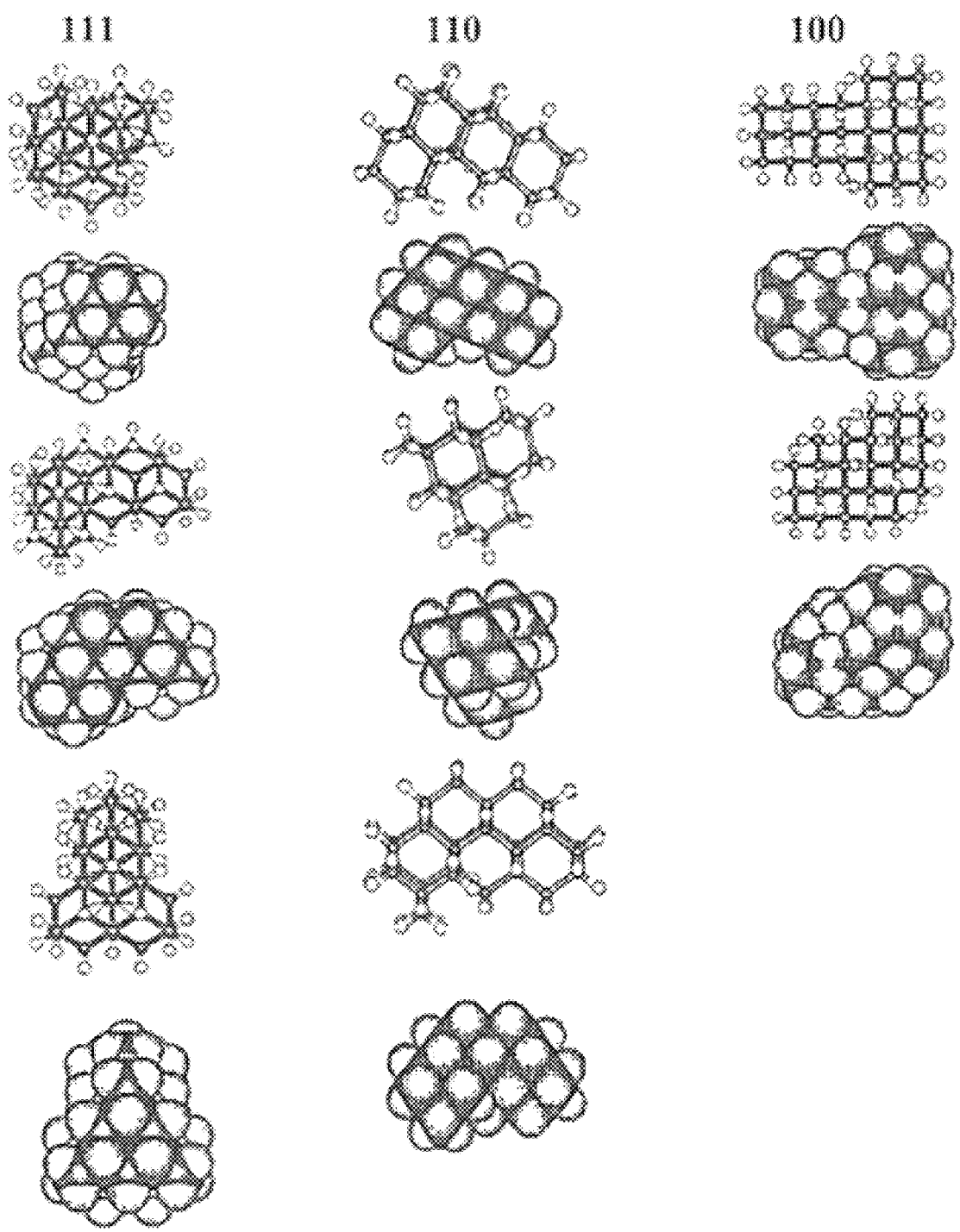
Figure 39:
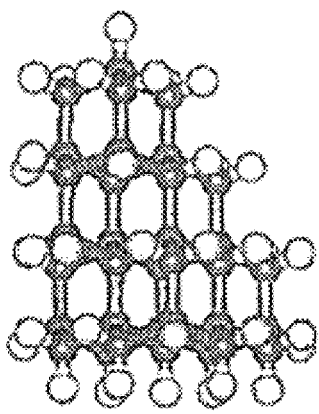
Figure 39:
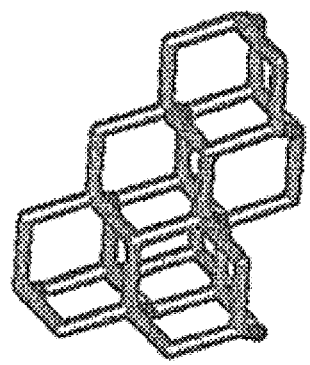
Figure 39:
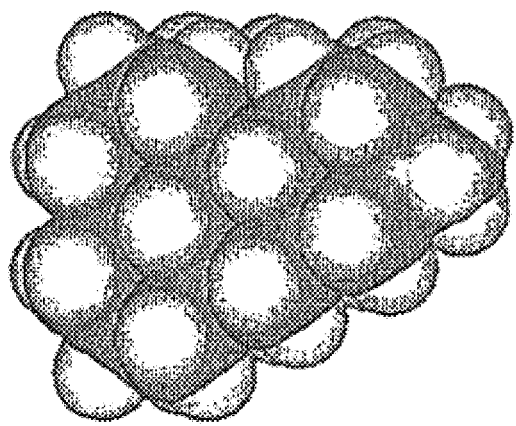
Figure 40:
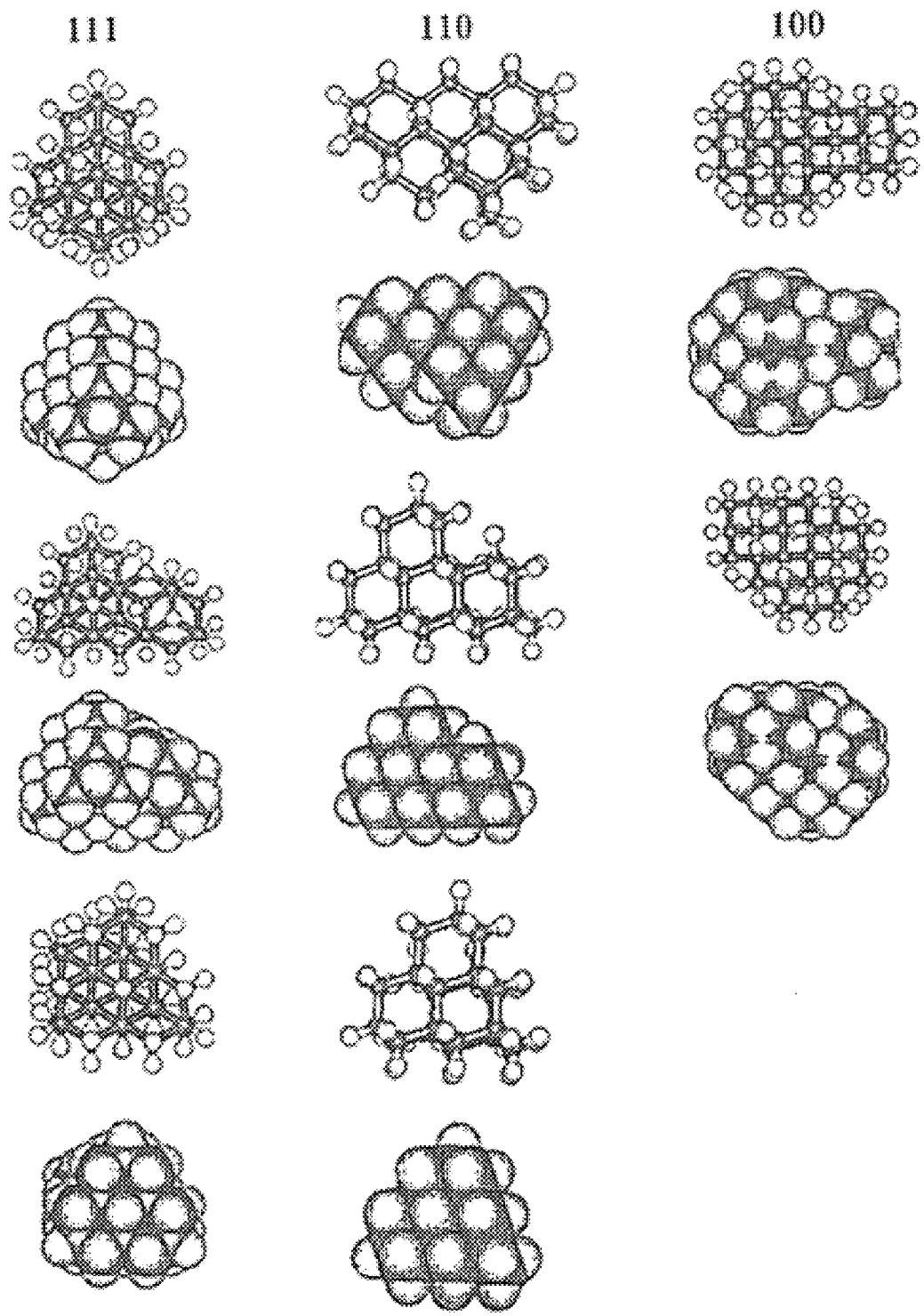
Figure 41:
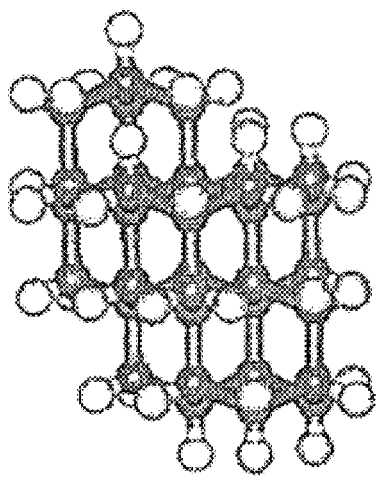
Figure 41:
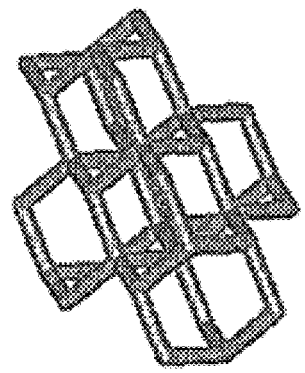
Figure 41:
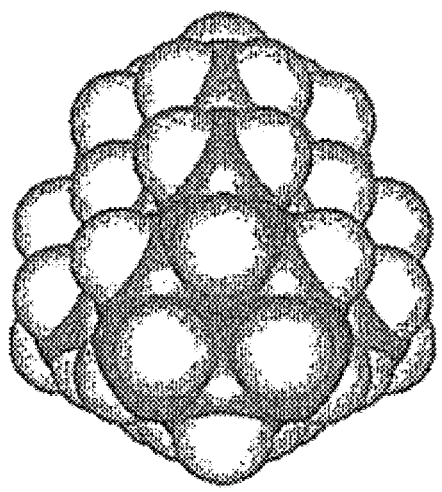
Figure 42:
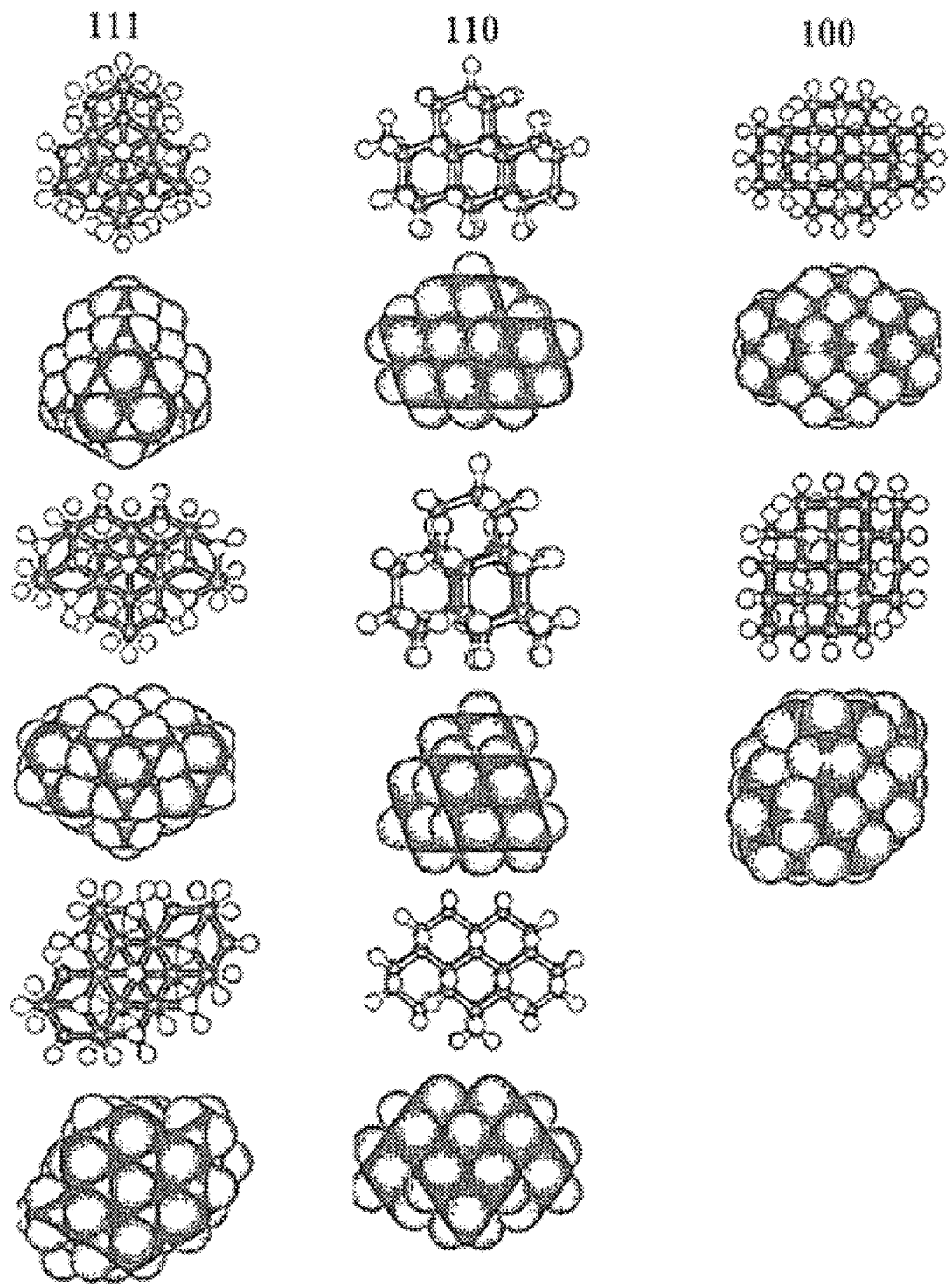
Figure 43:
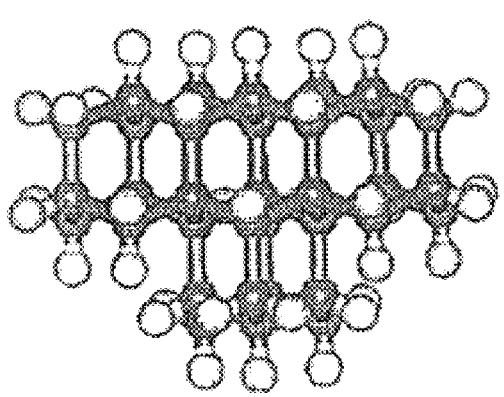
Figure 43:
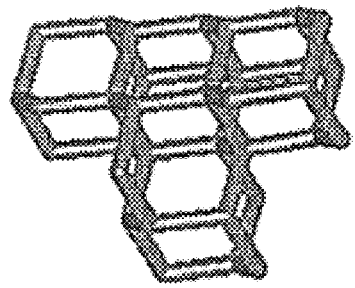
Figure 43:
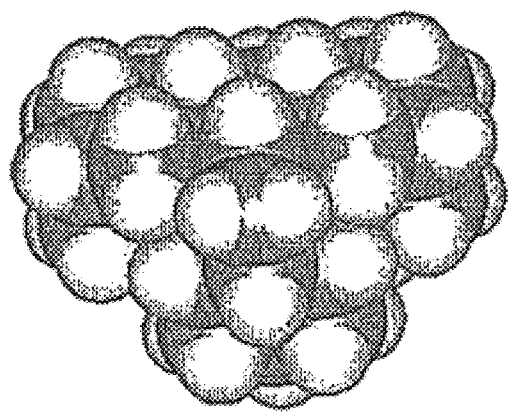
Figure 44:
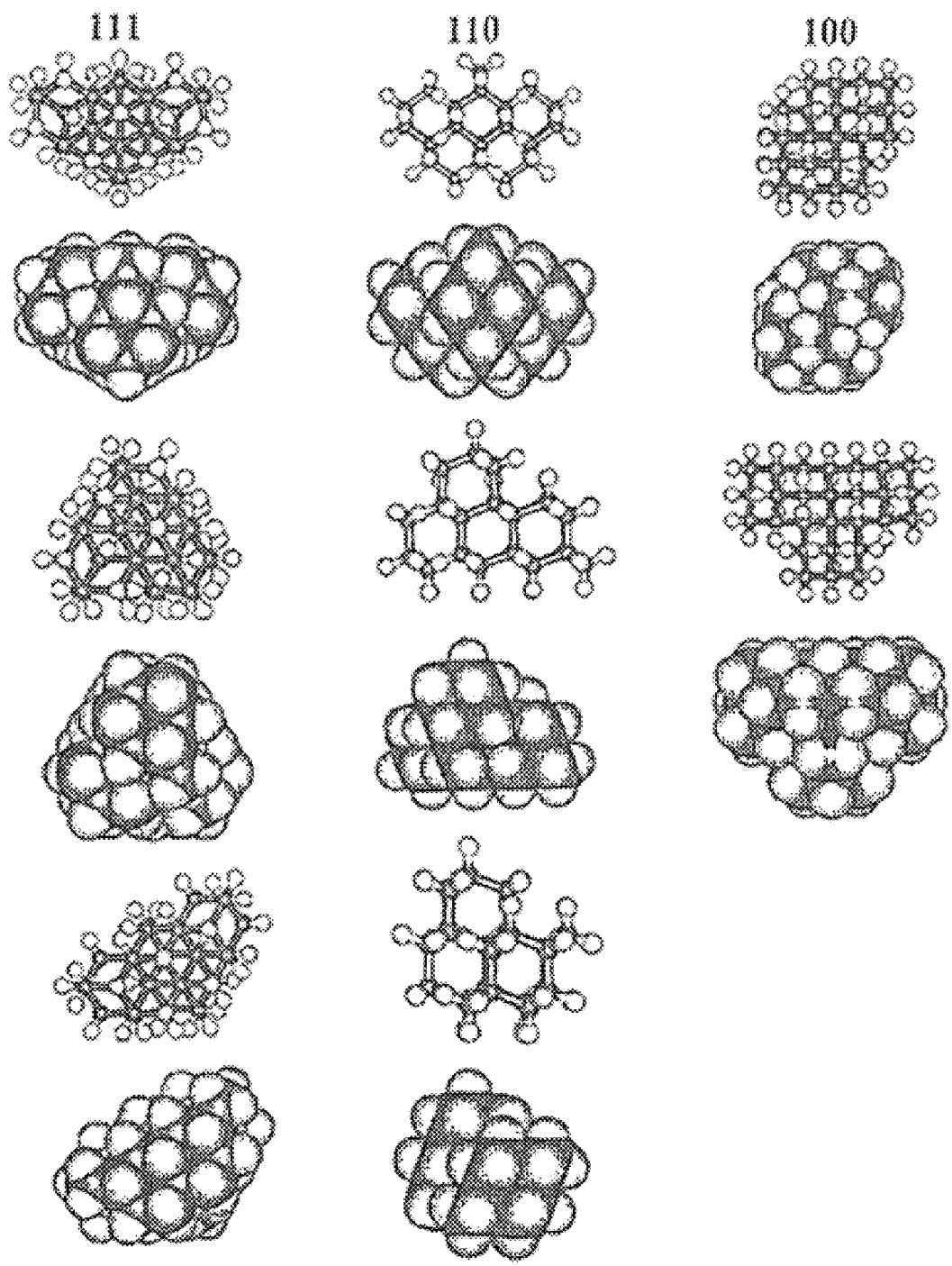
Figure 45:
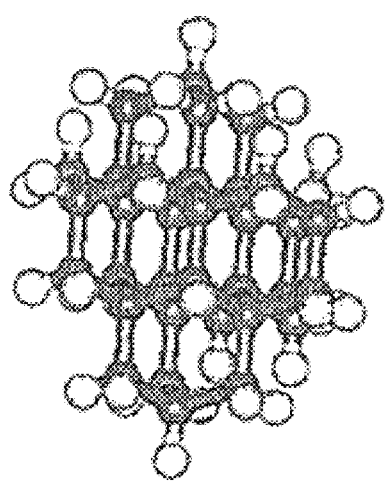
Figure 45:
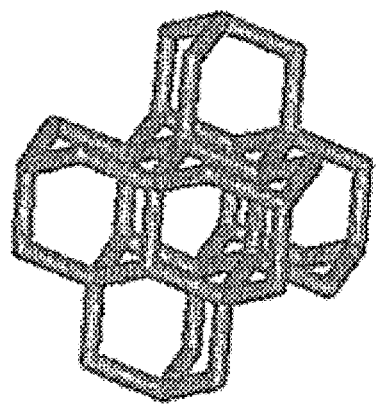
Figure 45:
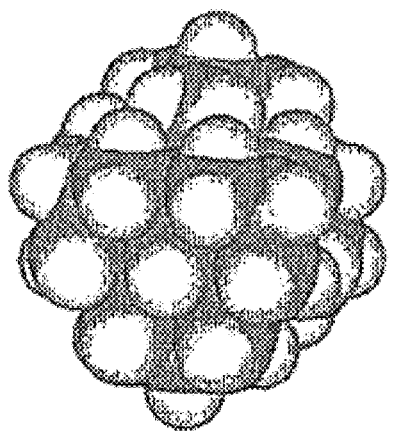
Figure 46:
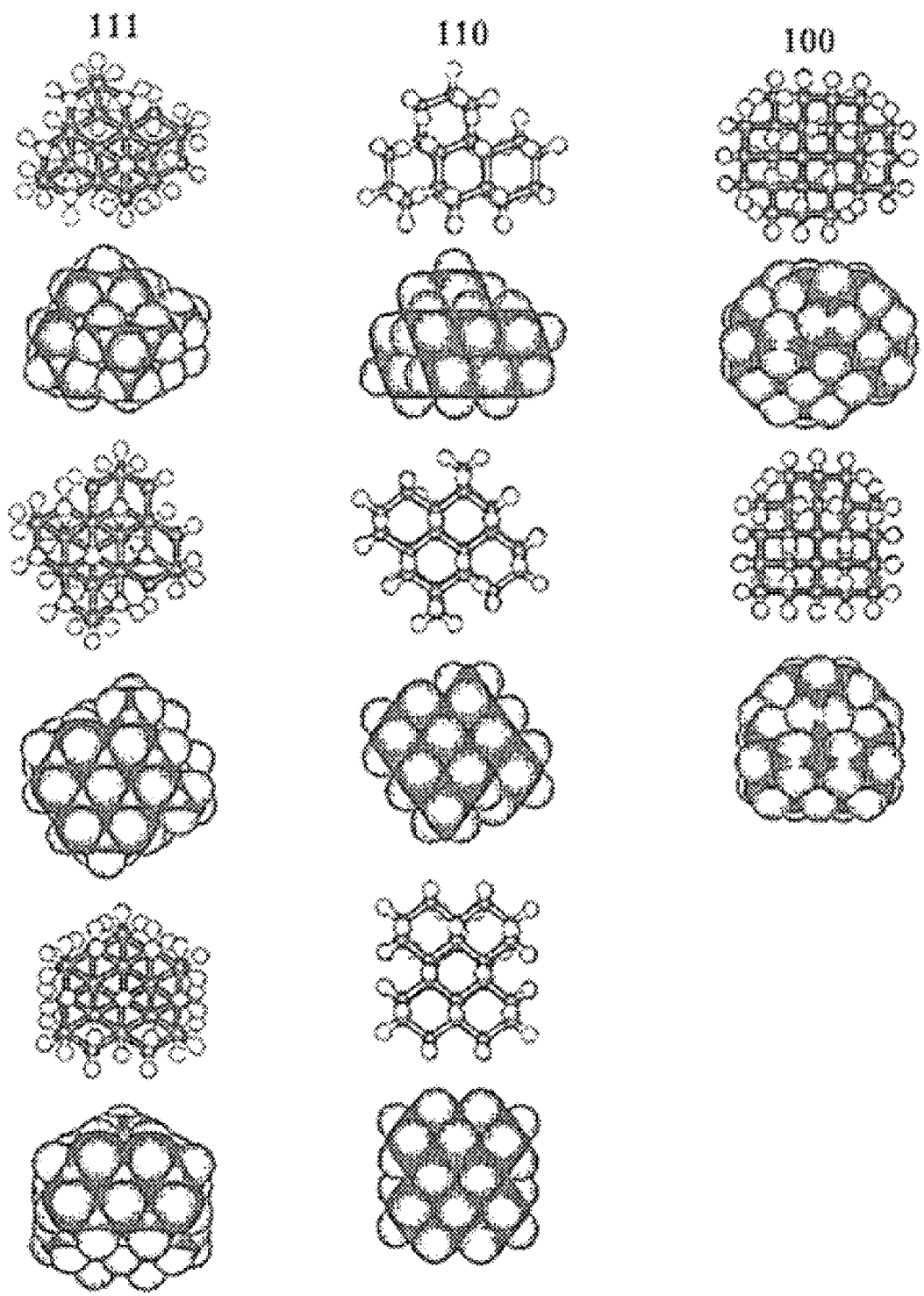
Figure 47:
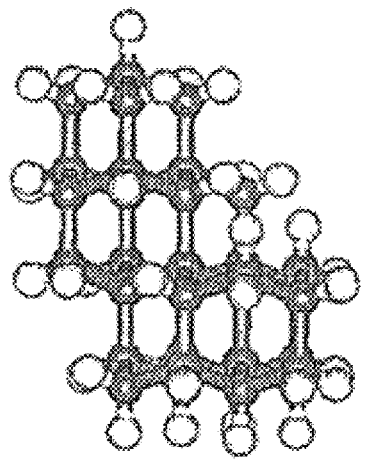
Figure 47:
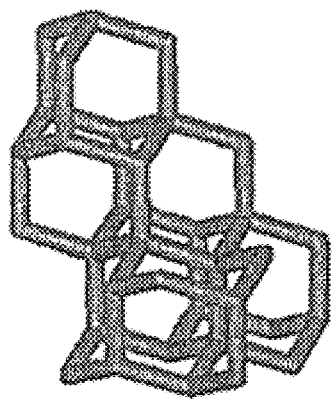
Figure 47:
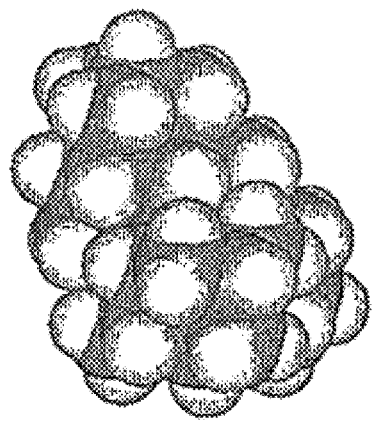
Figure 48:
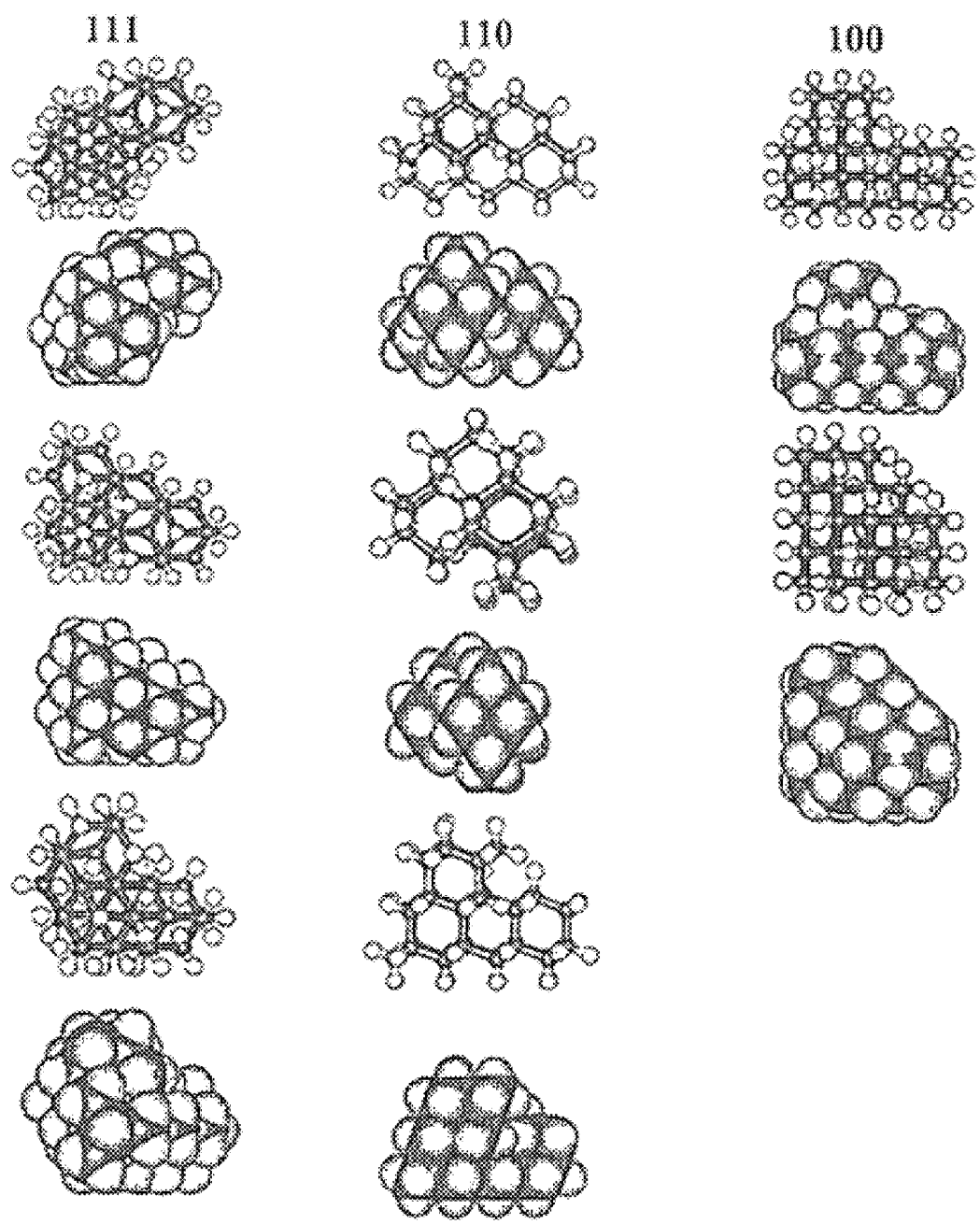
Figure 49:
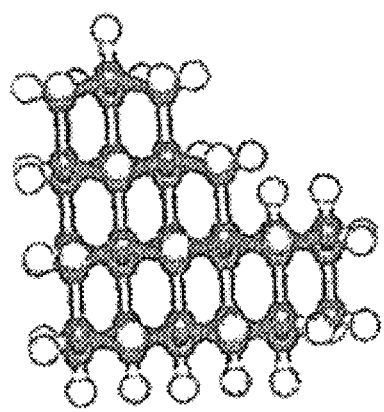
Figure 49:
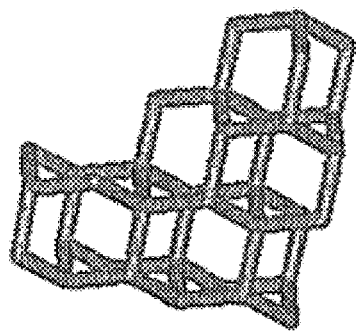
Figure 49:
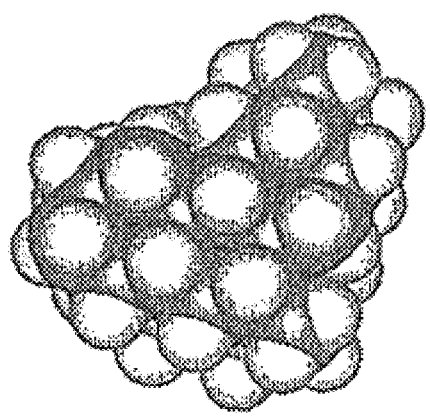
Figure 50:
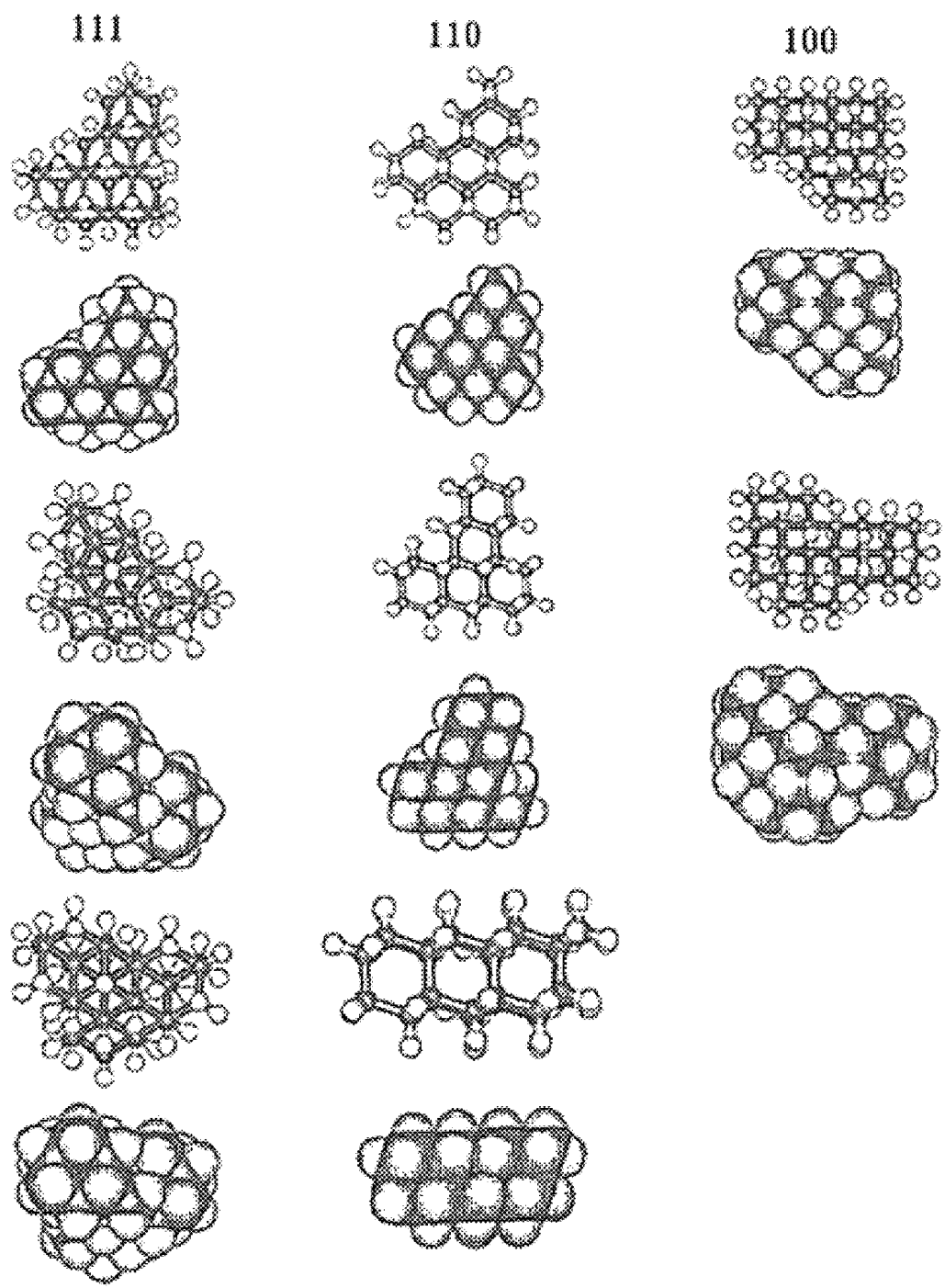
Figure 51:
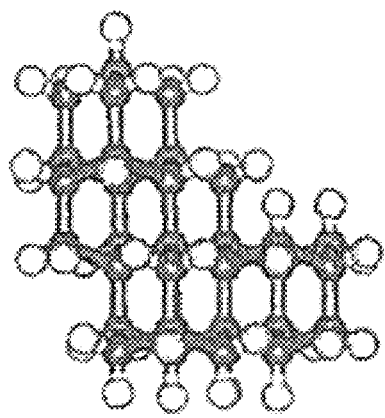
Figure 51:
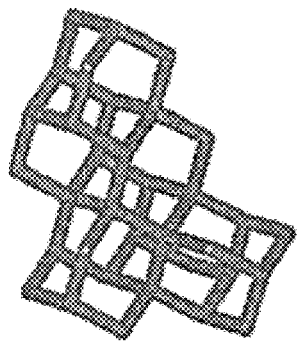
Figure 51:
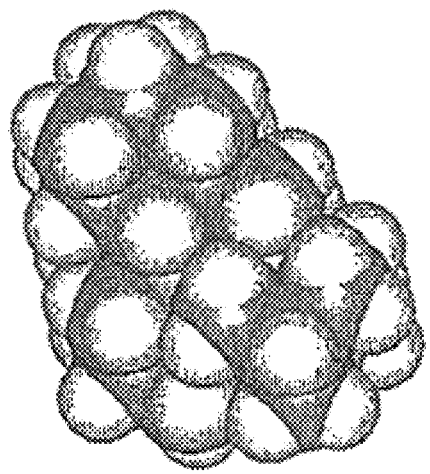
Figure 52:
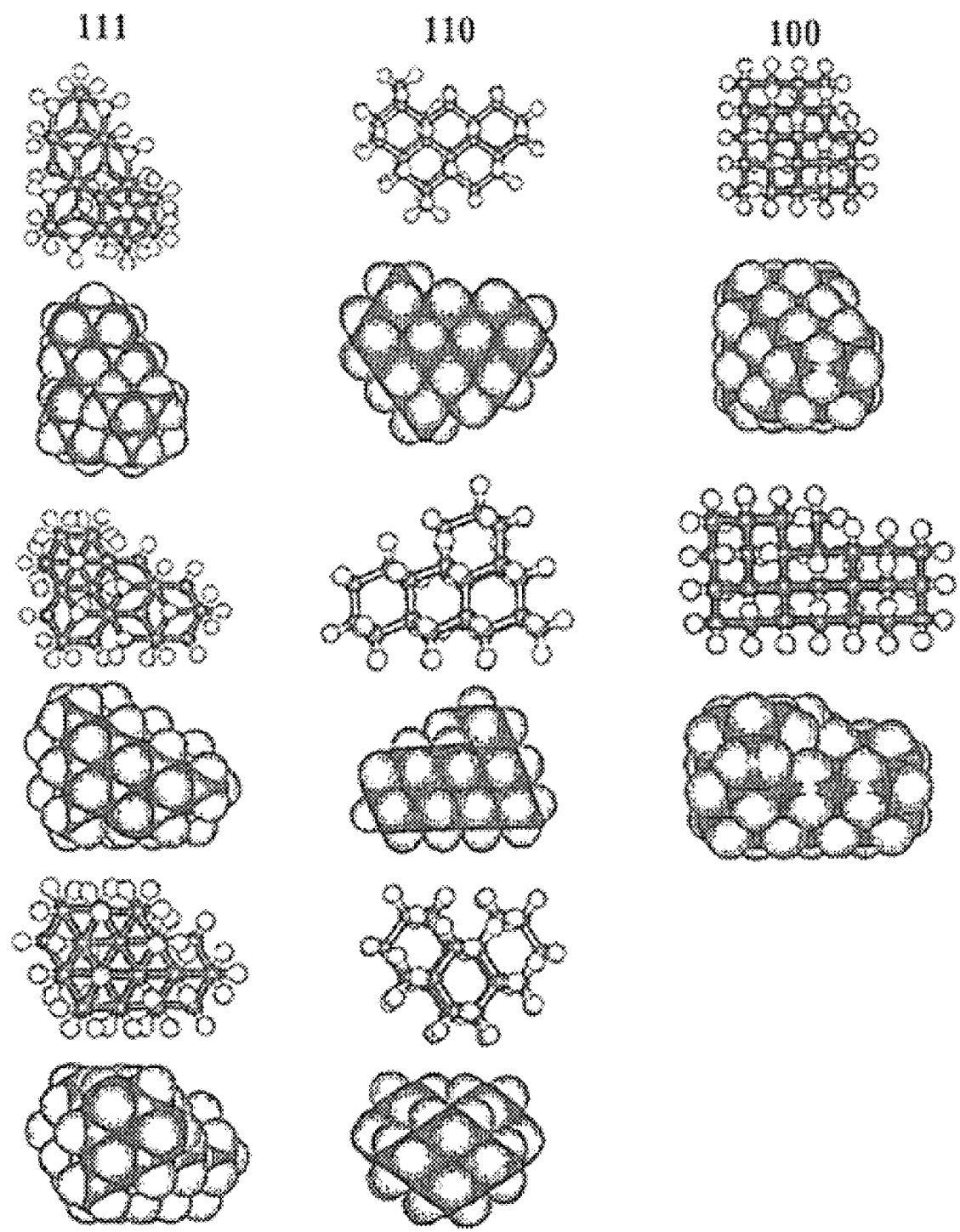
Figure 53:
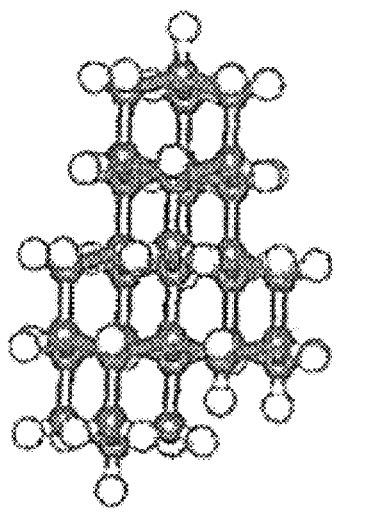
Figure 53:
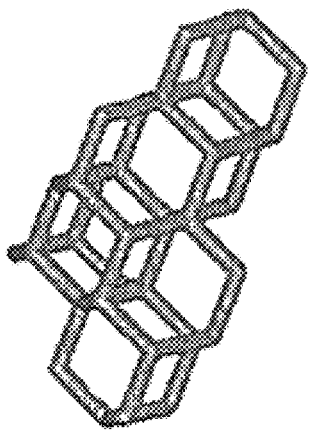
Figure 53:
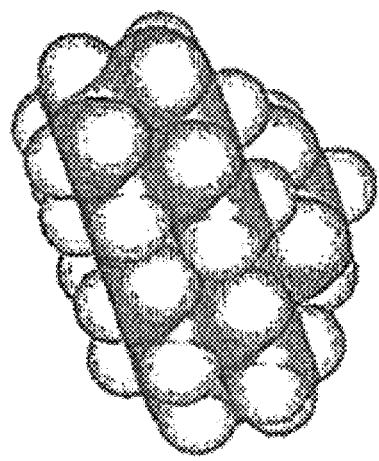
Figure 54:
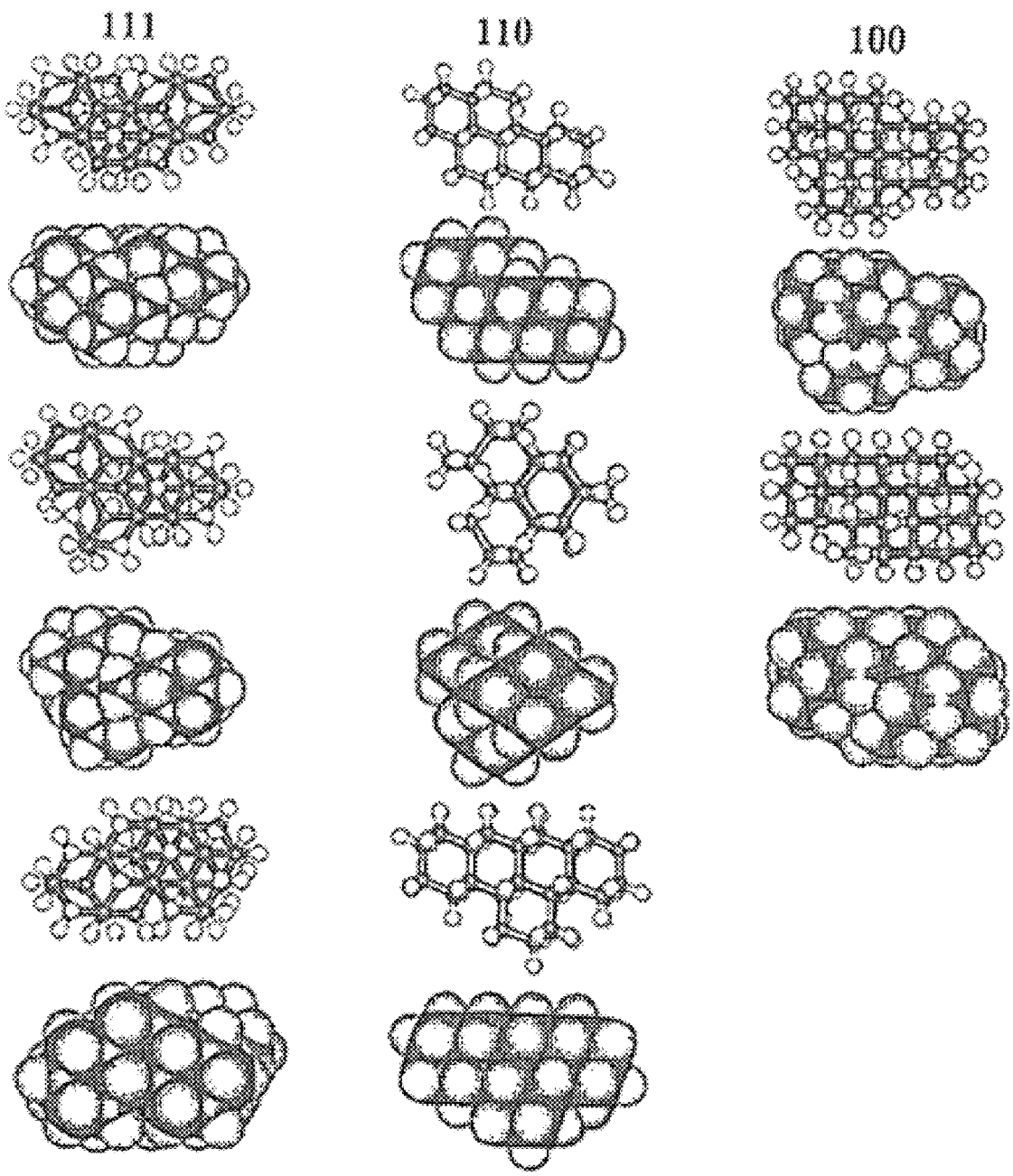
Figure 55:
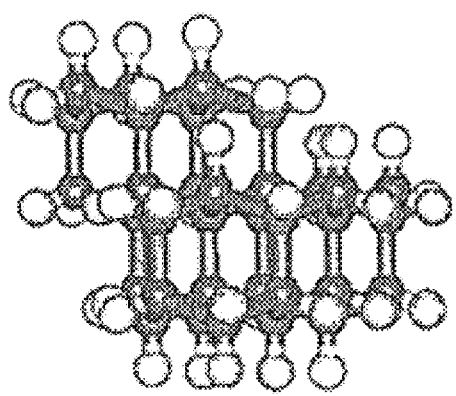
Figure 55:
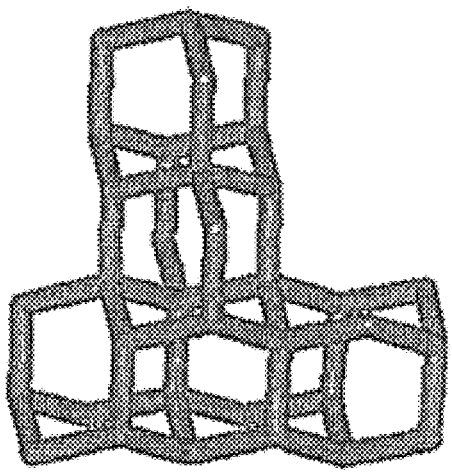
Figure 55:
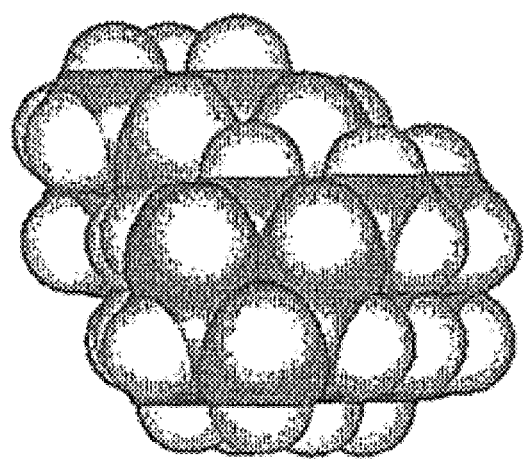
Figure 56:
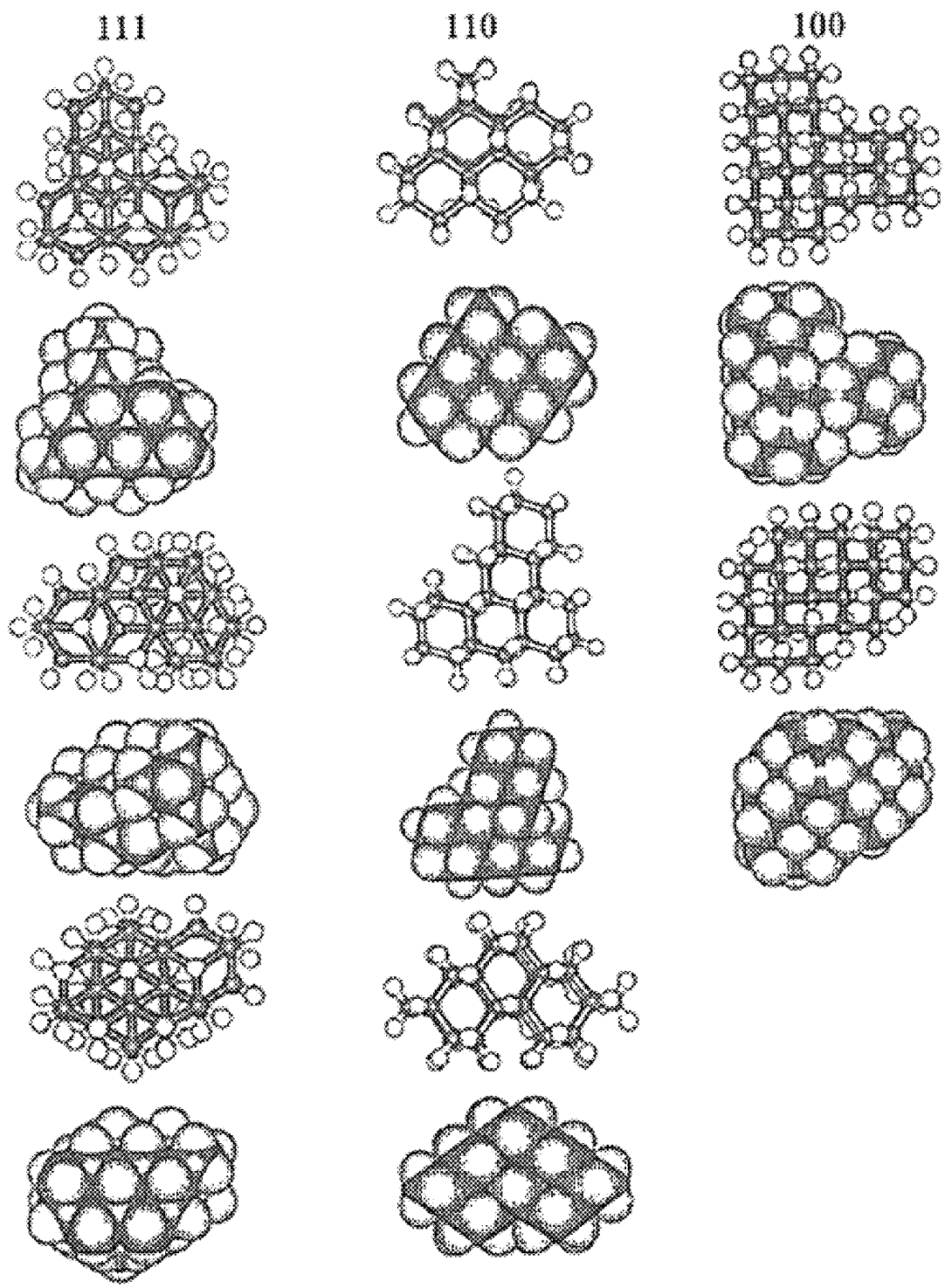
Figure 57:
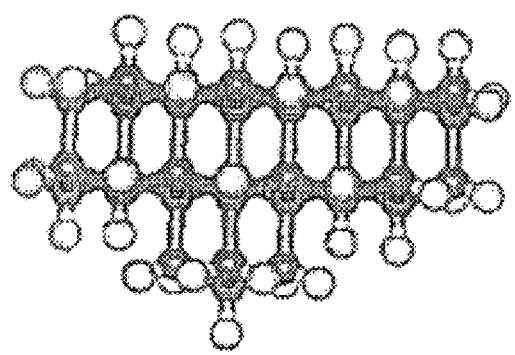
Figure 57:
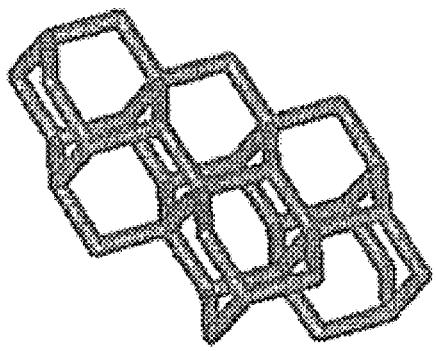
Figure 57:
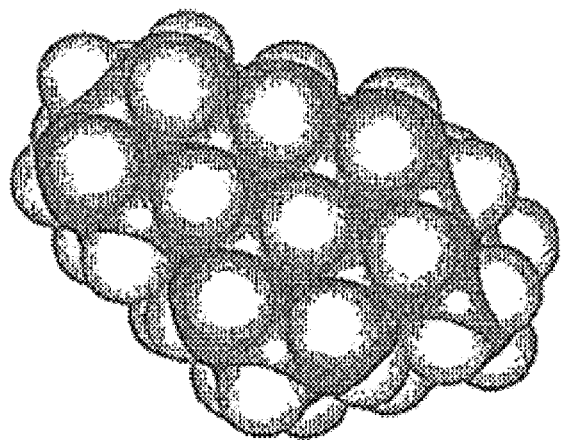
Figure 58:
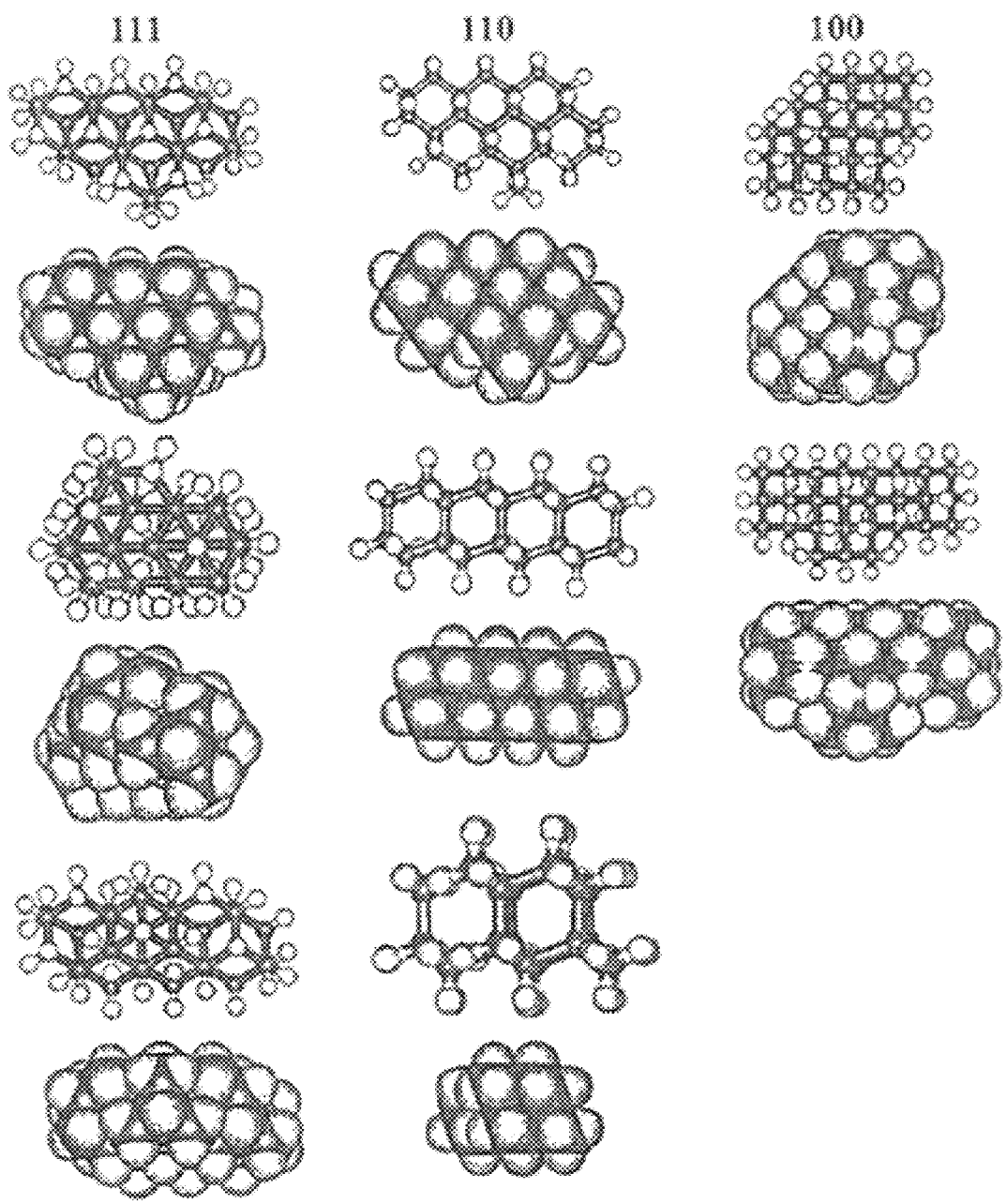
Figure 59:
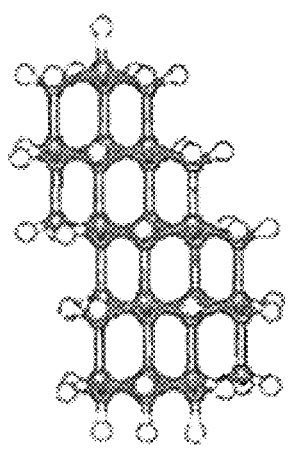
Figure 59:
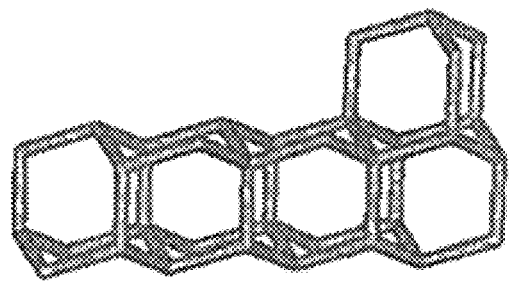
Figure 59:
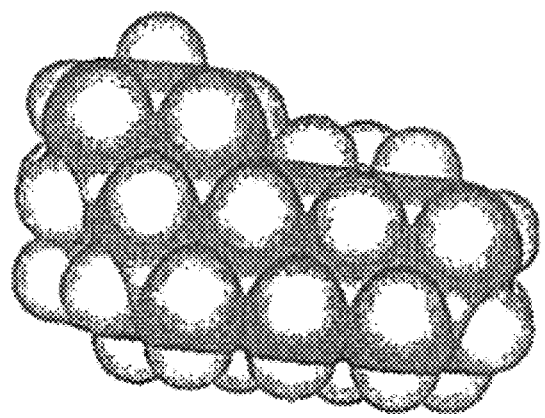
Figure 60:
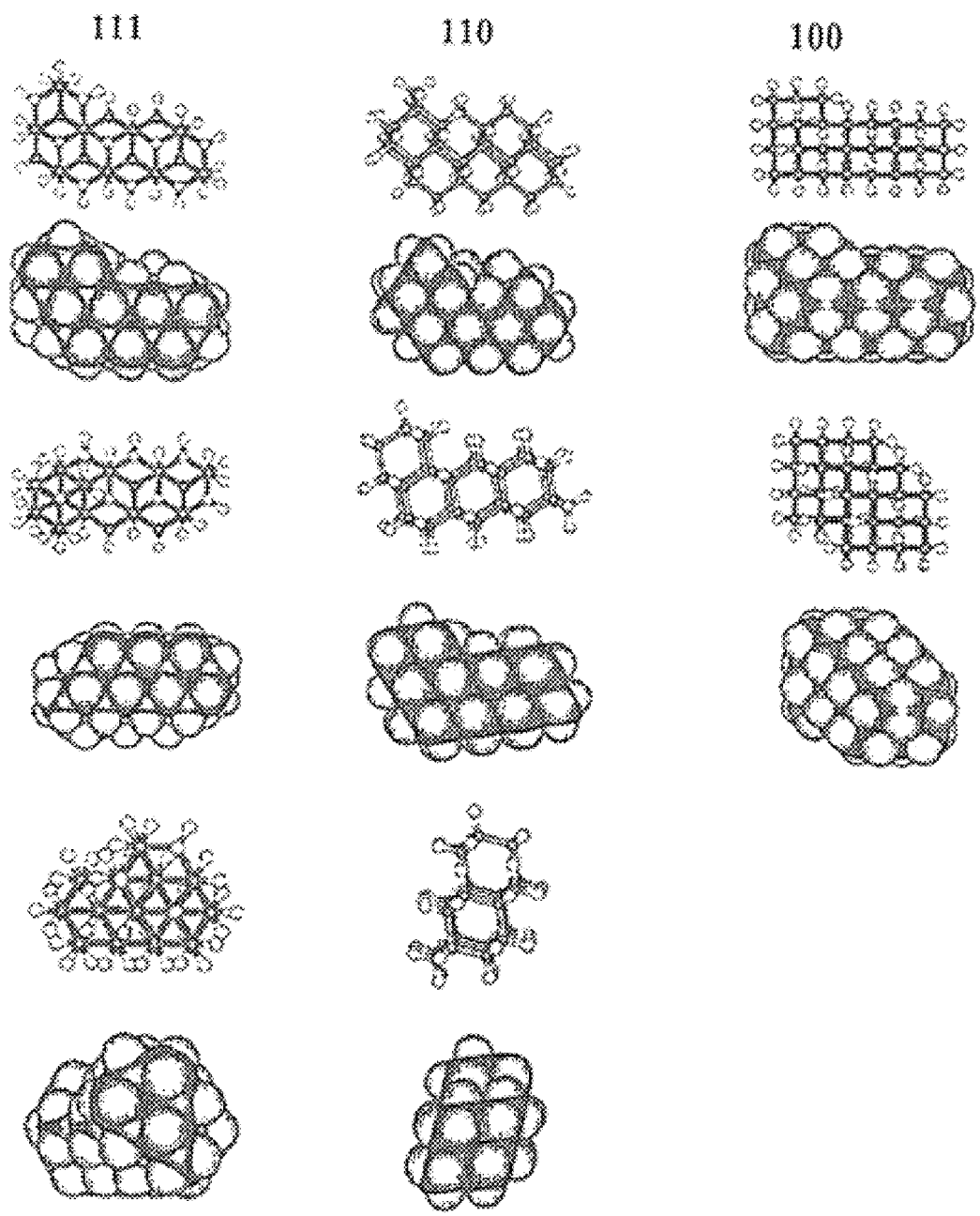
Figure 61:
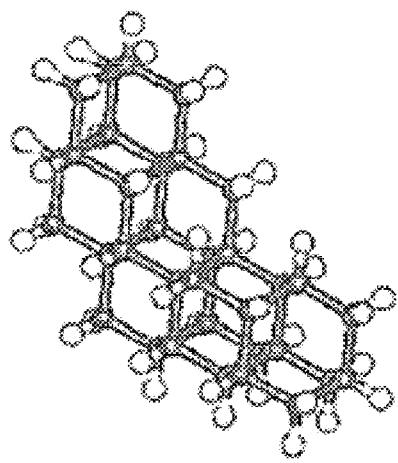
Figure 61:
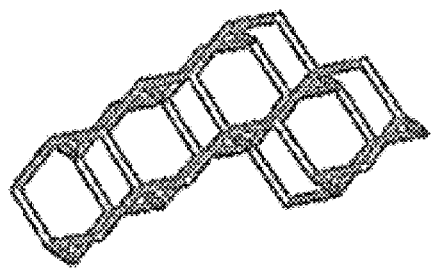
Figure 61:
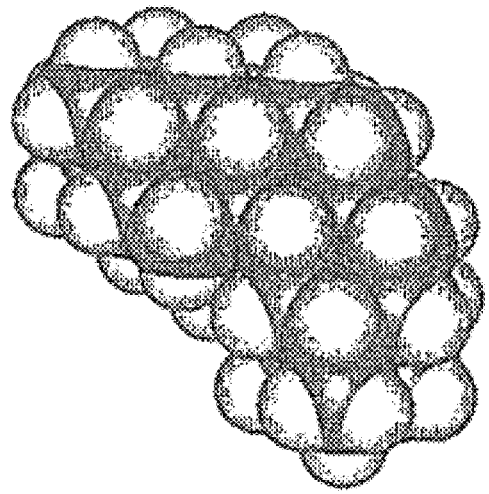
Figure 62:
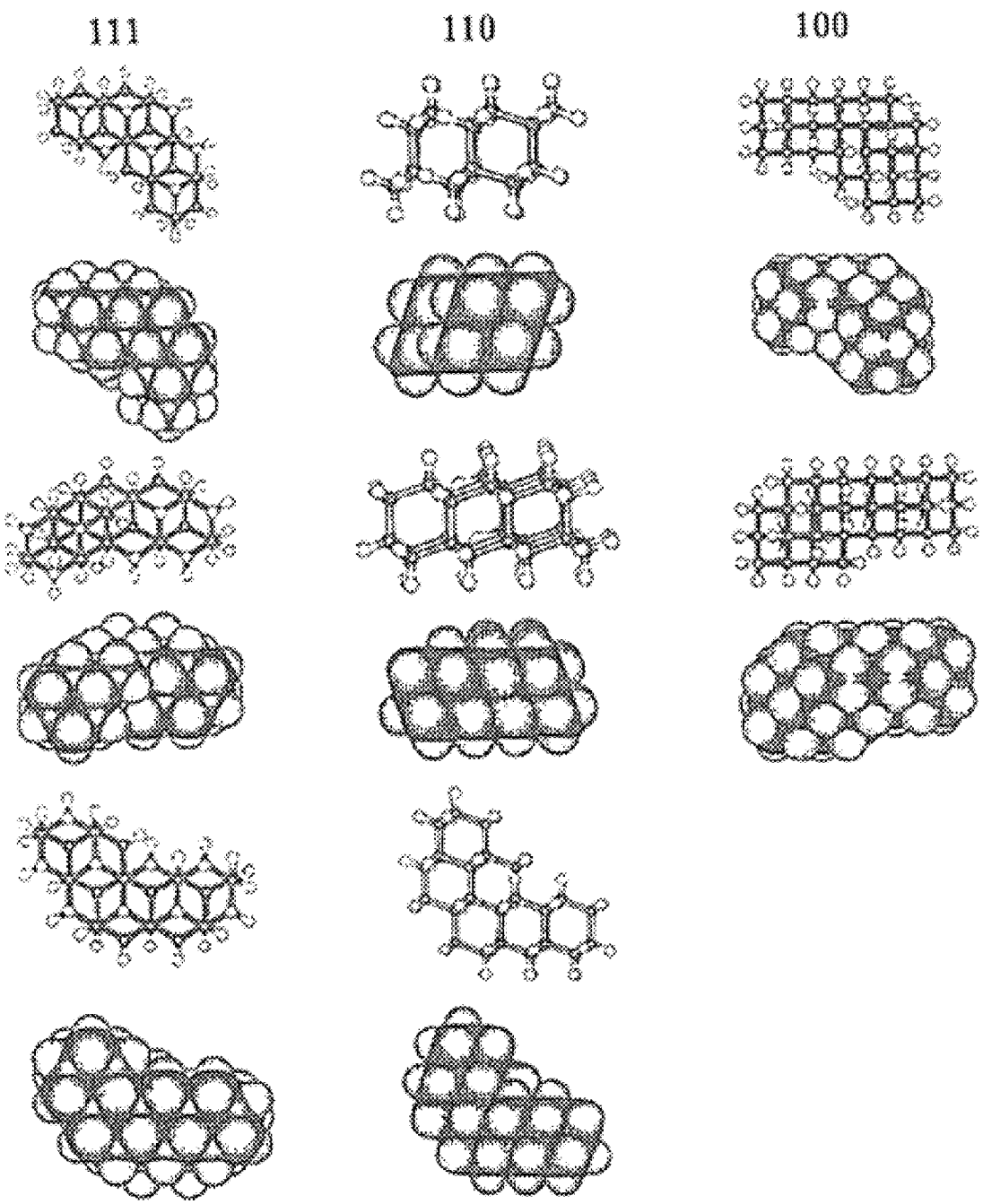
Figure 63:
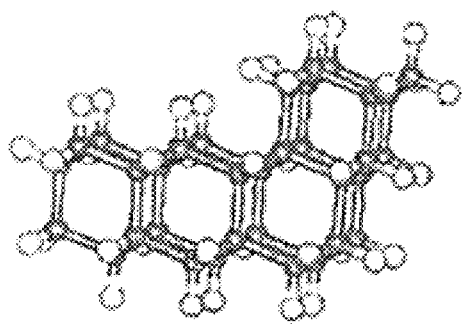
Figure 63:
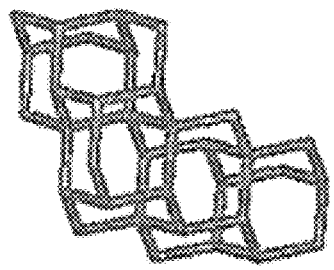
Figure 63:
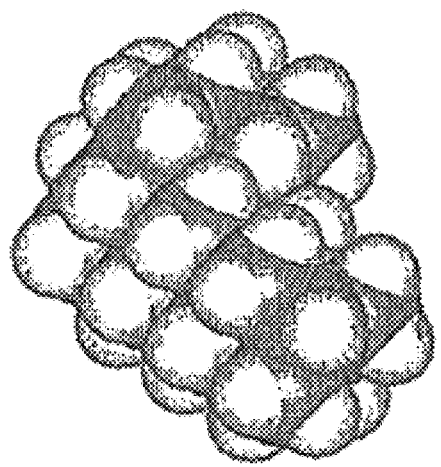
Figure 64:
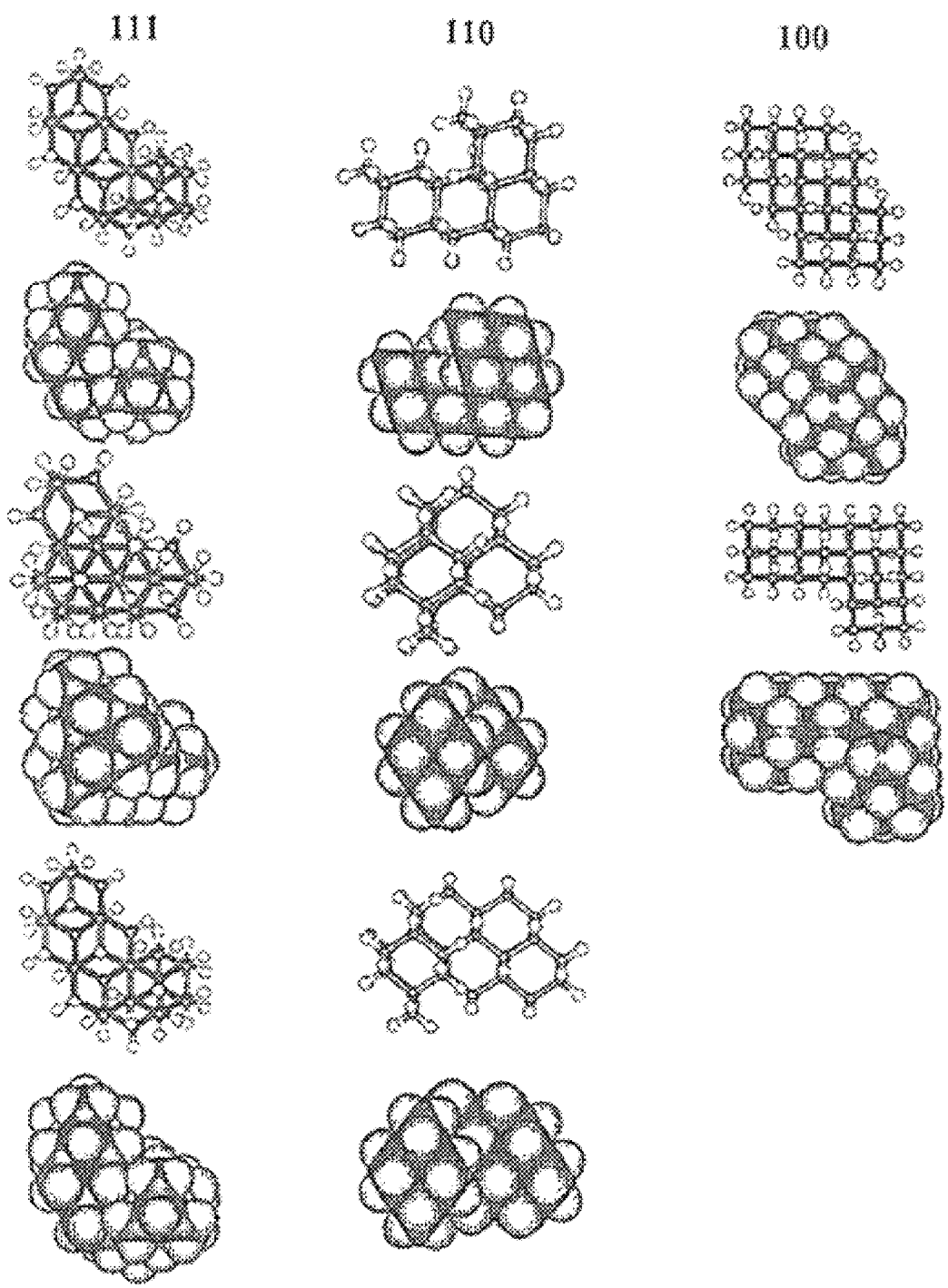
Figure 65:
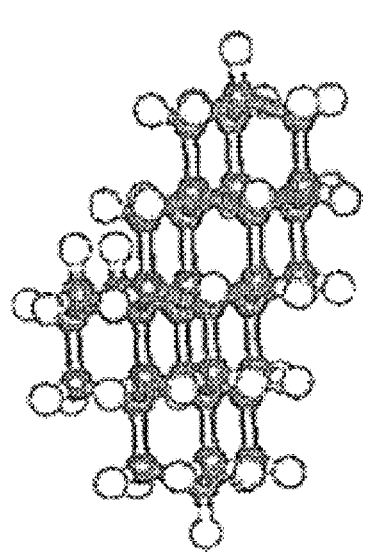
Figure 65:
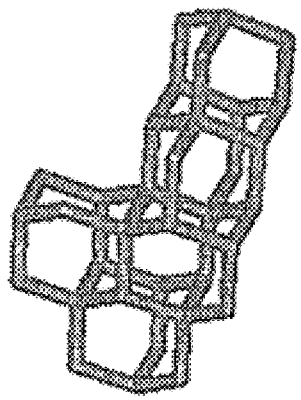
Figure 65:
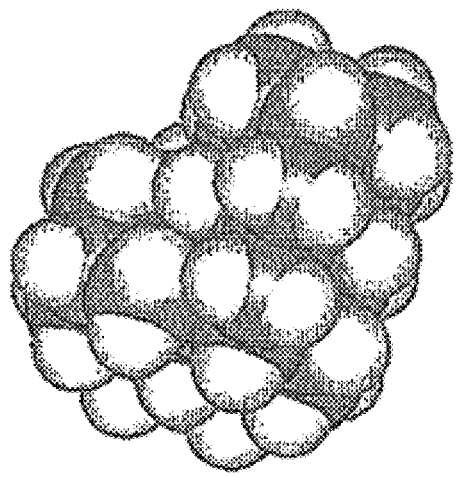
Figure 66:
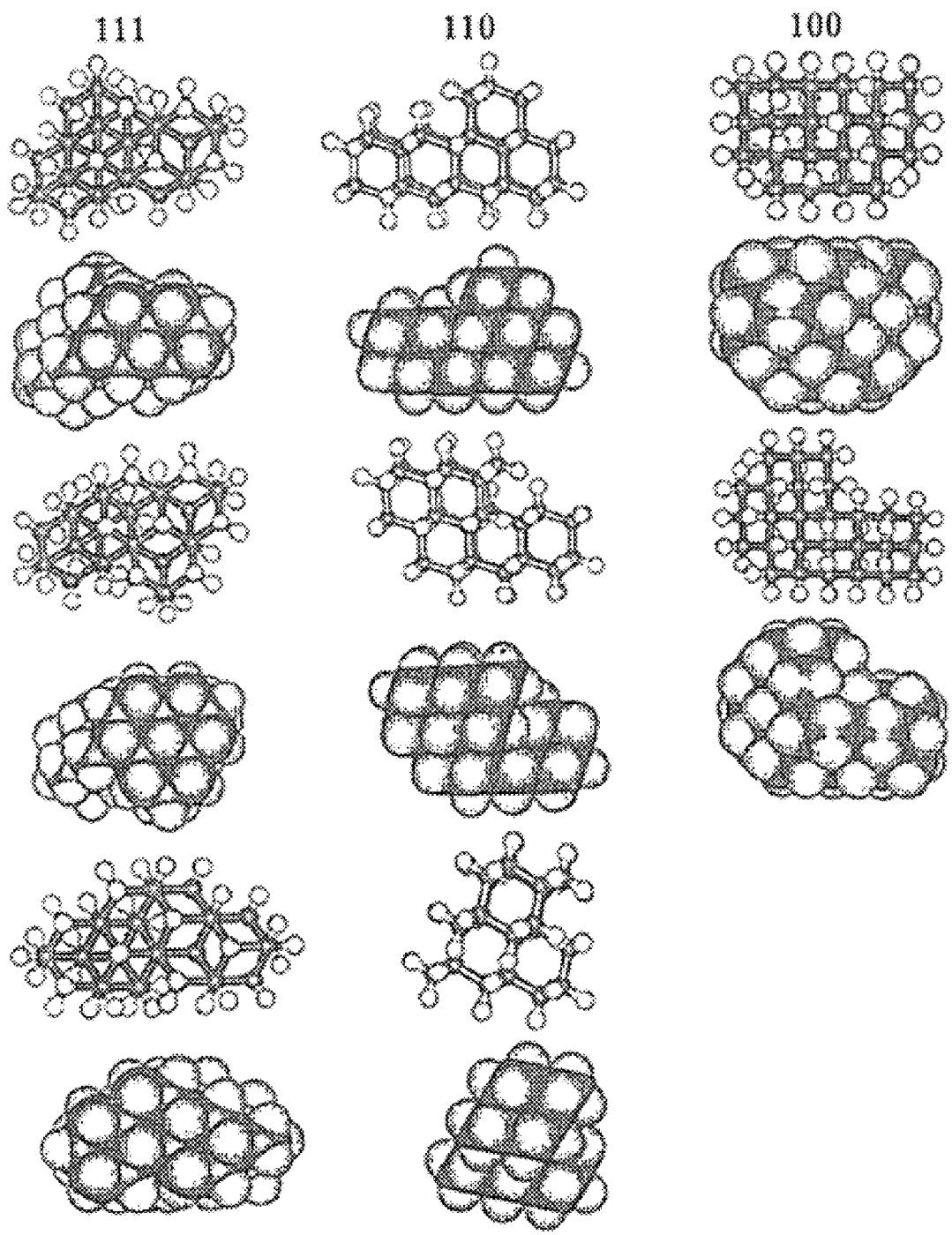
Figure 67:
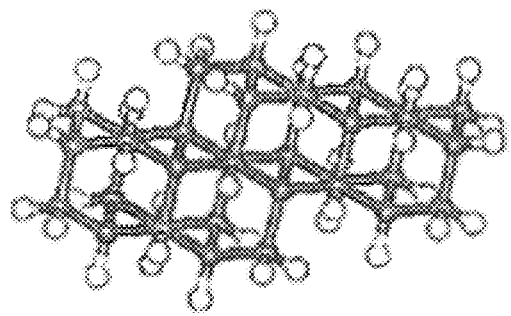
Figure 67:
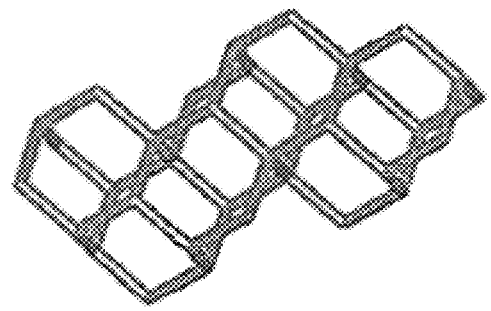
Figure 67:
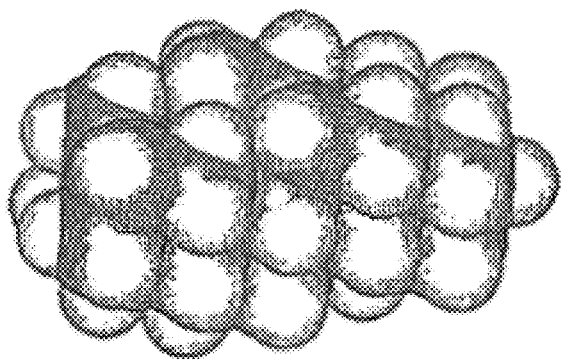
Figure 68:
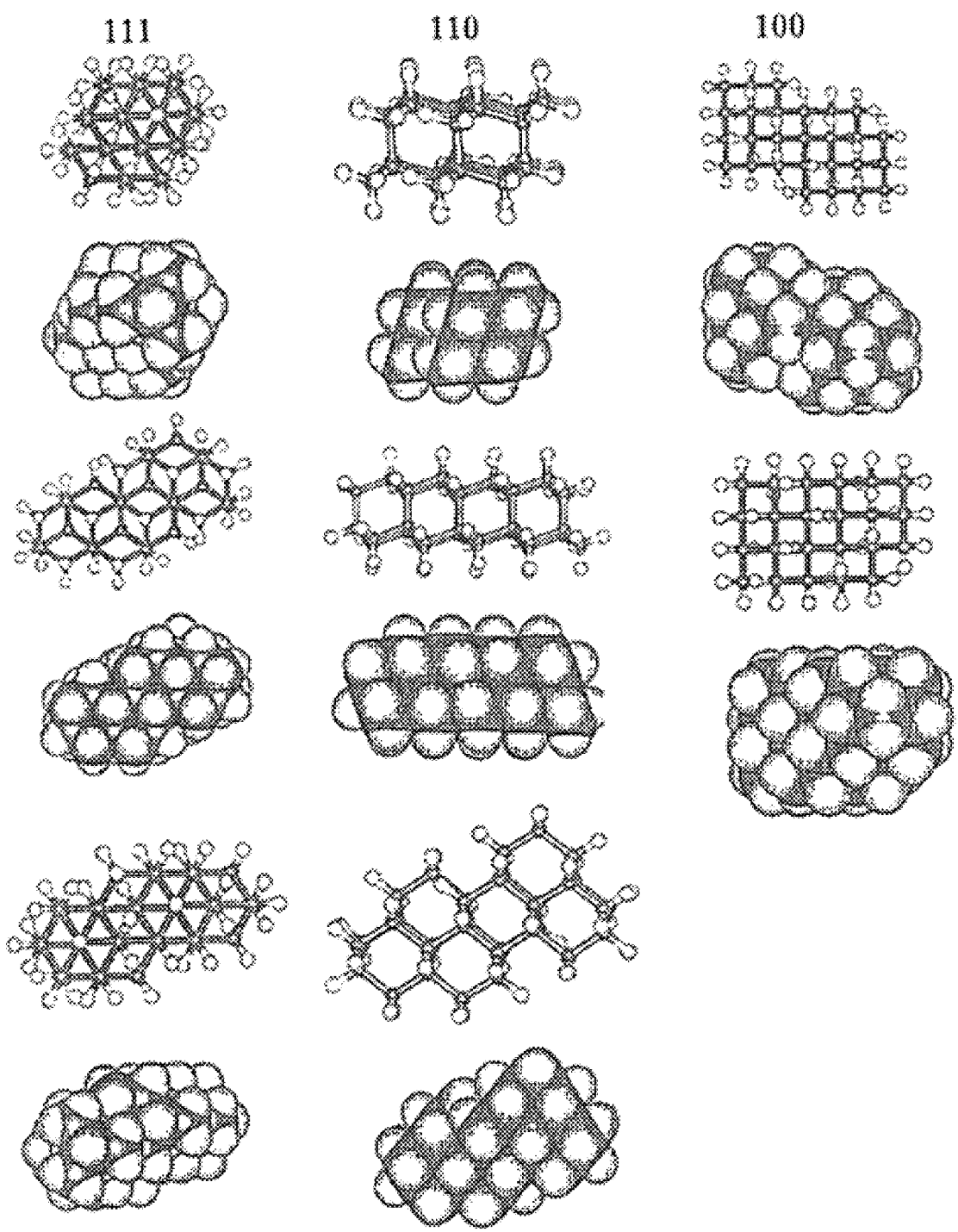
Figure 69:
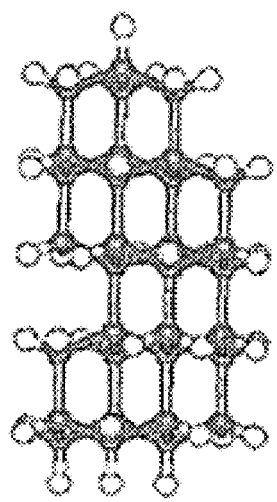
Figure 69:
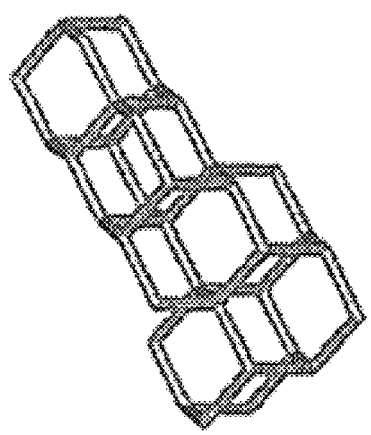
Figure 69:
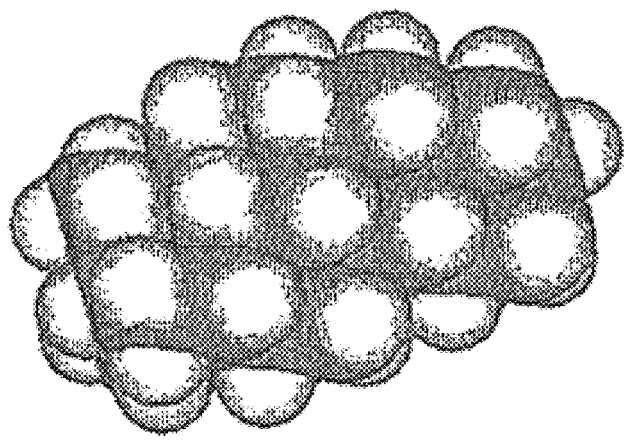
Figure 70:
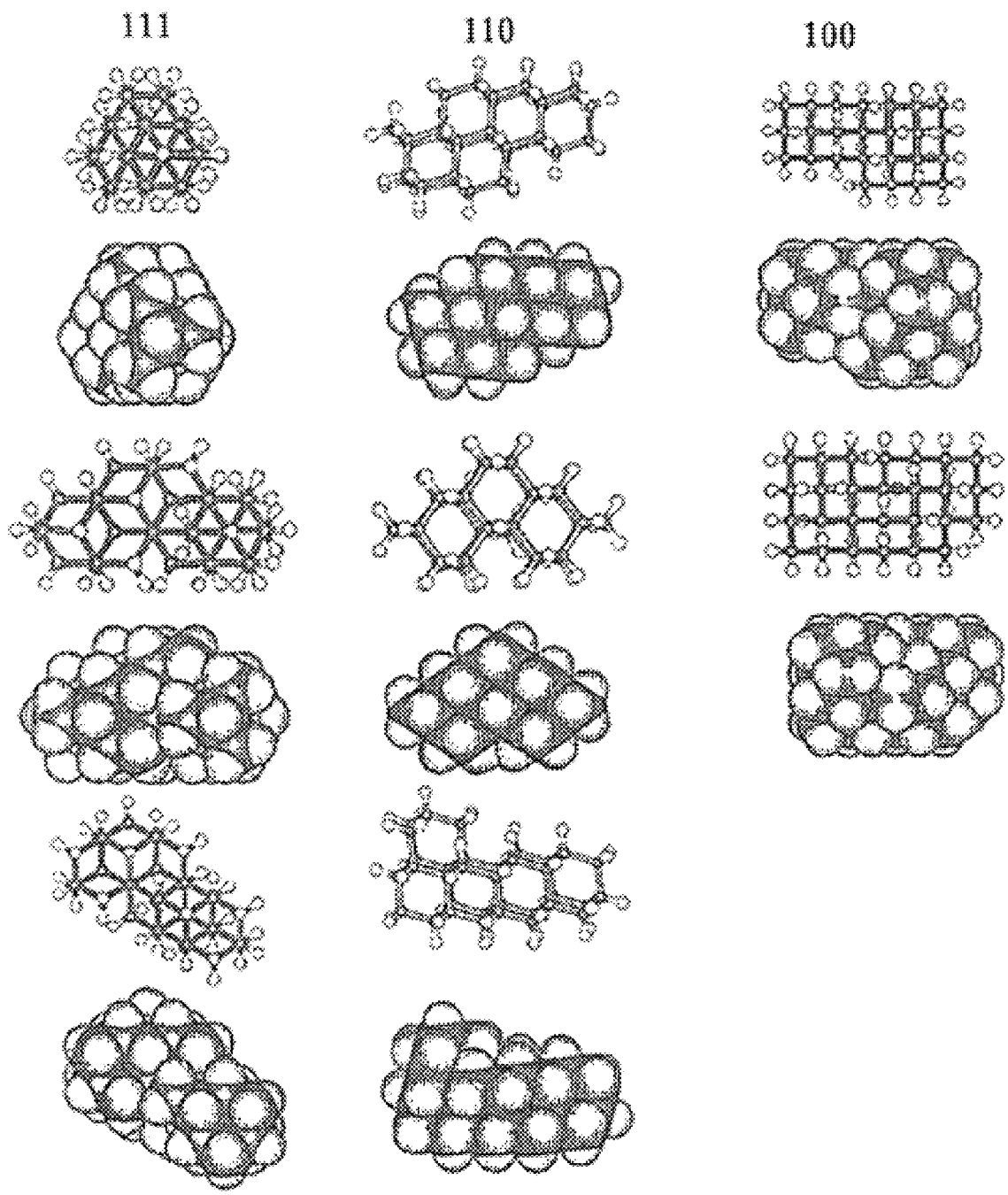
Figure 71:
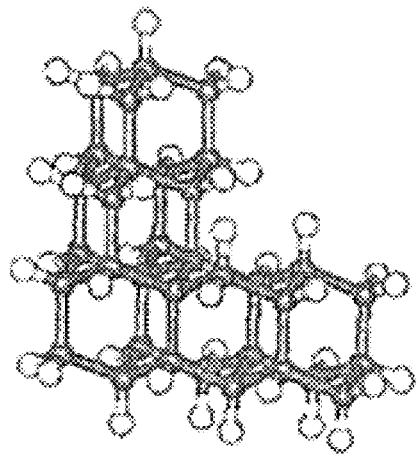
Figure 71:
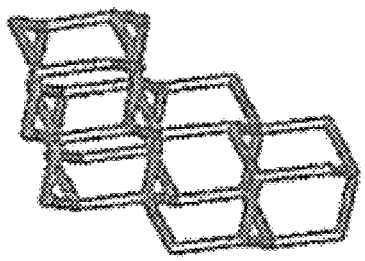
Figure 71:
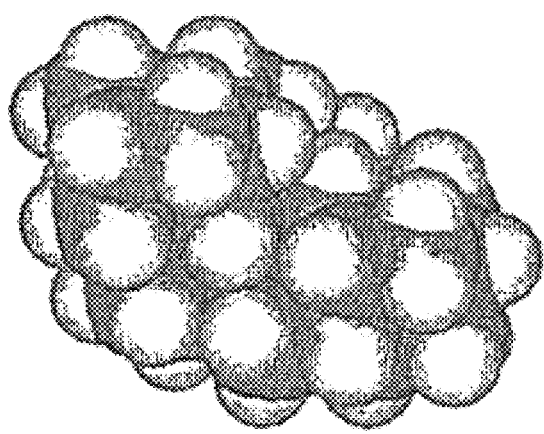
Figure 72:
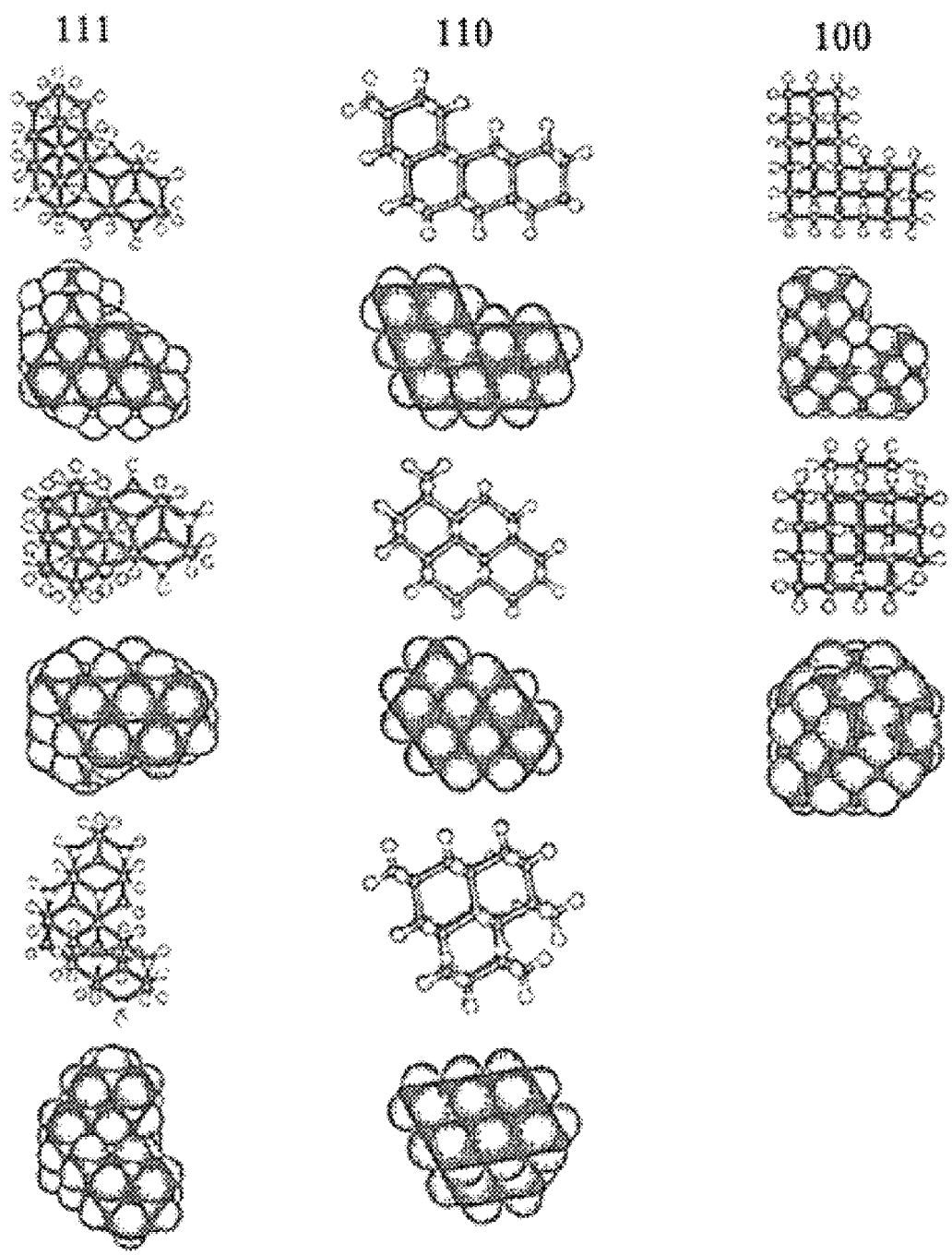
Figure 73:
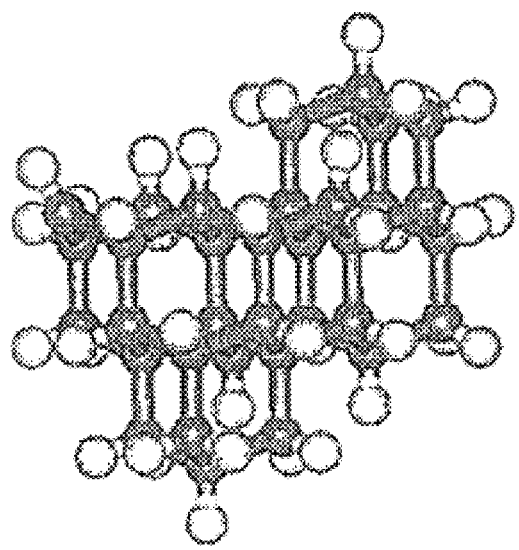
Figure 73:
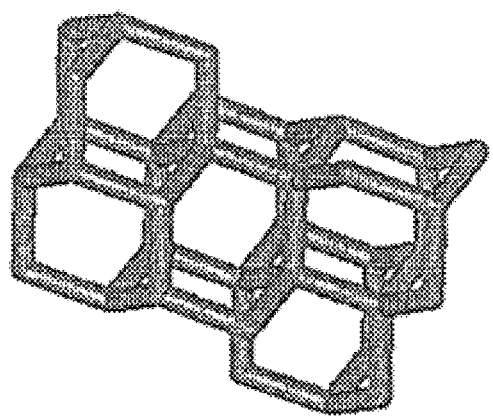
Figure 73:
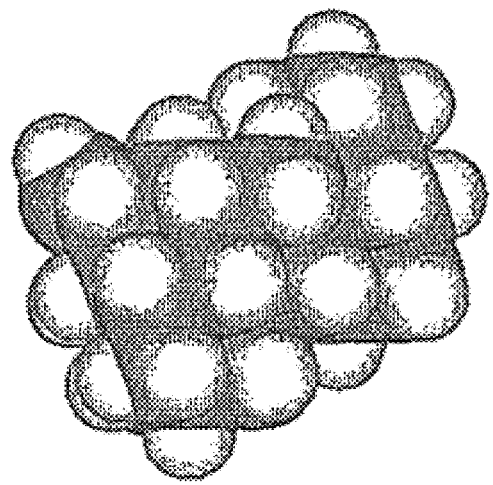
Figure 74:
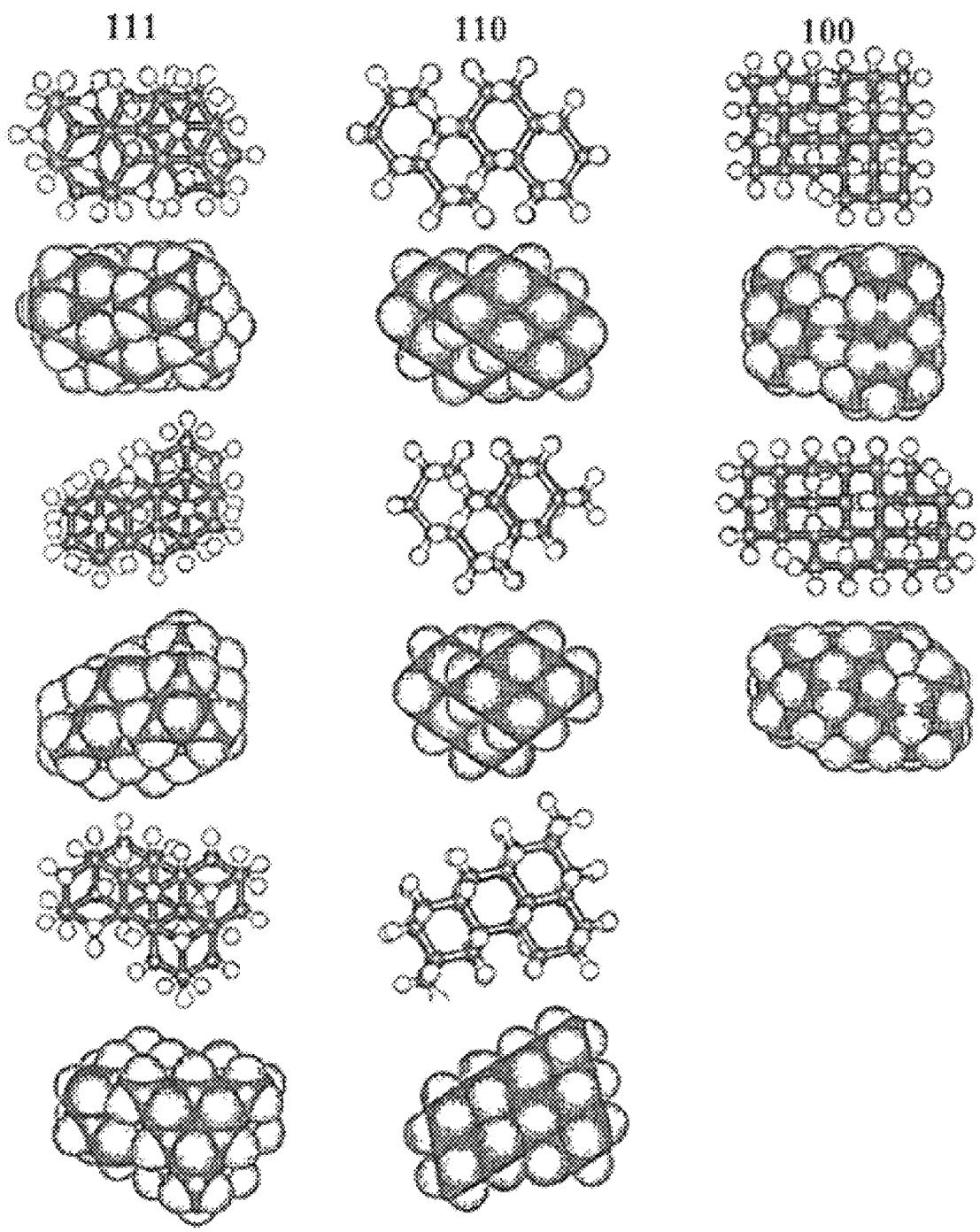
Figure 75:
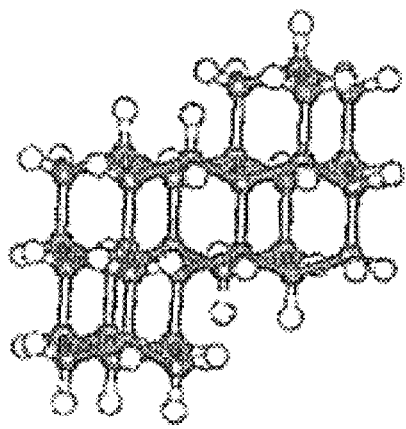
Figure 75:
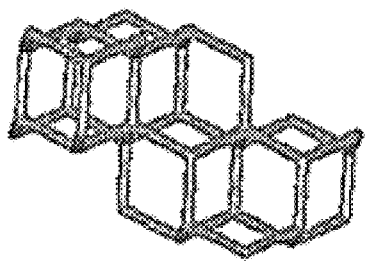
Figure 75:
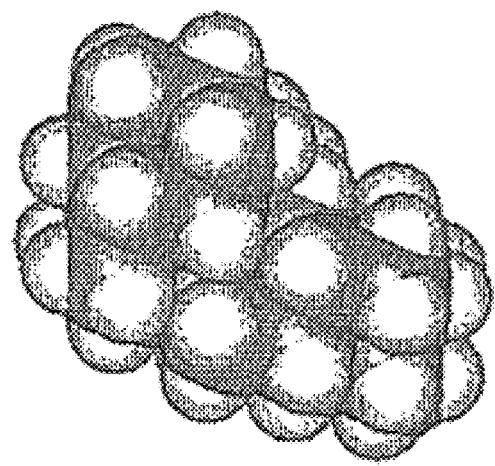
Figure 76:
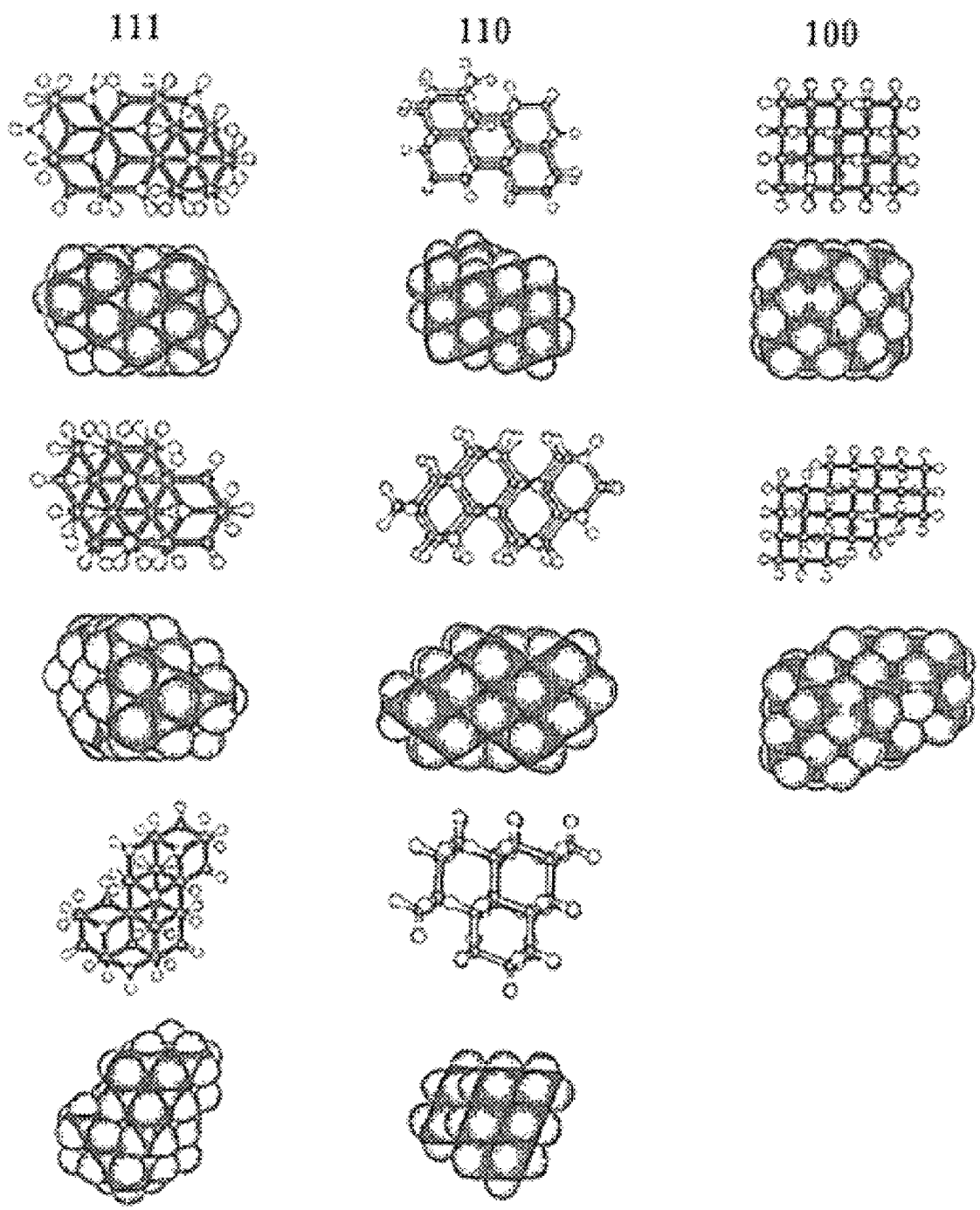
Figure 77:
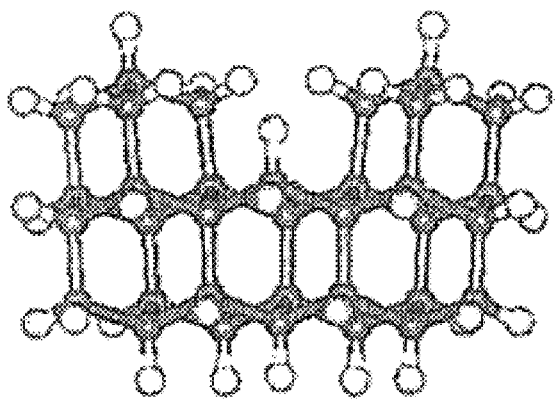
Figure 77:
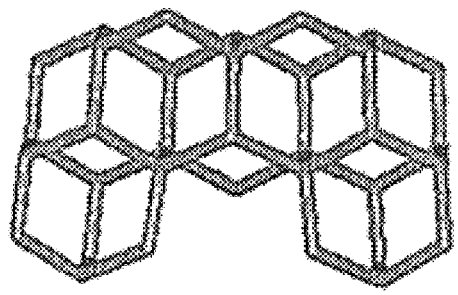
Figure 77:
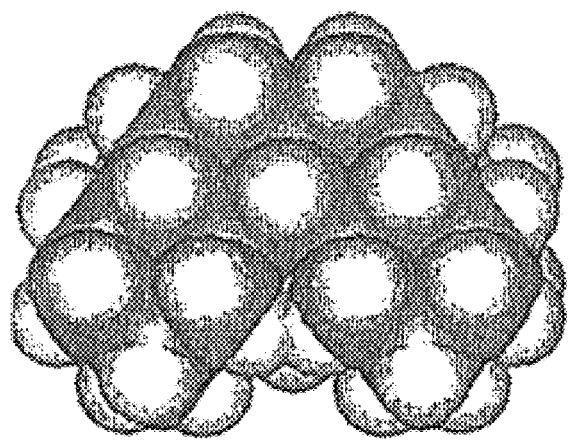
Figure 78:
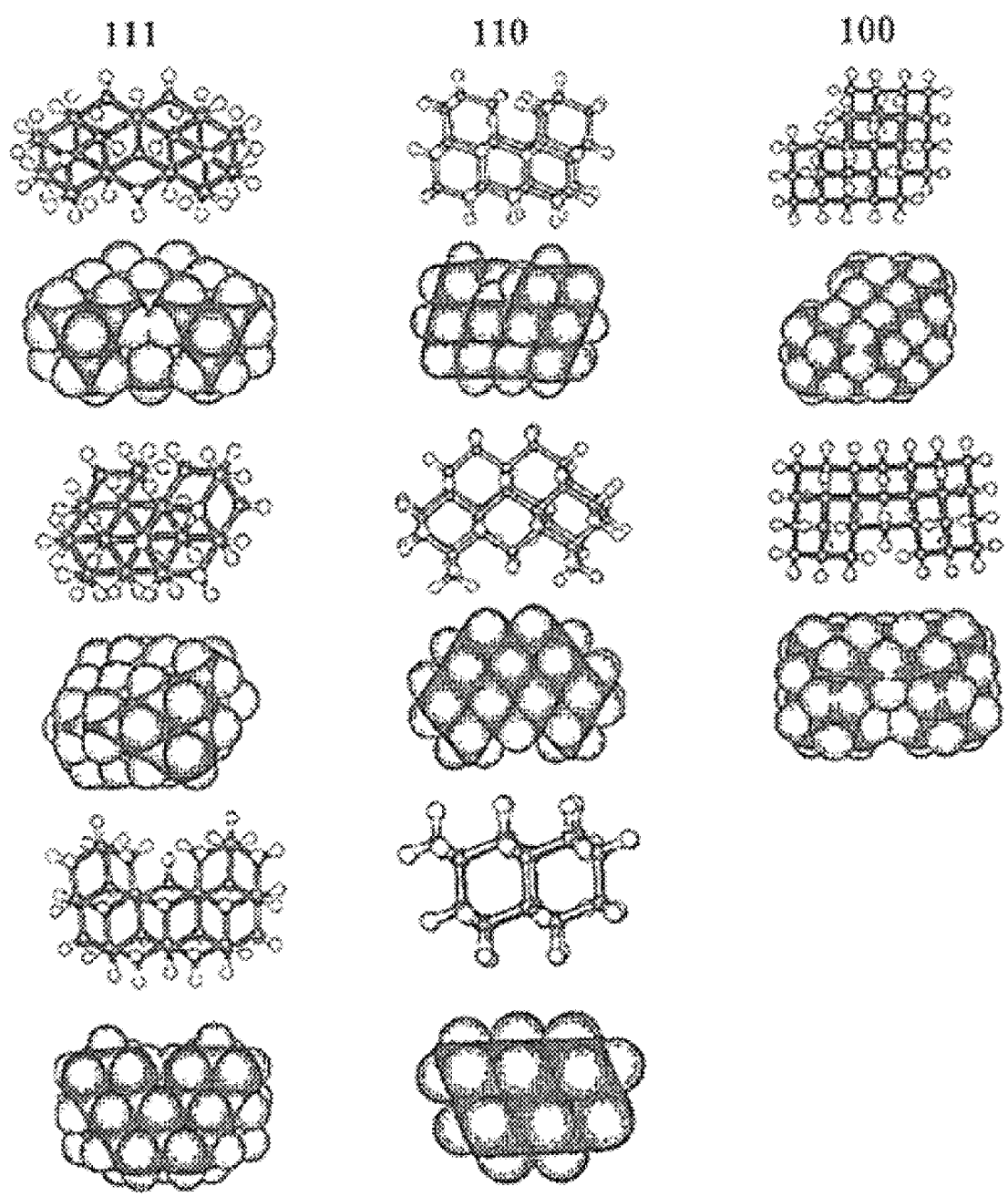
Figure 79:
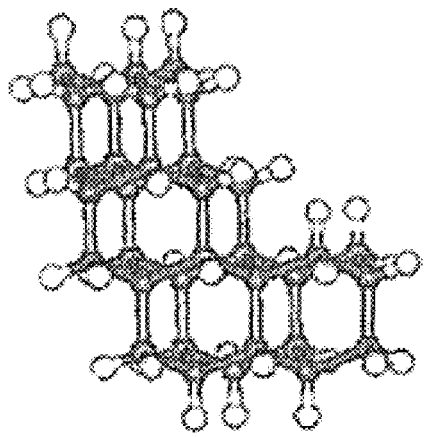
Figure 79:
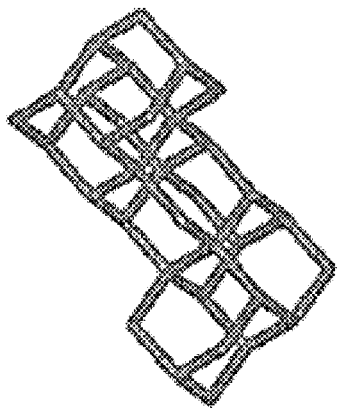
Figure 79:
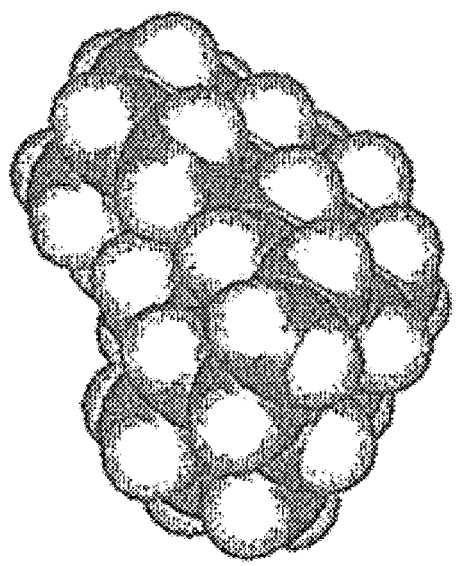
Figure 80:
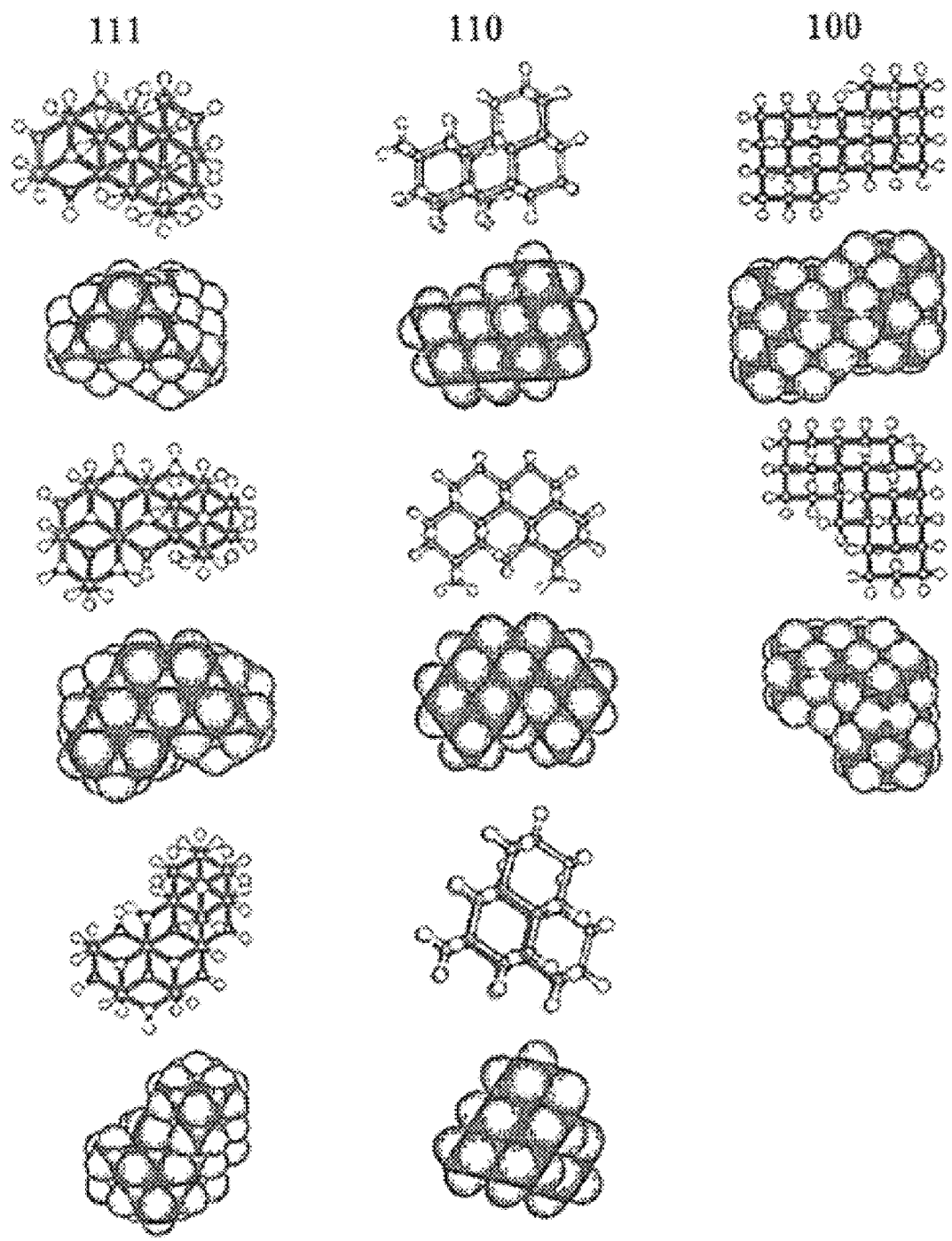
Figure 81:
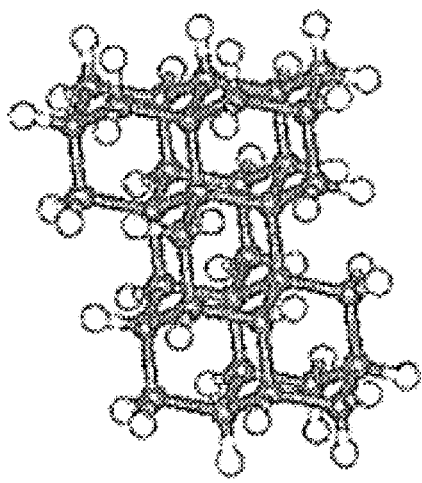
Figure 81:
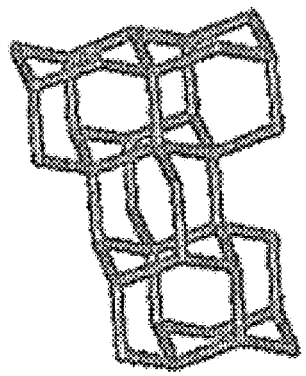
Figure 81:
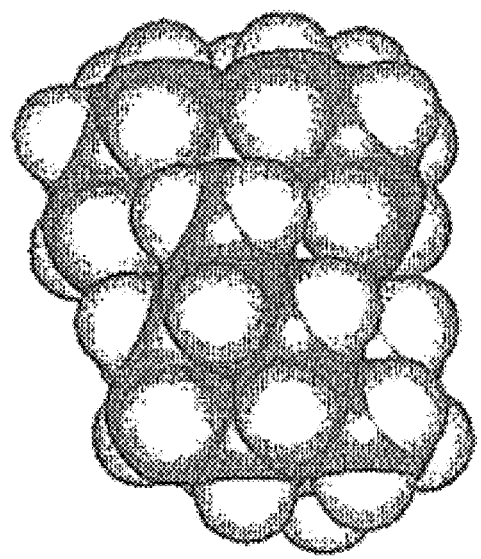
Figure 82:
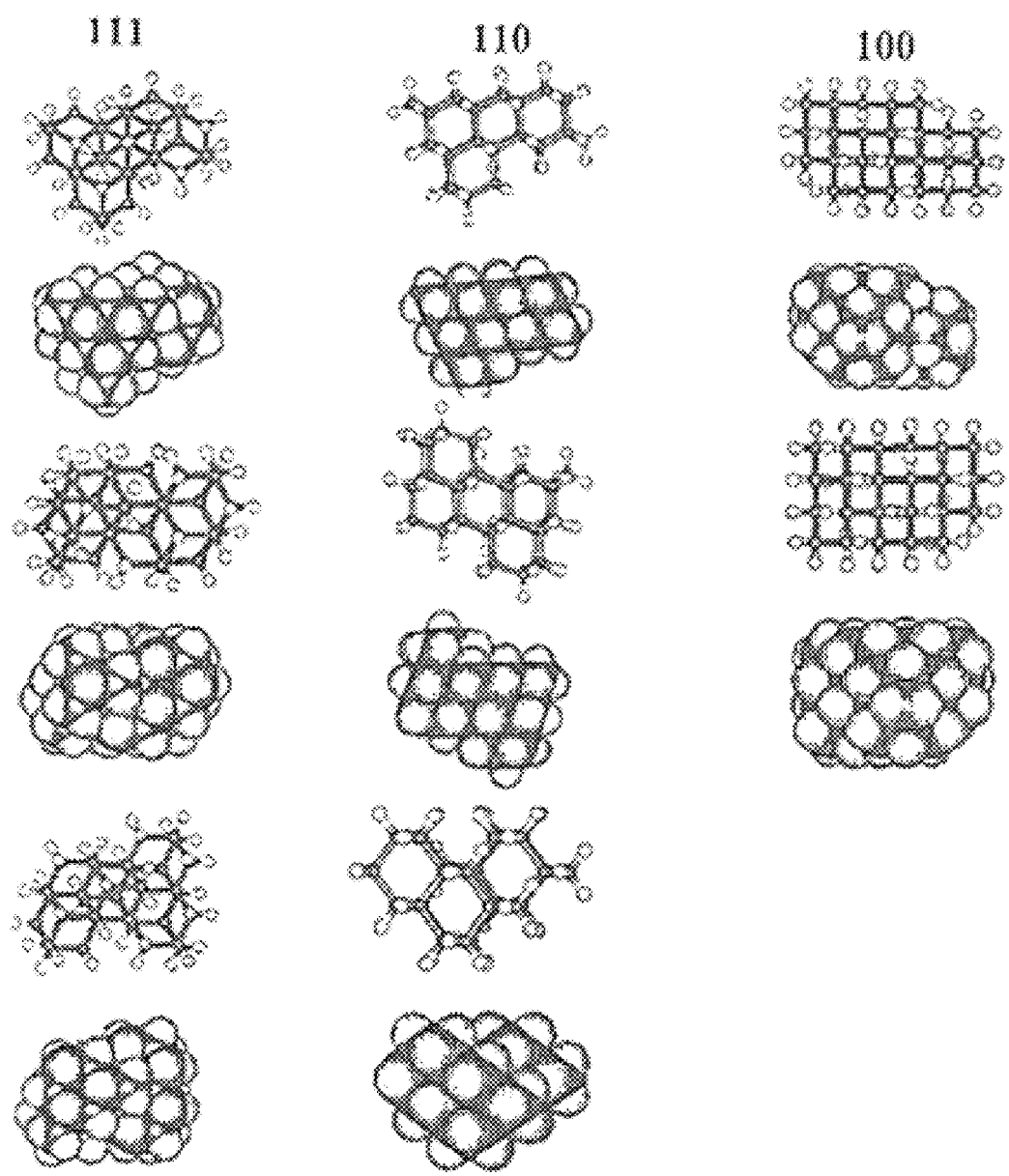
Figure 83:
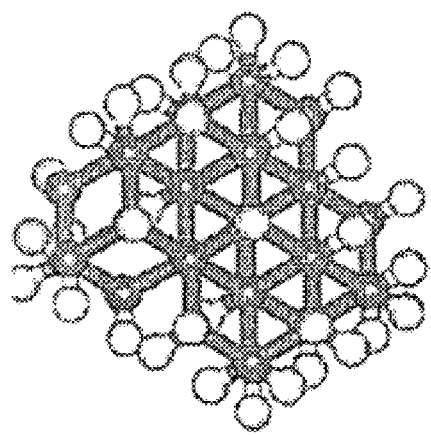
Figure 83:
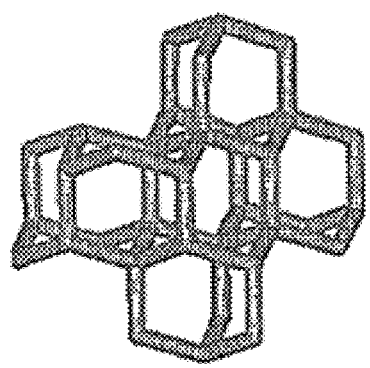
Figure 83:
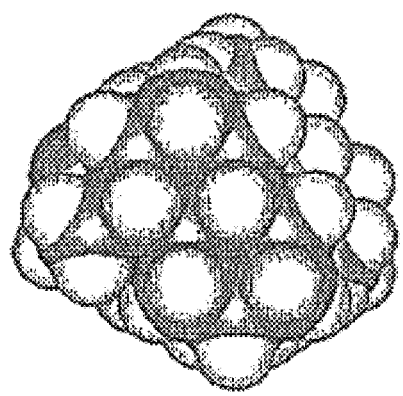
Figure 84:
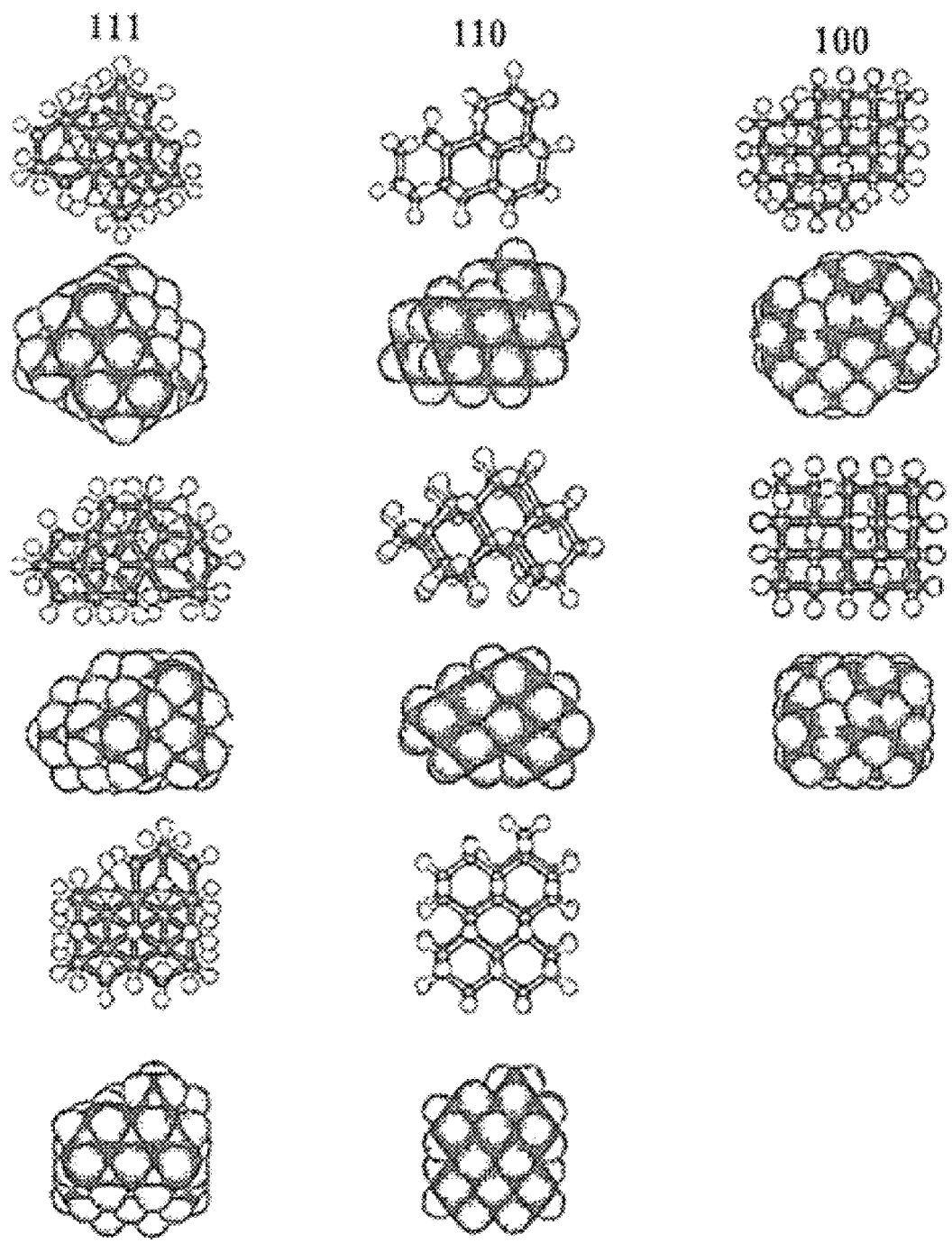
Figure 85:
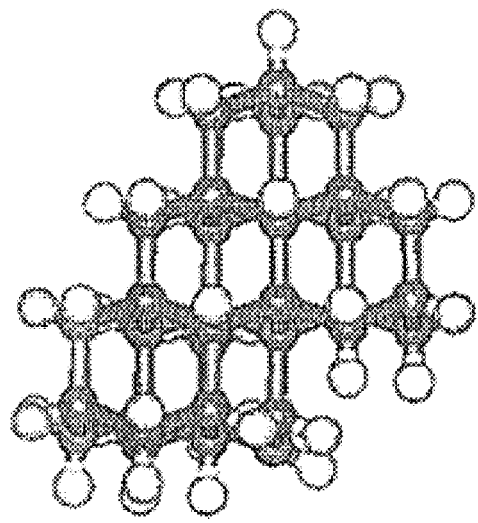
Figure 85:
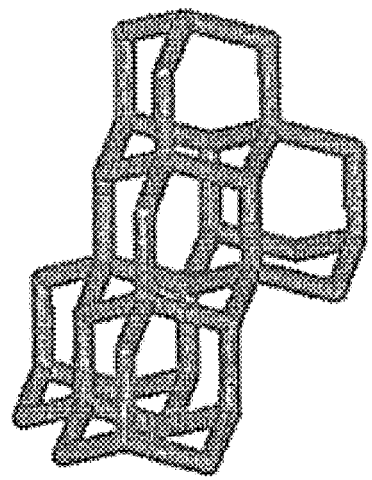
Figure 85:
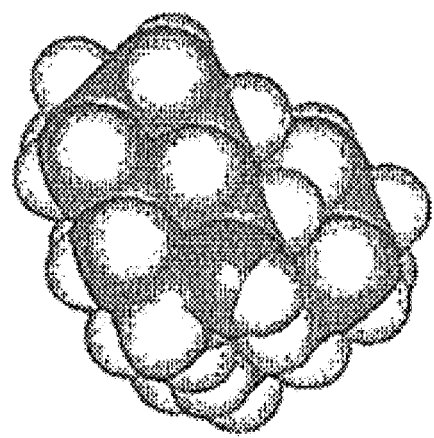
Figure 86:
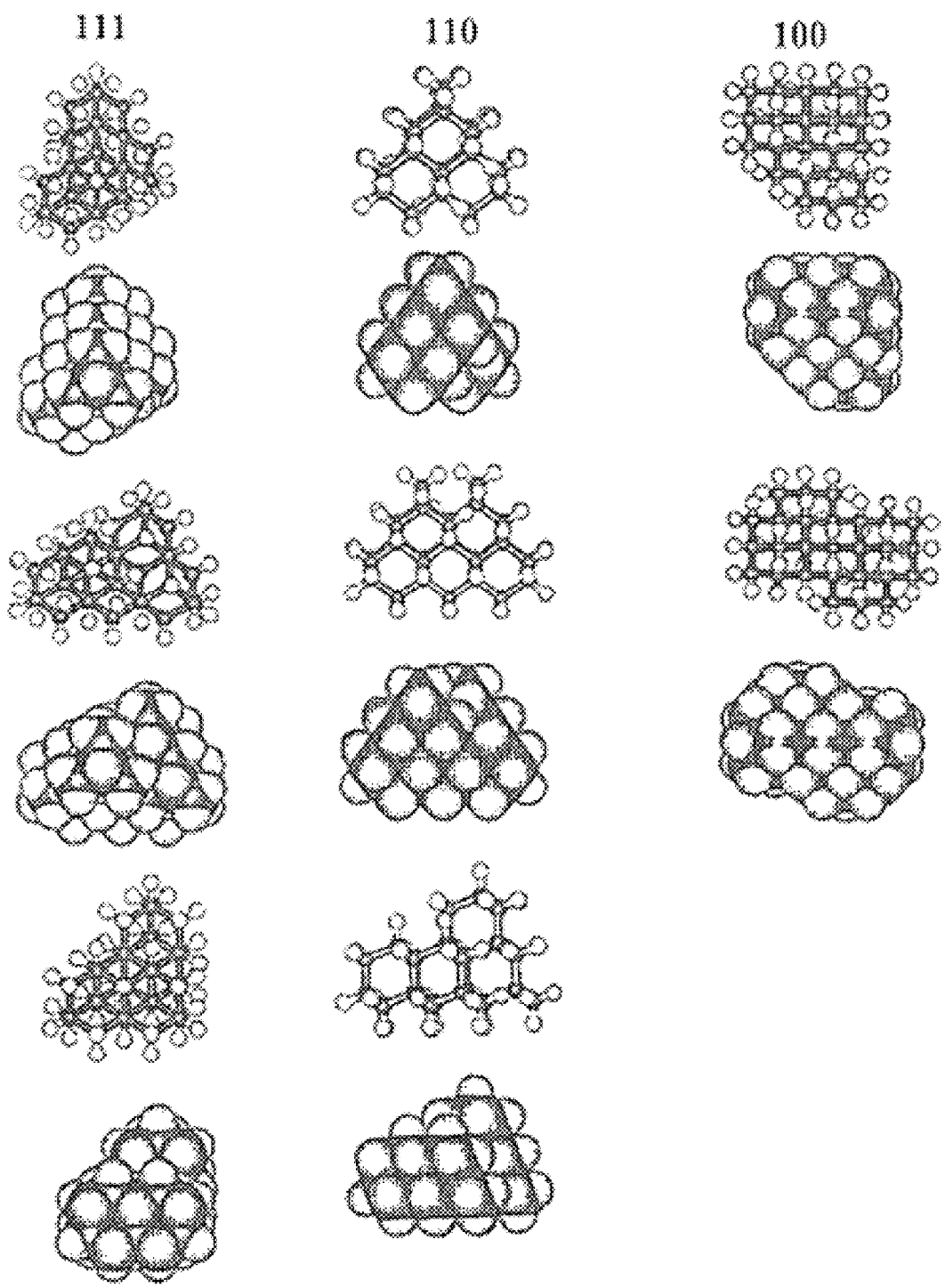
Figure 87:
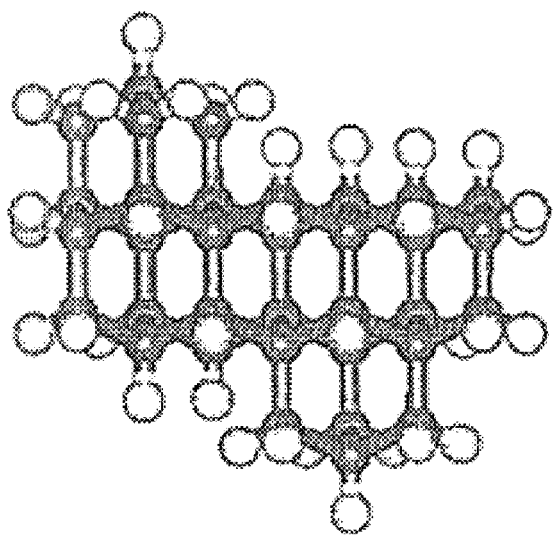
Figure 87:
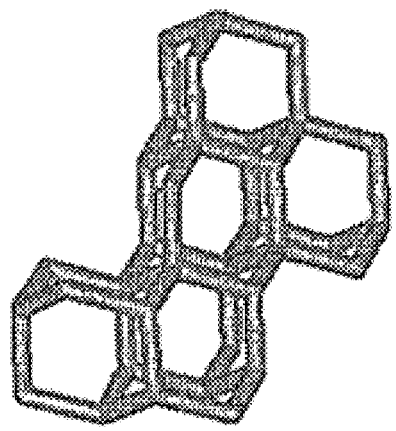
Figure 87:
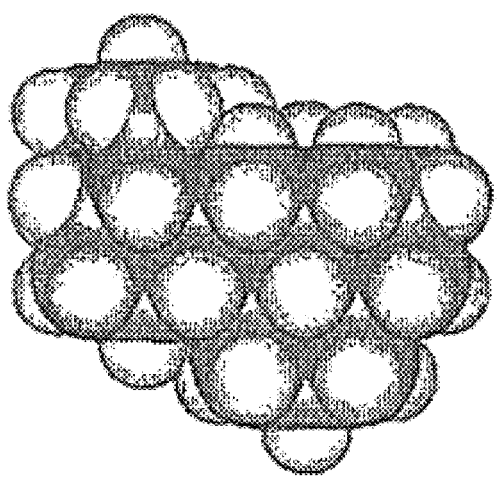
Figure 88:
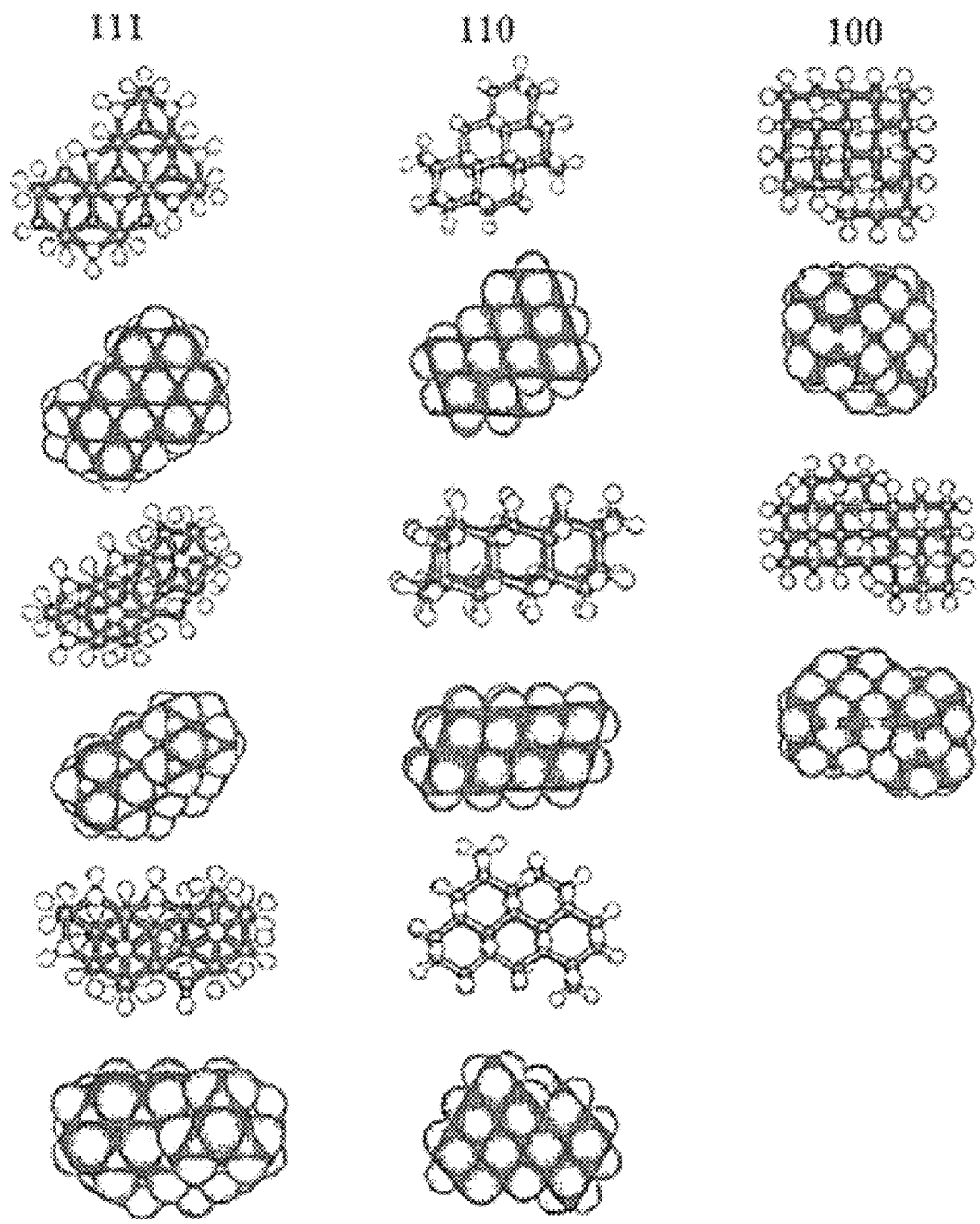
Figure 89:
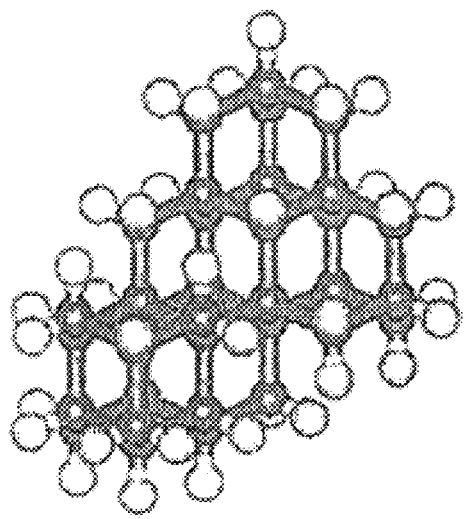
Figure 89:
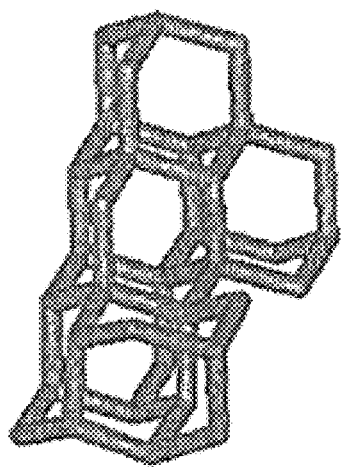
Figure 89:
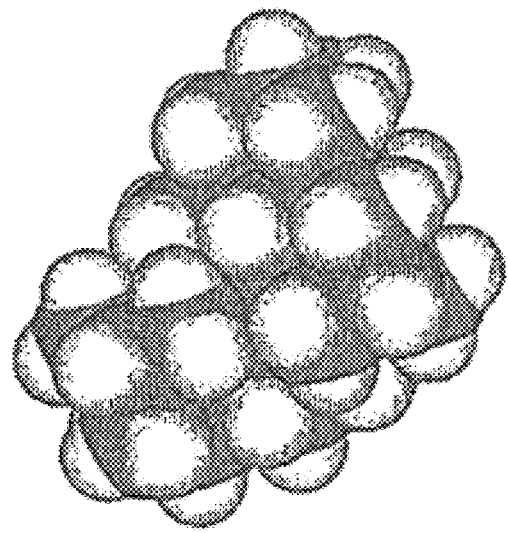
Figure 90:
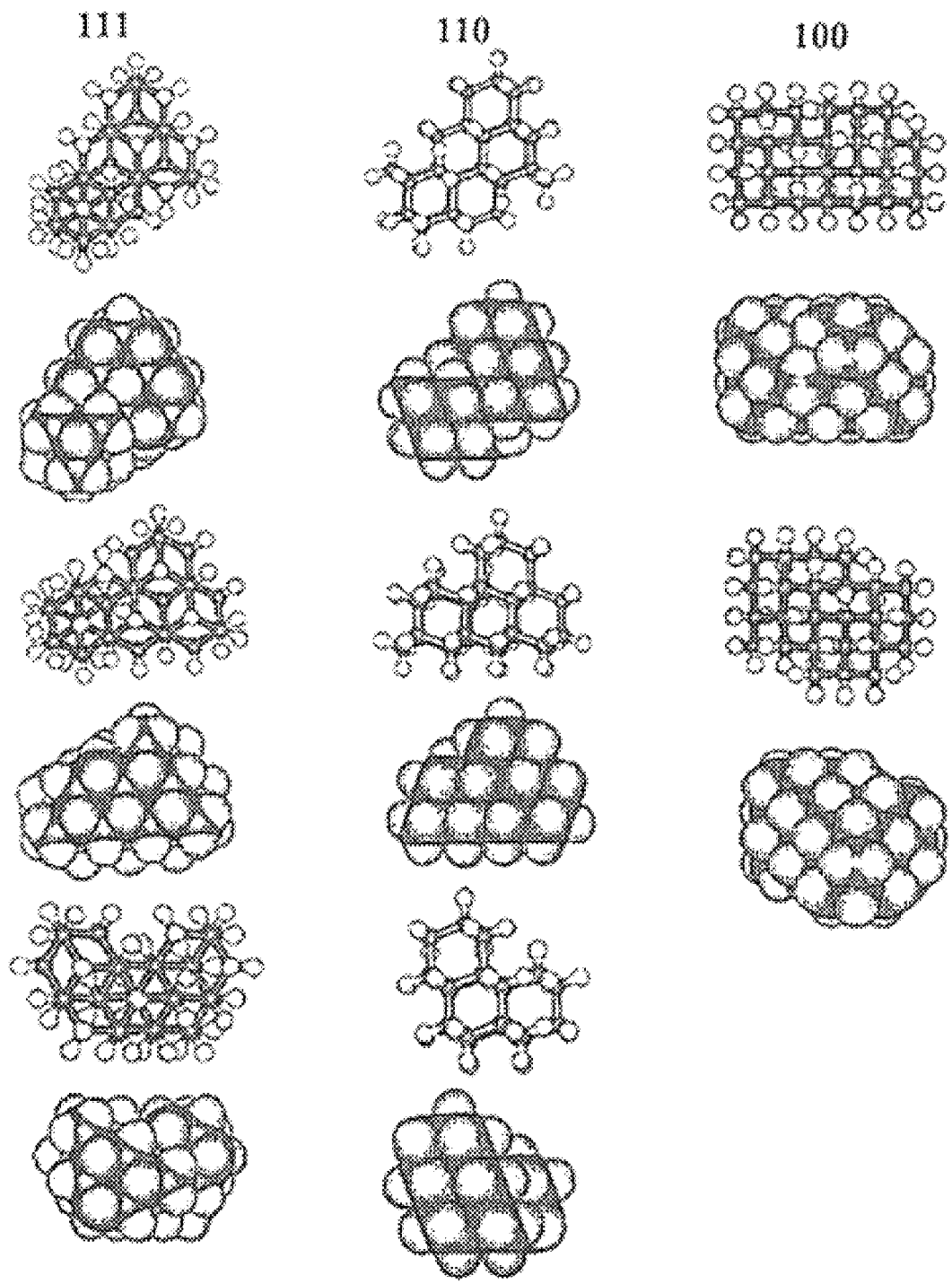
Figure 91:
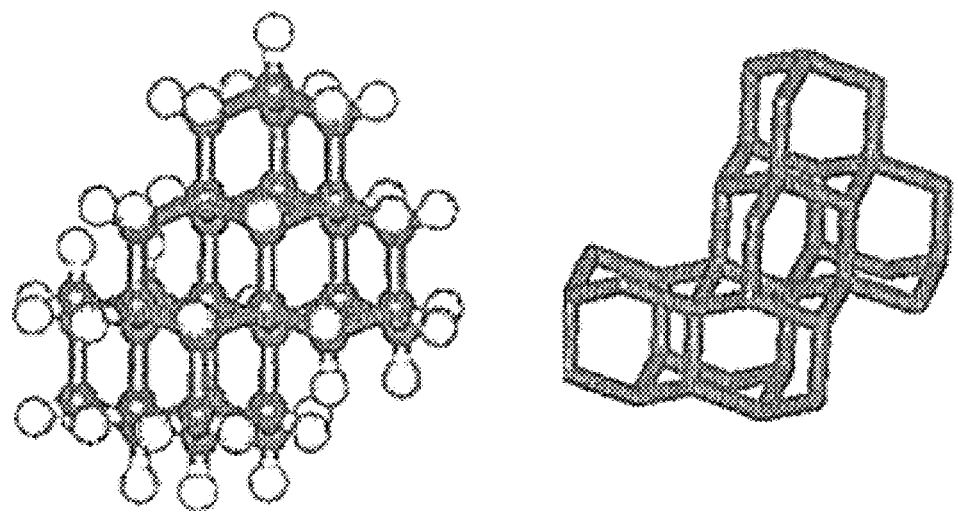
Figure 91:
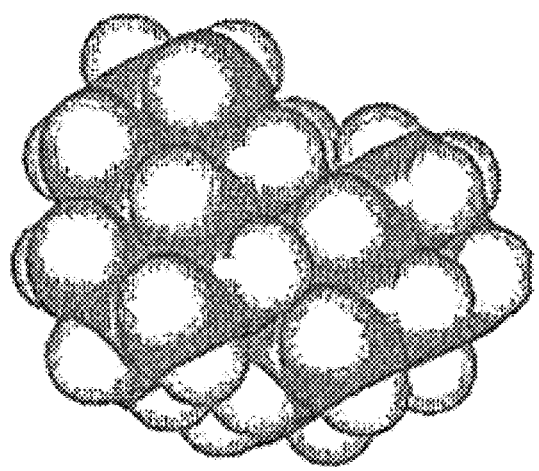
Figure 92:
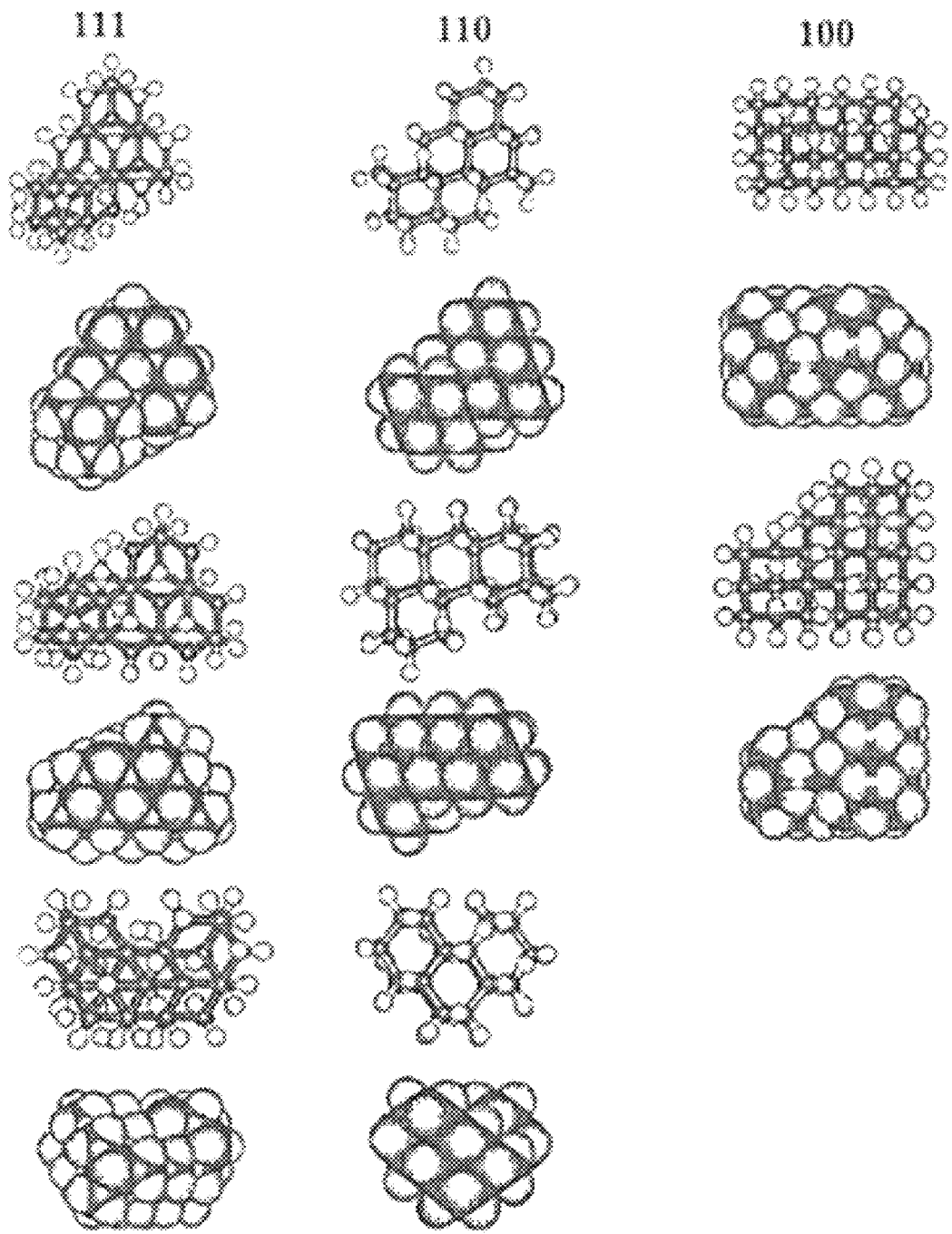
Figure 93:
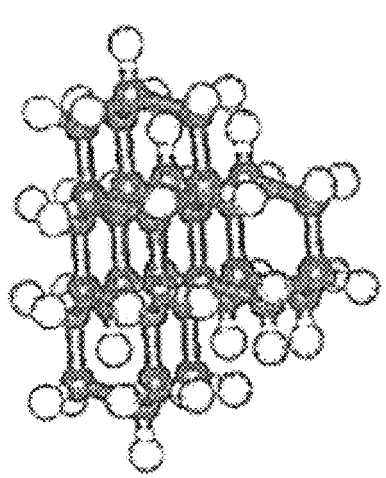
Figure 93:
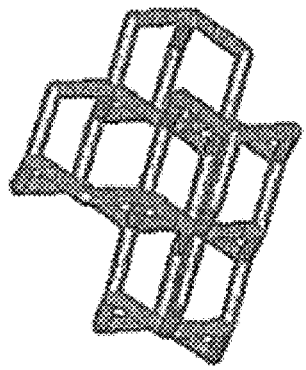
Figure 93:
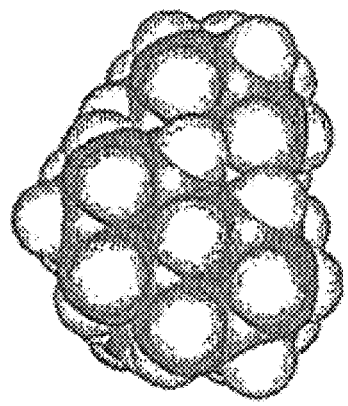
Figure 94:
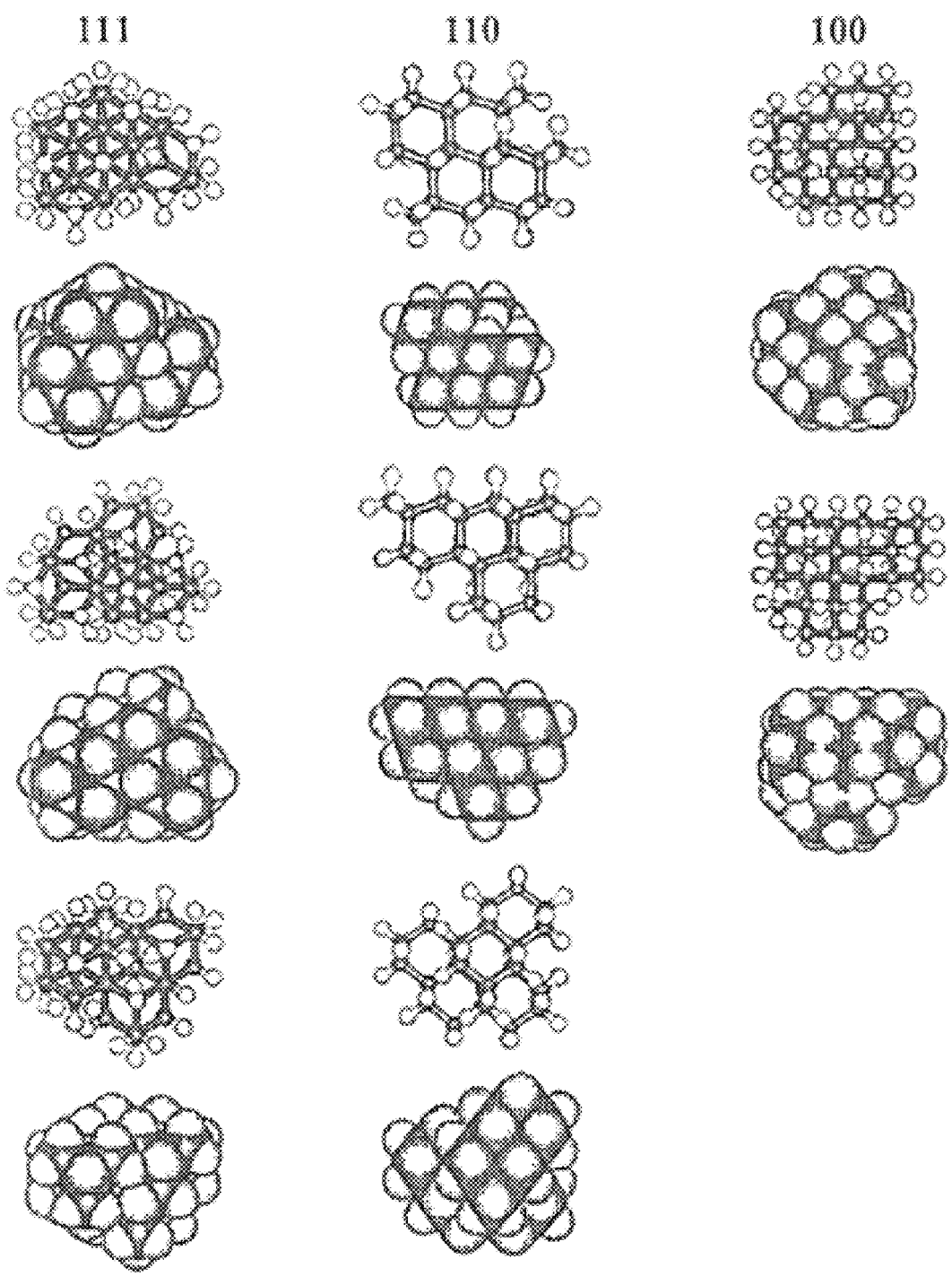
Figure 95:
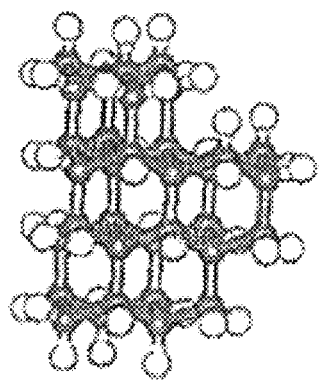
Figure 95:
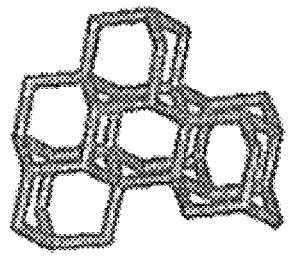
Figure 95:
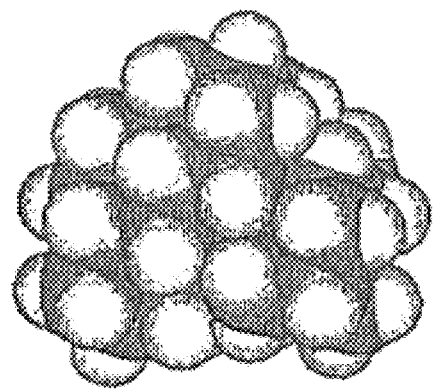
Figure 96:
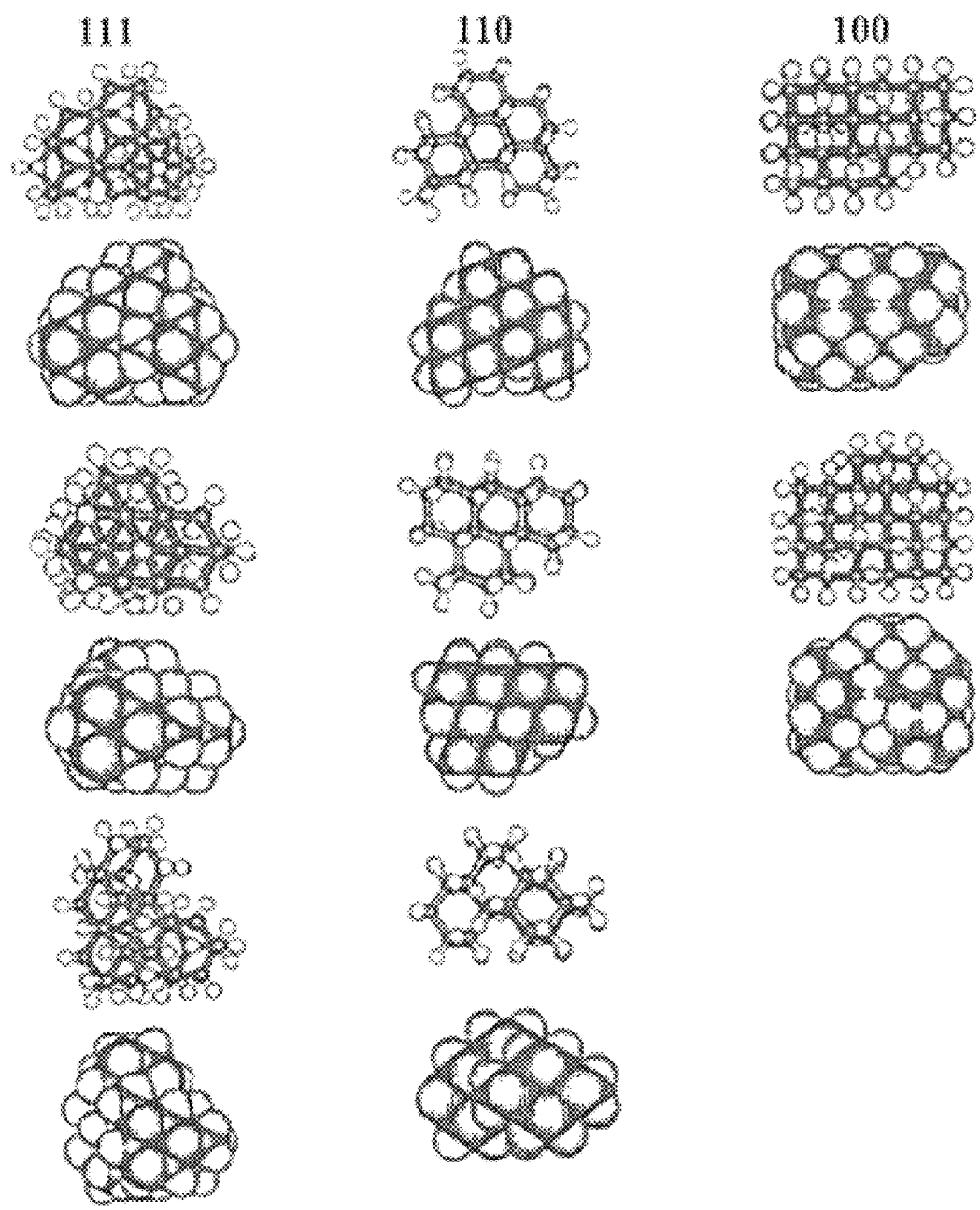
Figure 97:
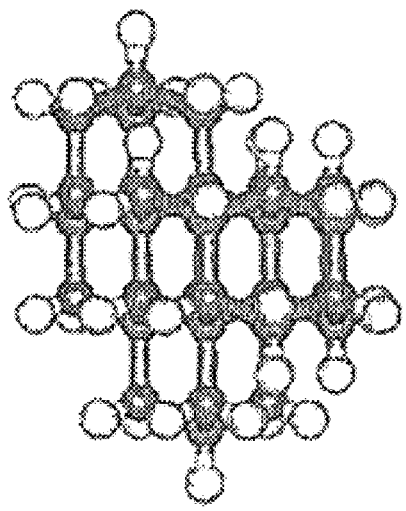
Figure 97:
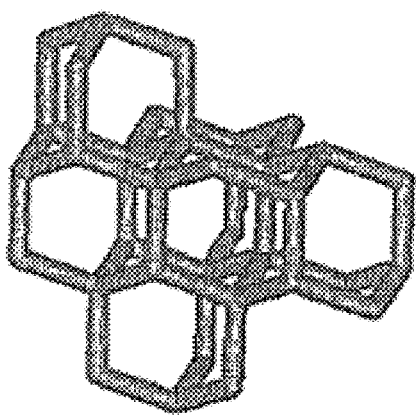
Figure 97:
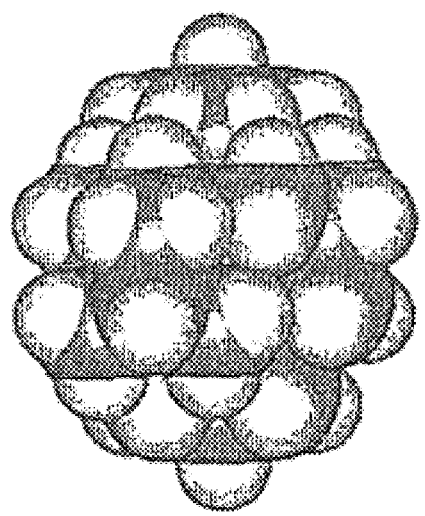
Figure 98:
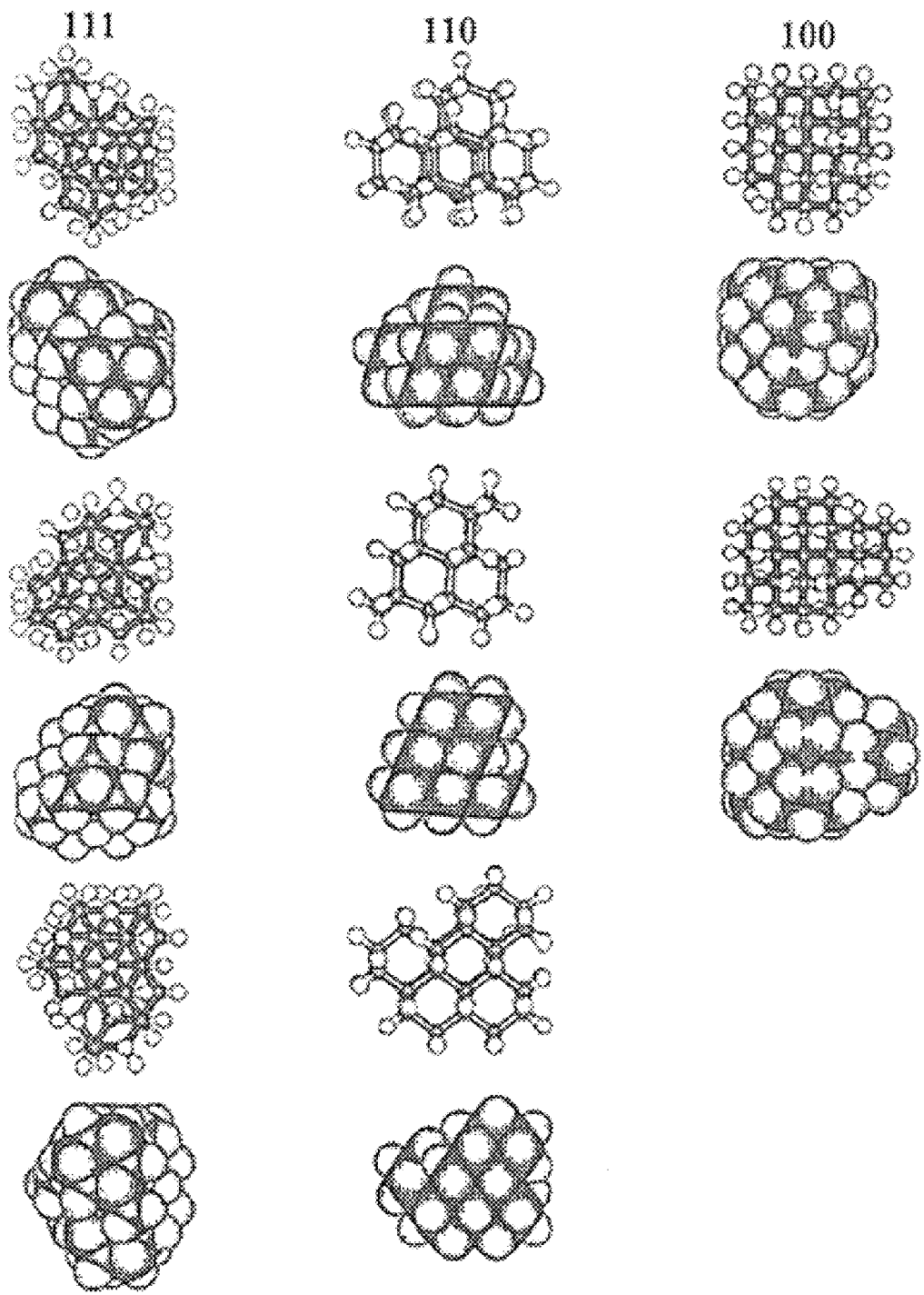
Figure 99:
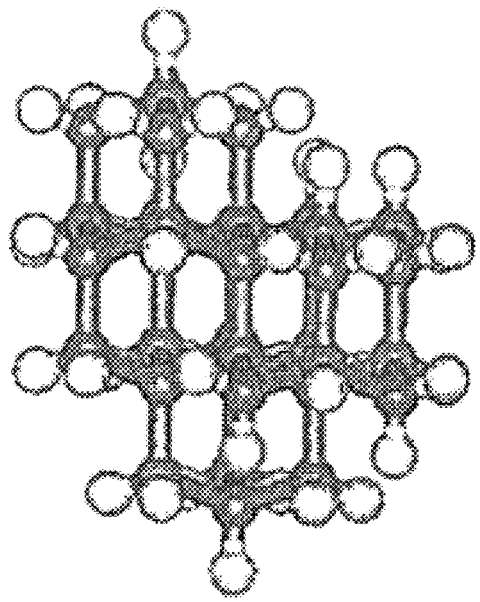
Figure 99:
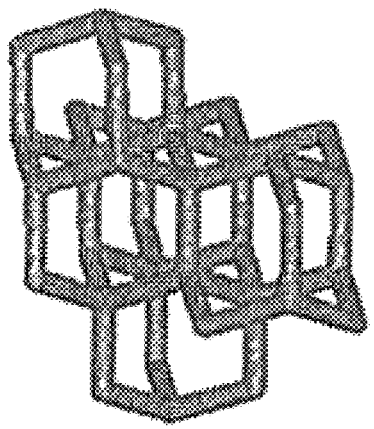
Figure 99:
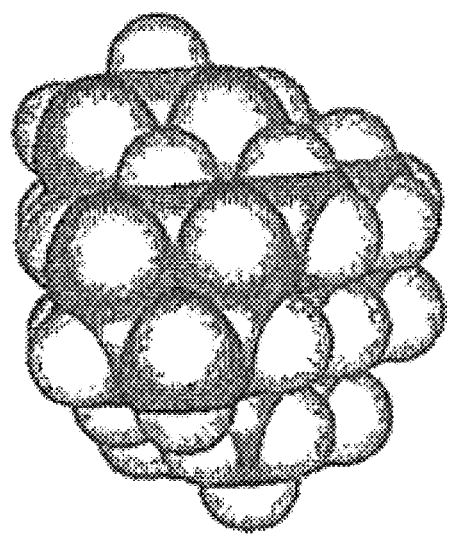
Figure 100:
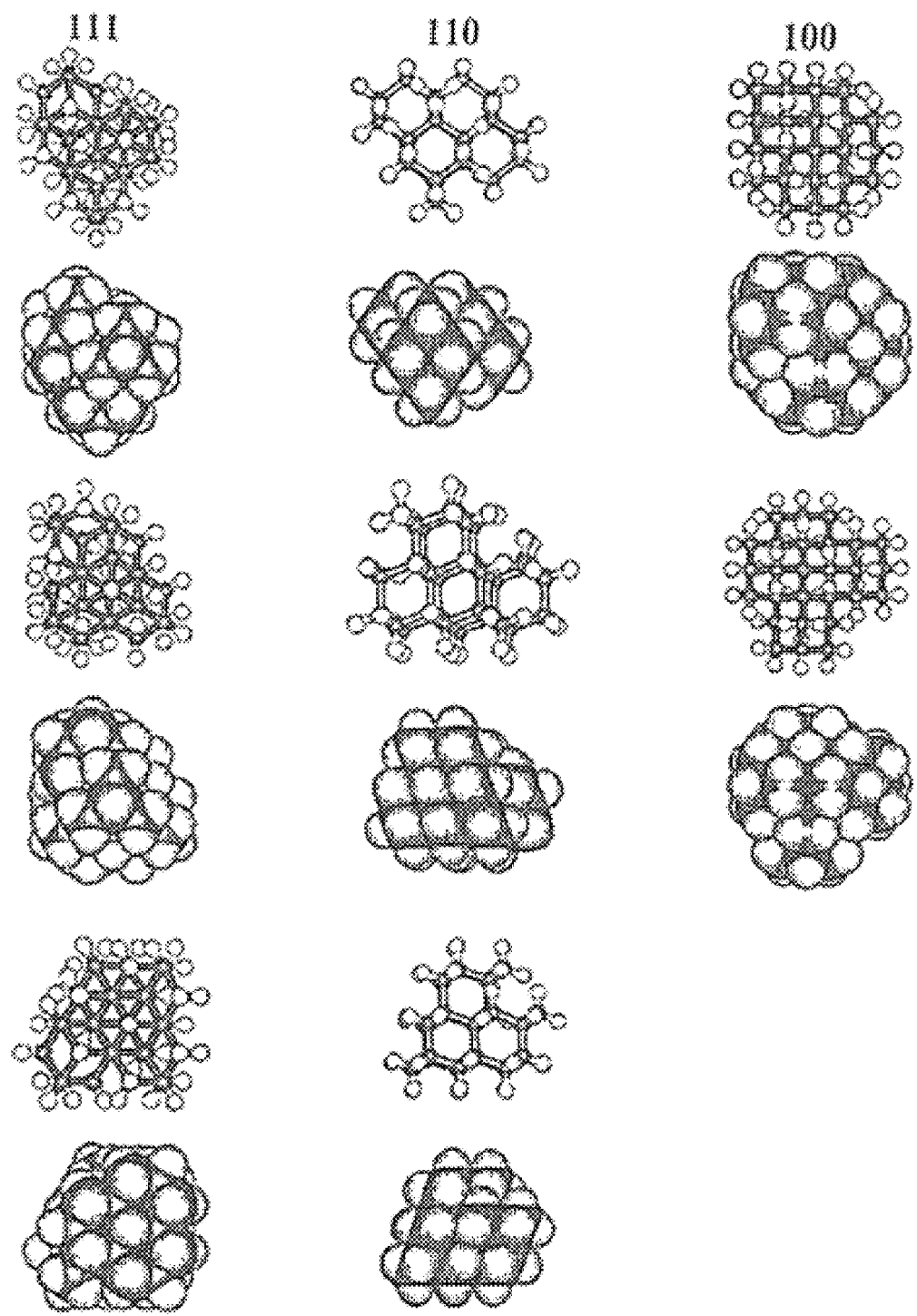
Figure 101:
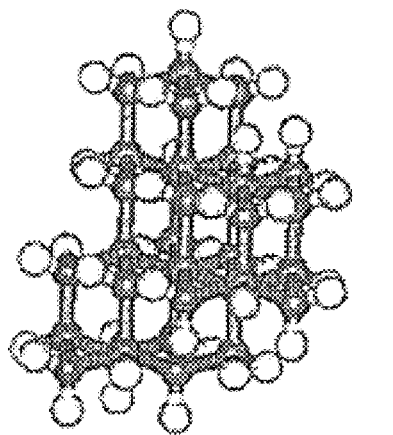
Figure 101:
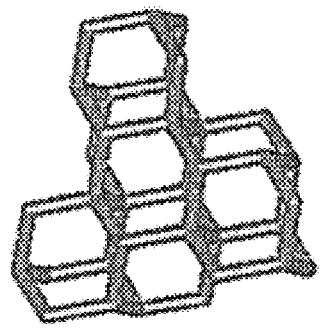
Figure 101:
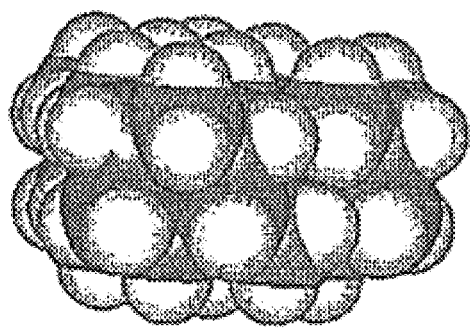
Figure 102:
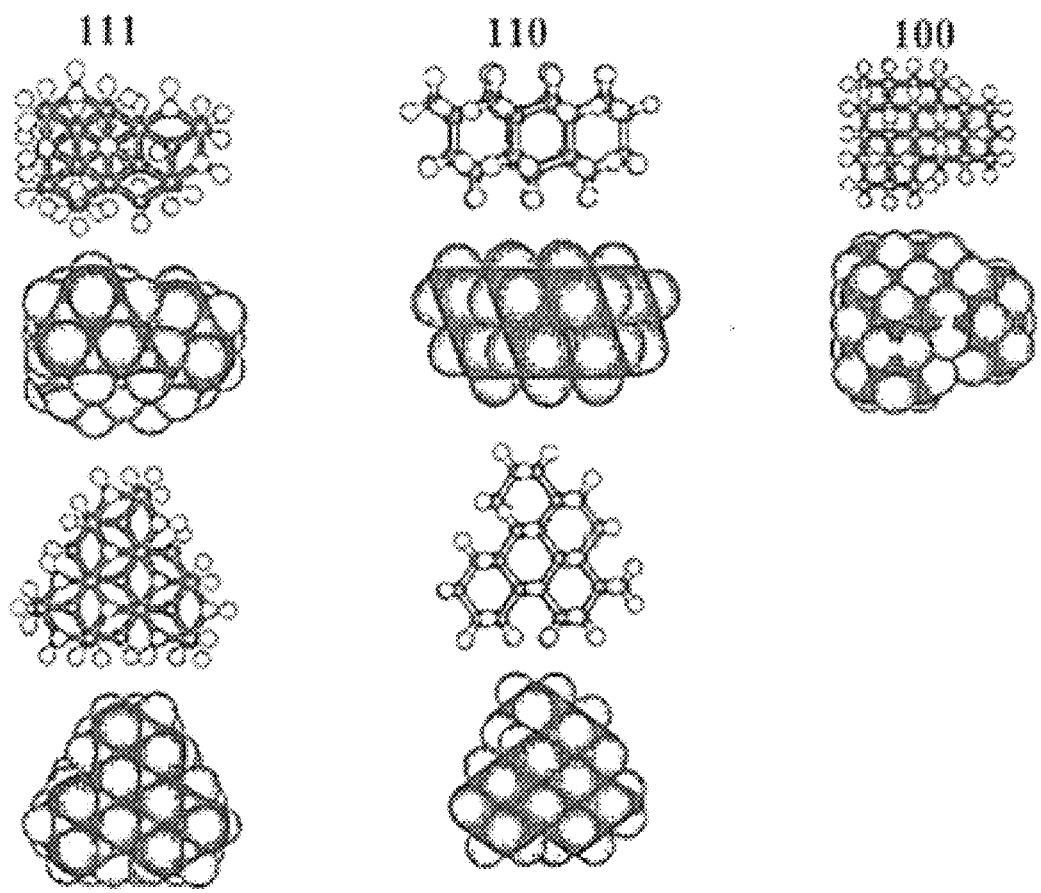
Figure 103:
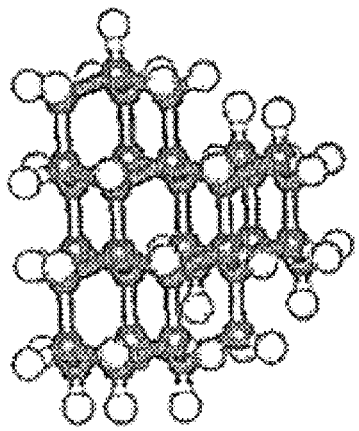
Figure 103:
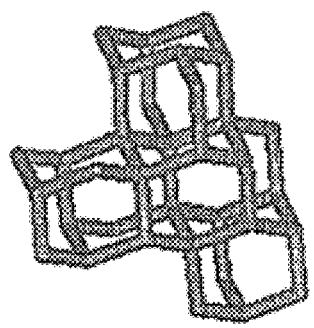
Figure 103:
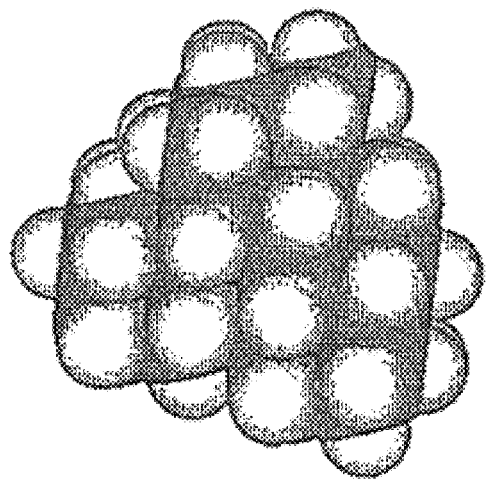
Figure 104:
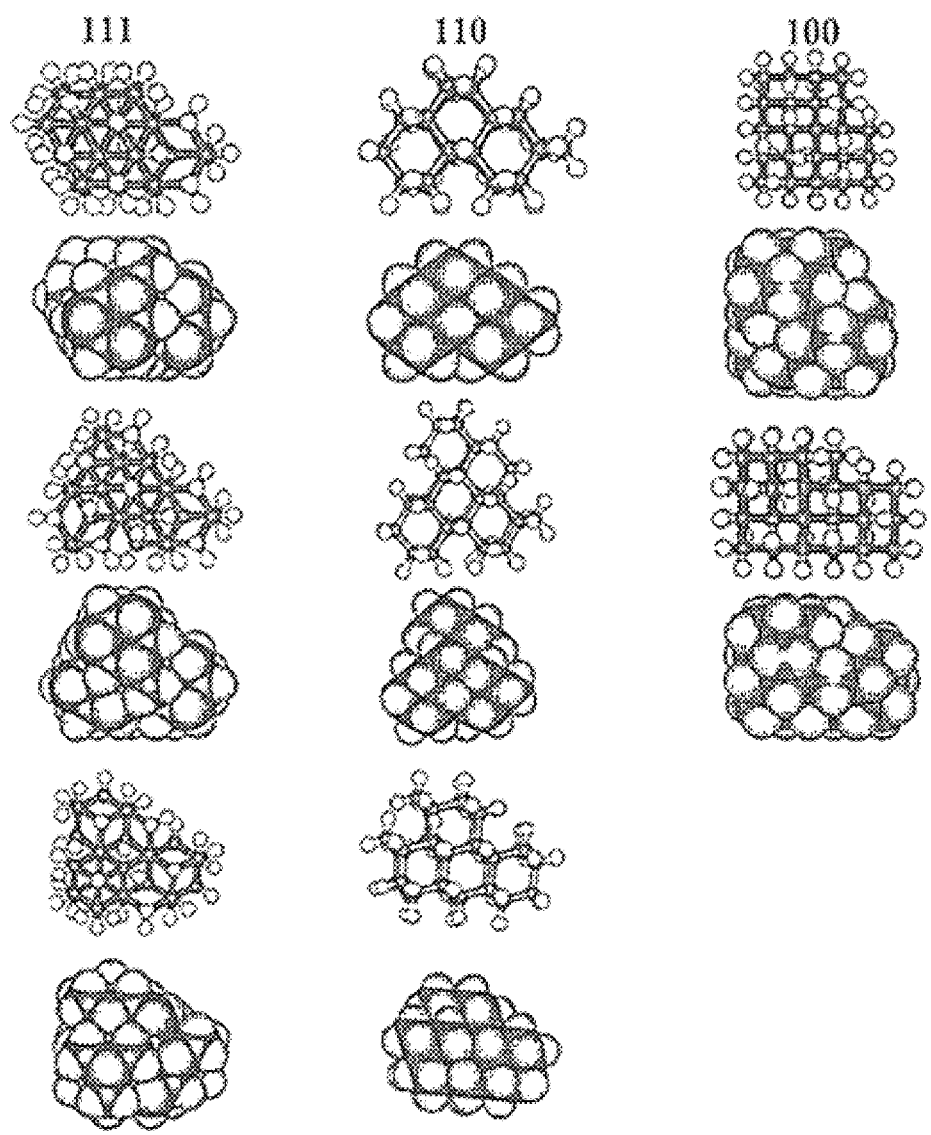
Figure 105:
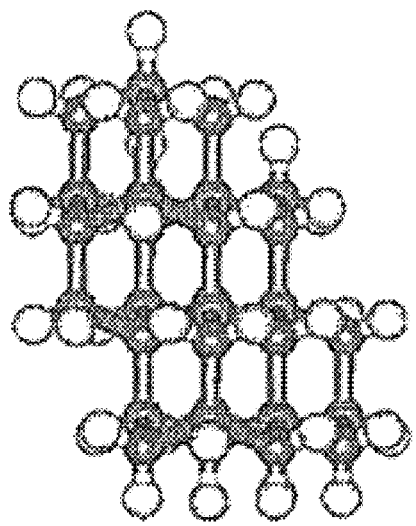
Figure 105:
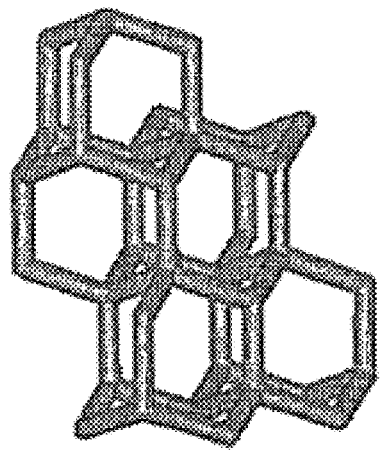
Figure 105:
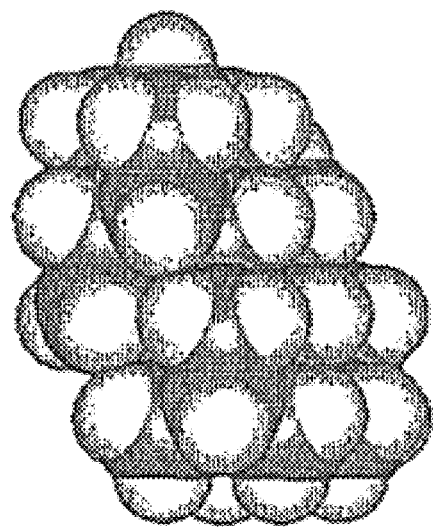
Figure 106:
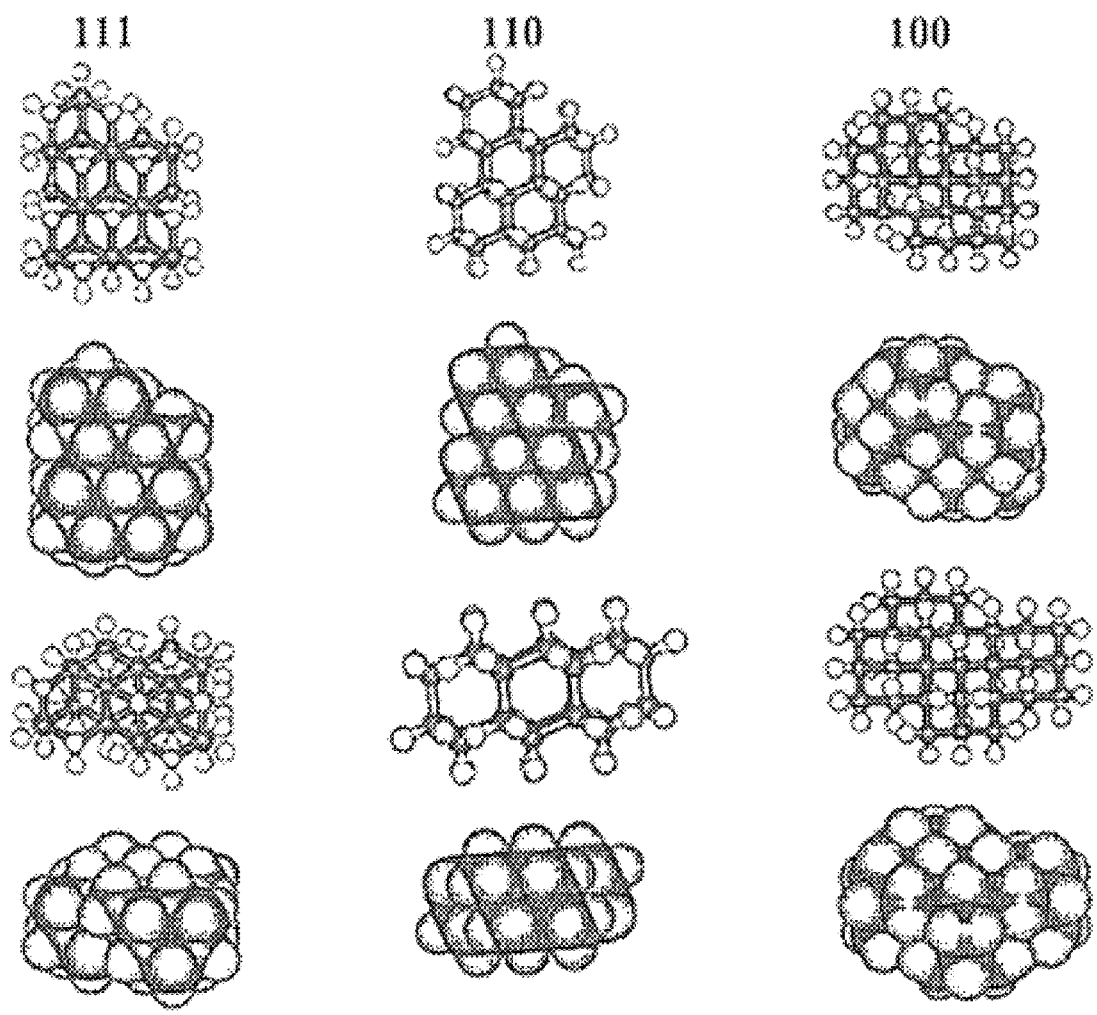
Figure 107:
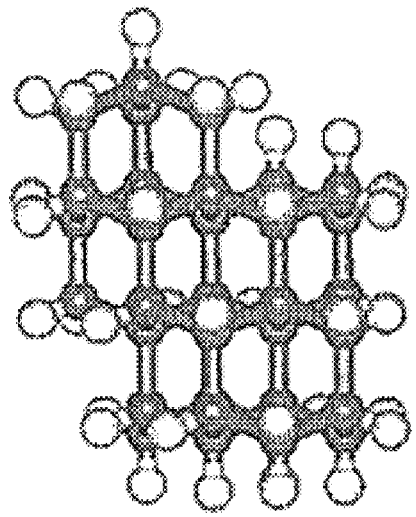
Figure 107:
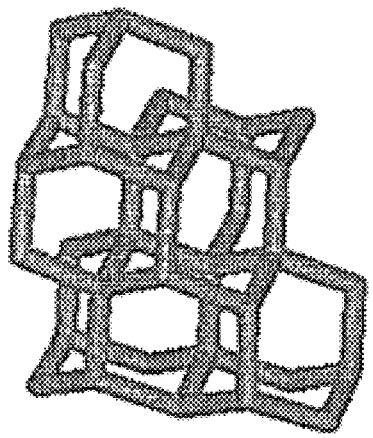
Figure 107:
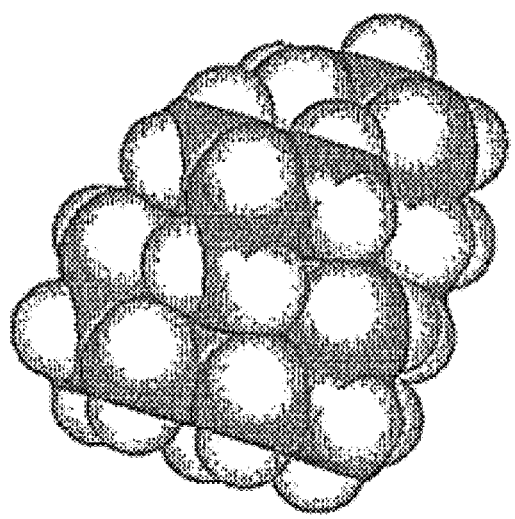
Figure 108:
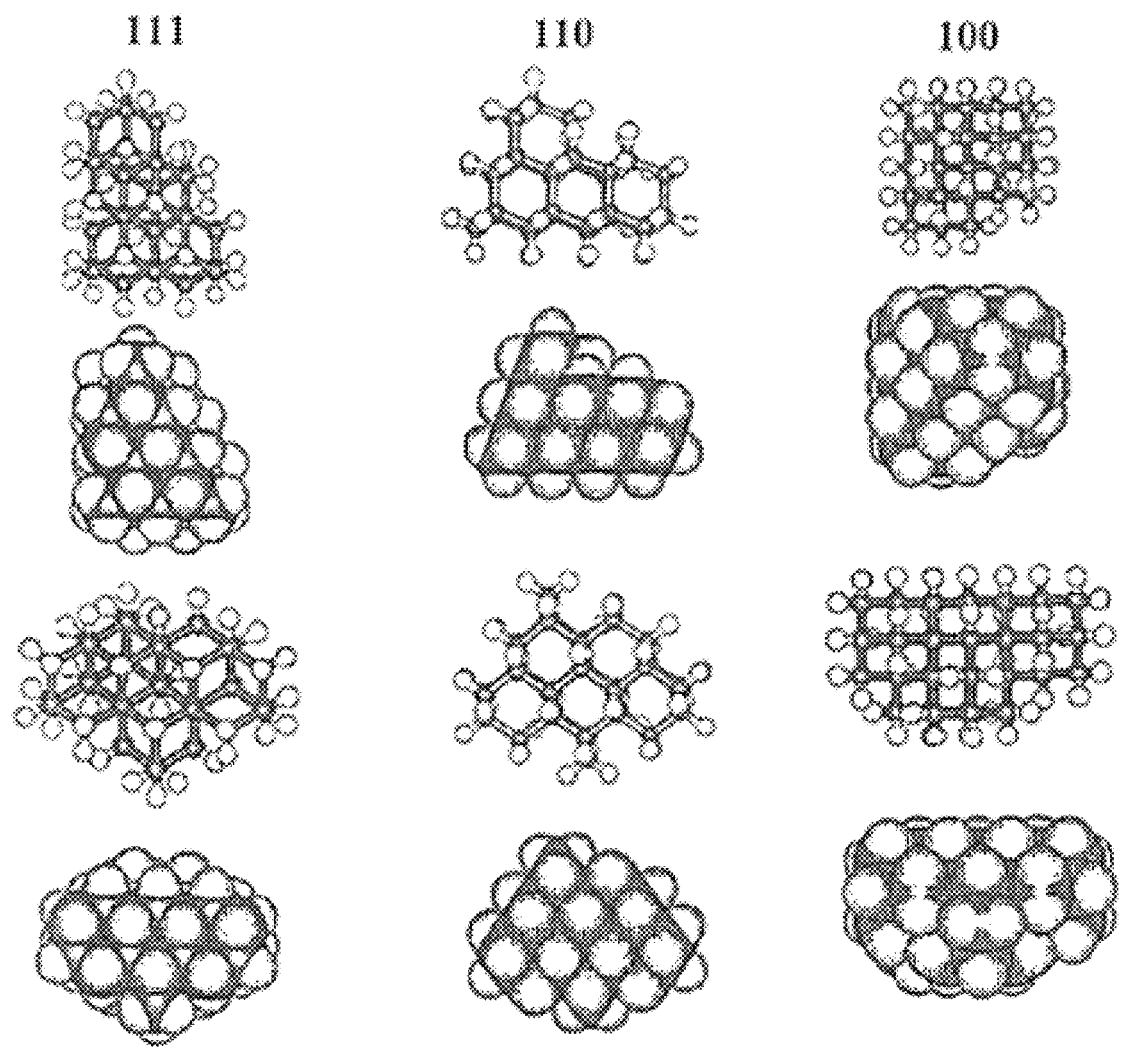
Figure 109:
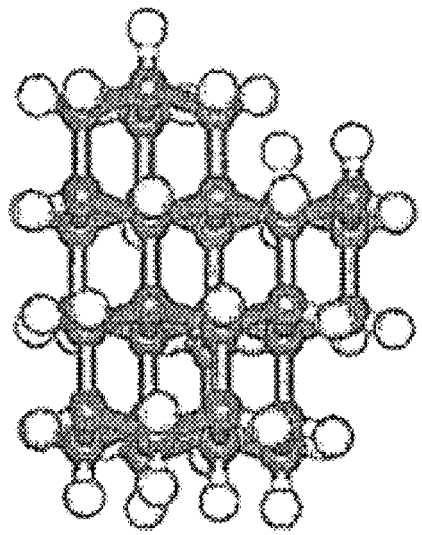
Figure 109:
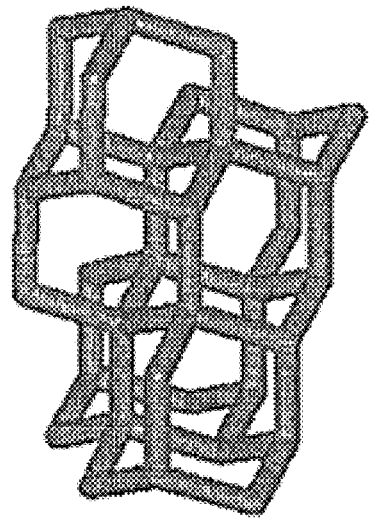
Figure 109:
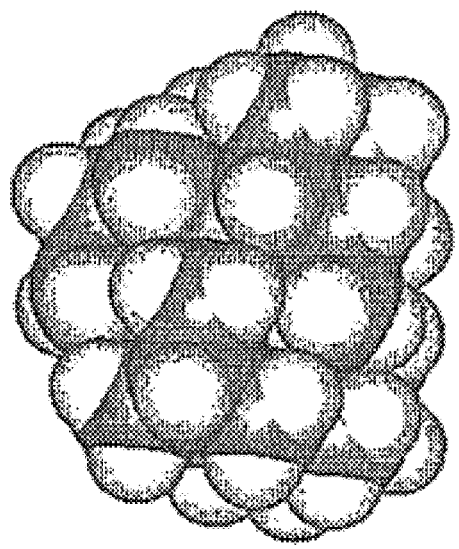
Figure 110:
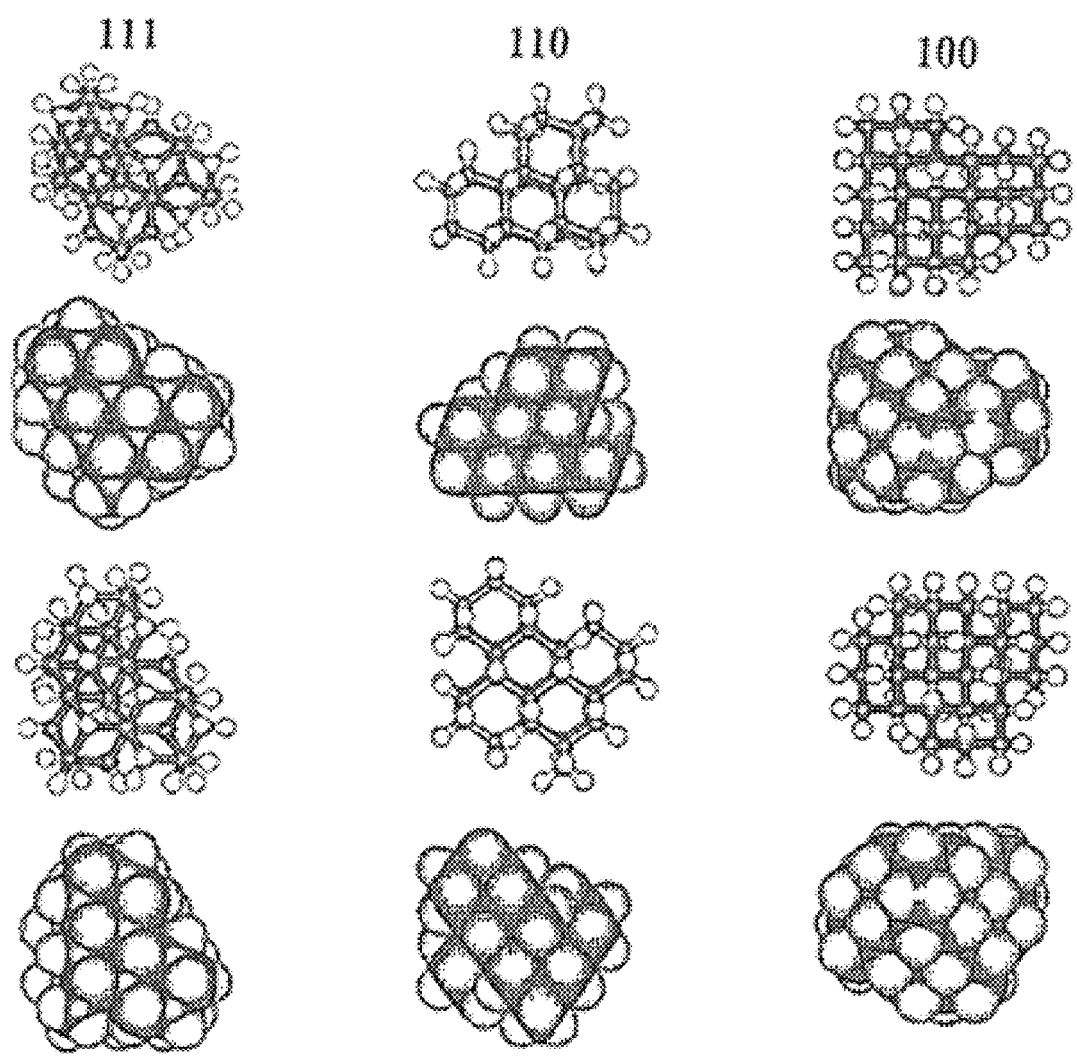
Figure 111:
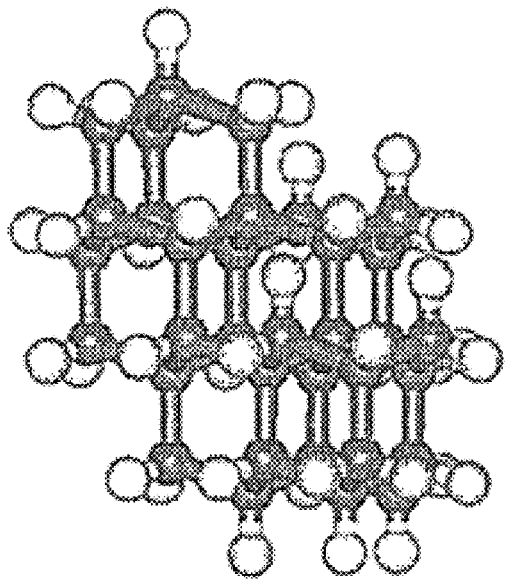
Figure 111:
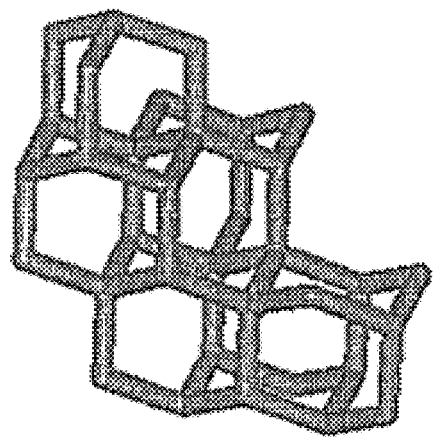
Figure 111:
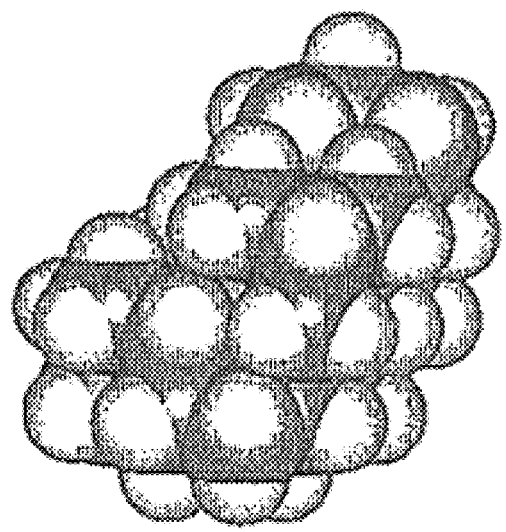
Figure 112:
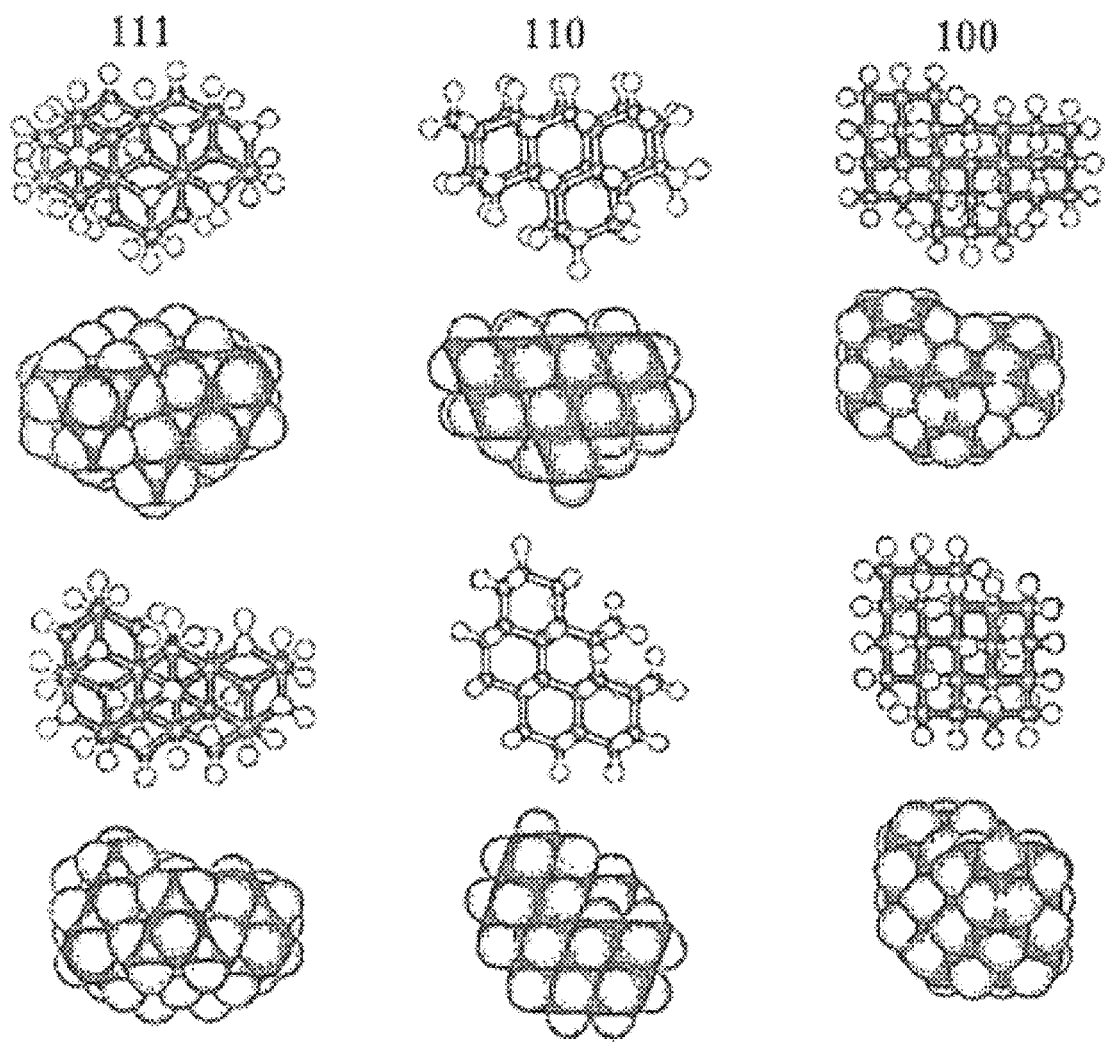
Figure 113:
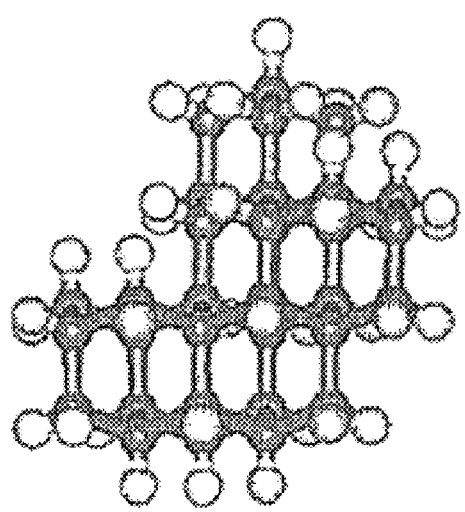
Figure 113:
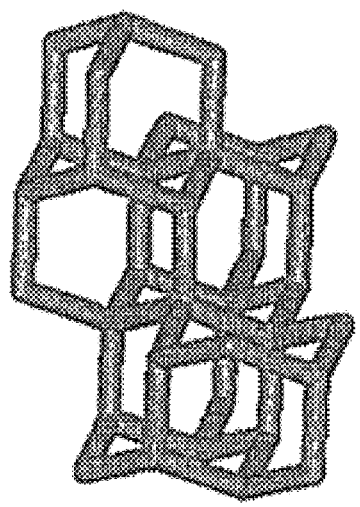
Figure 113:
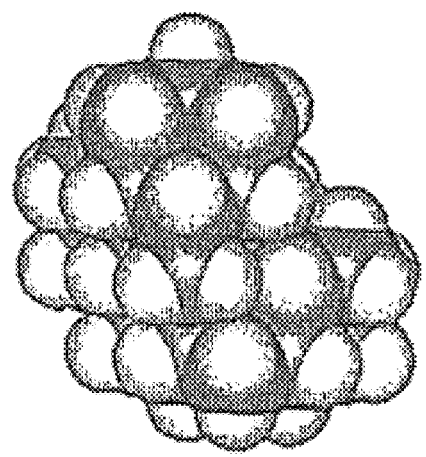
Figure 114:
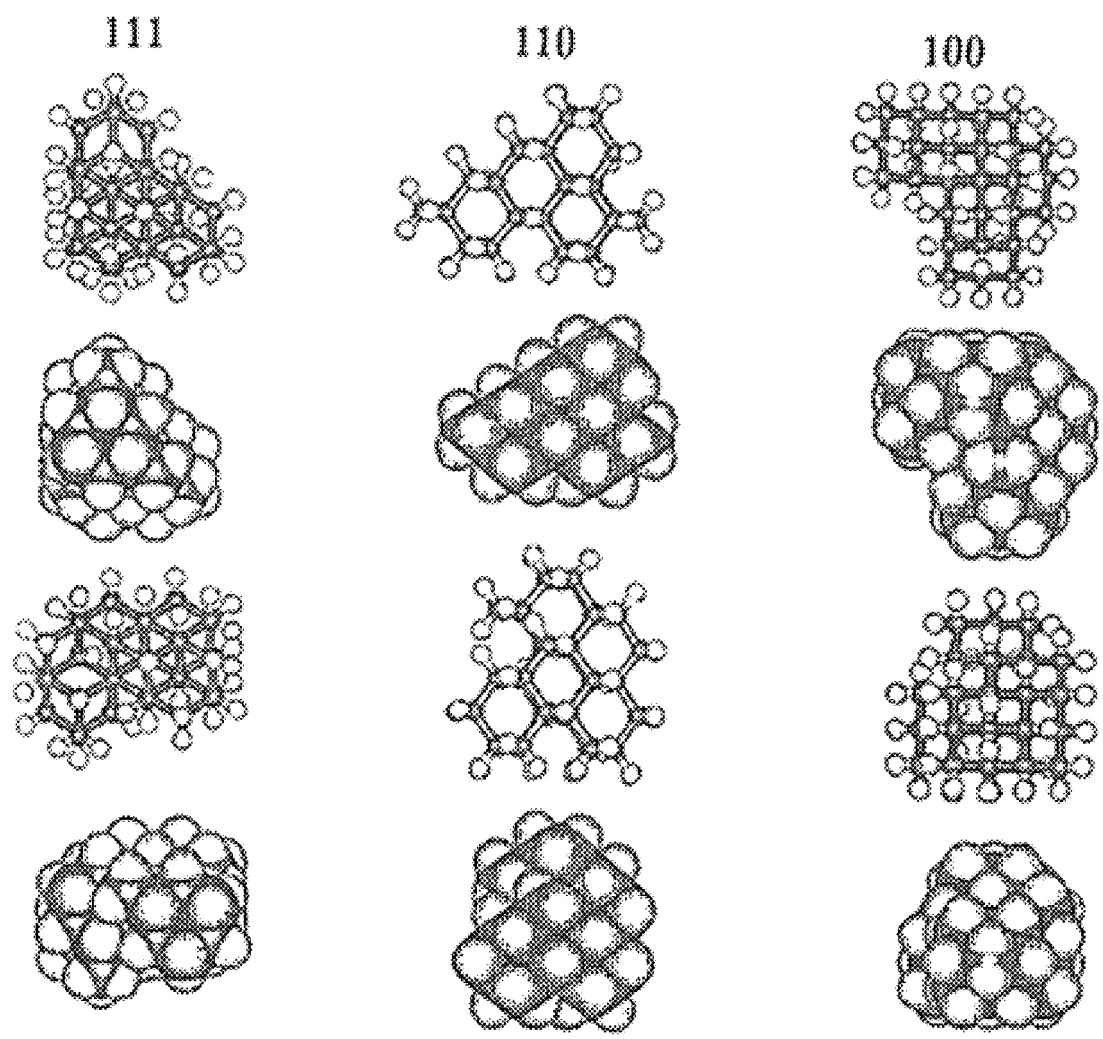
Figure 115:
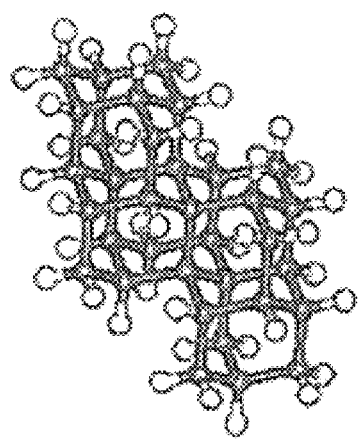
Figure 115:
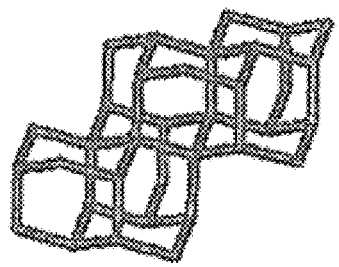
Figure 115:
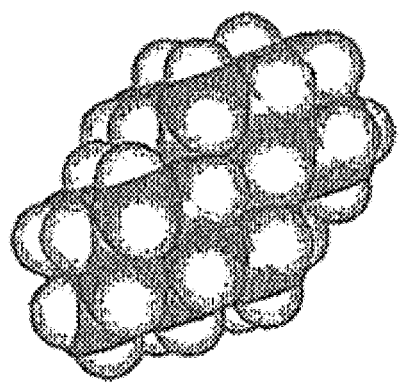
Figure 116:
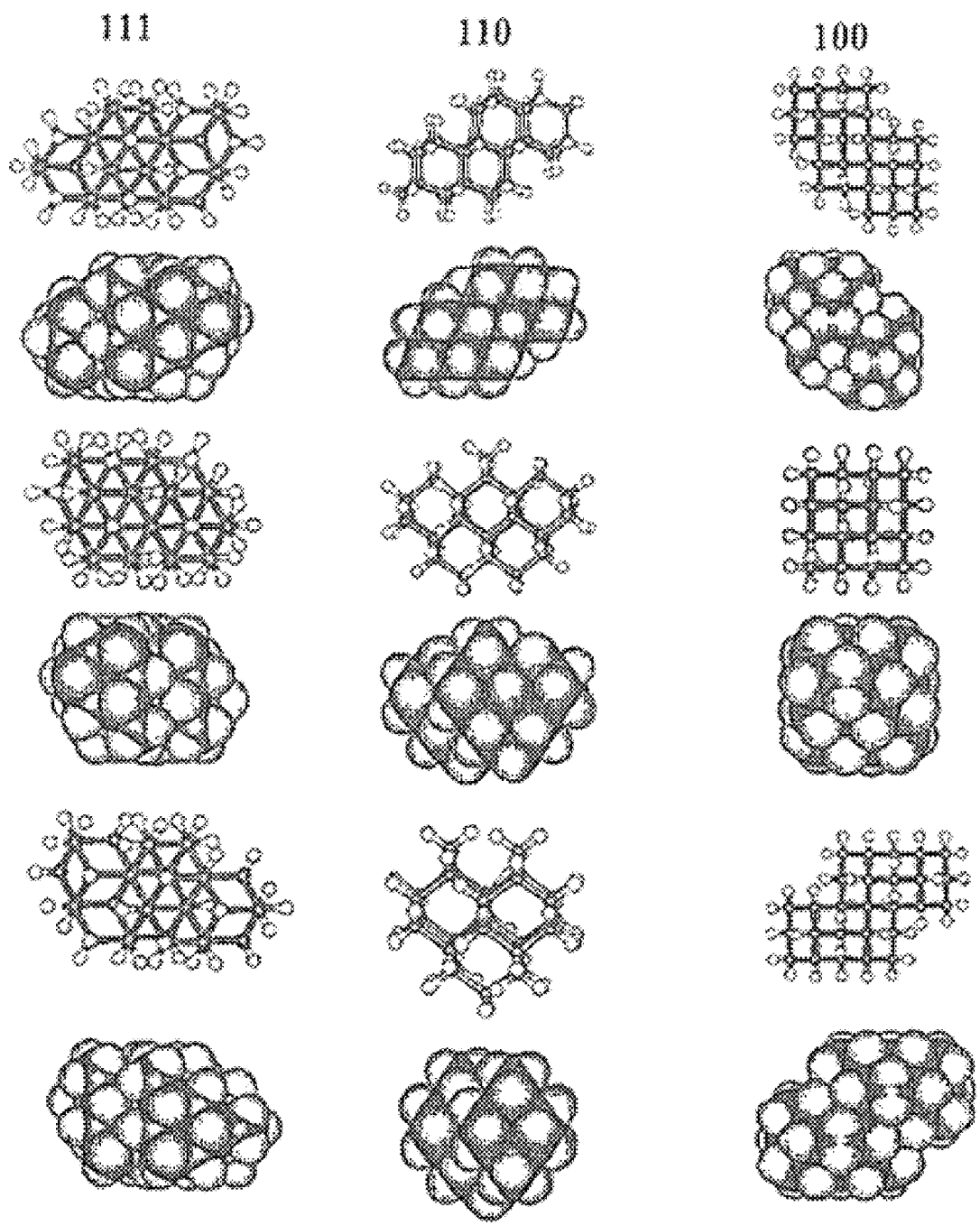
Figure 117:
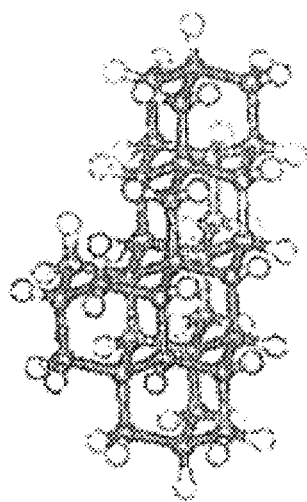
Figure 117:
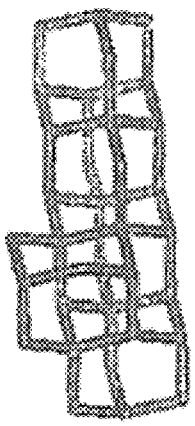
Figure 117:
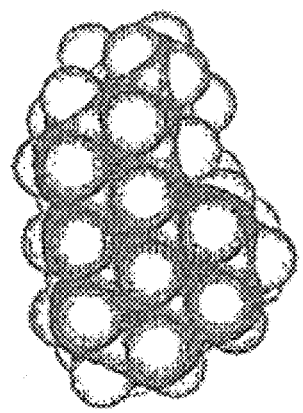
Figure 118:
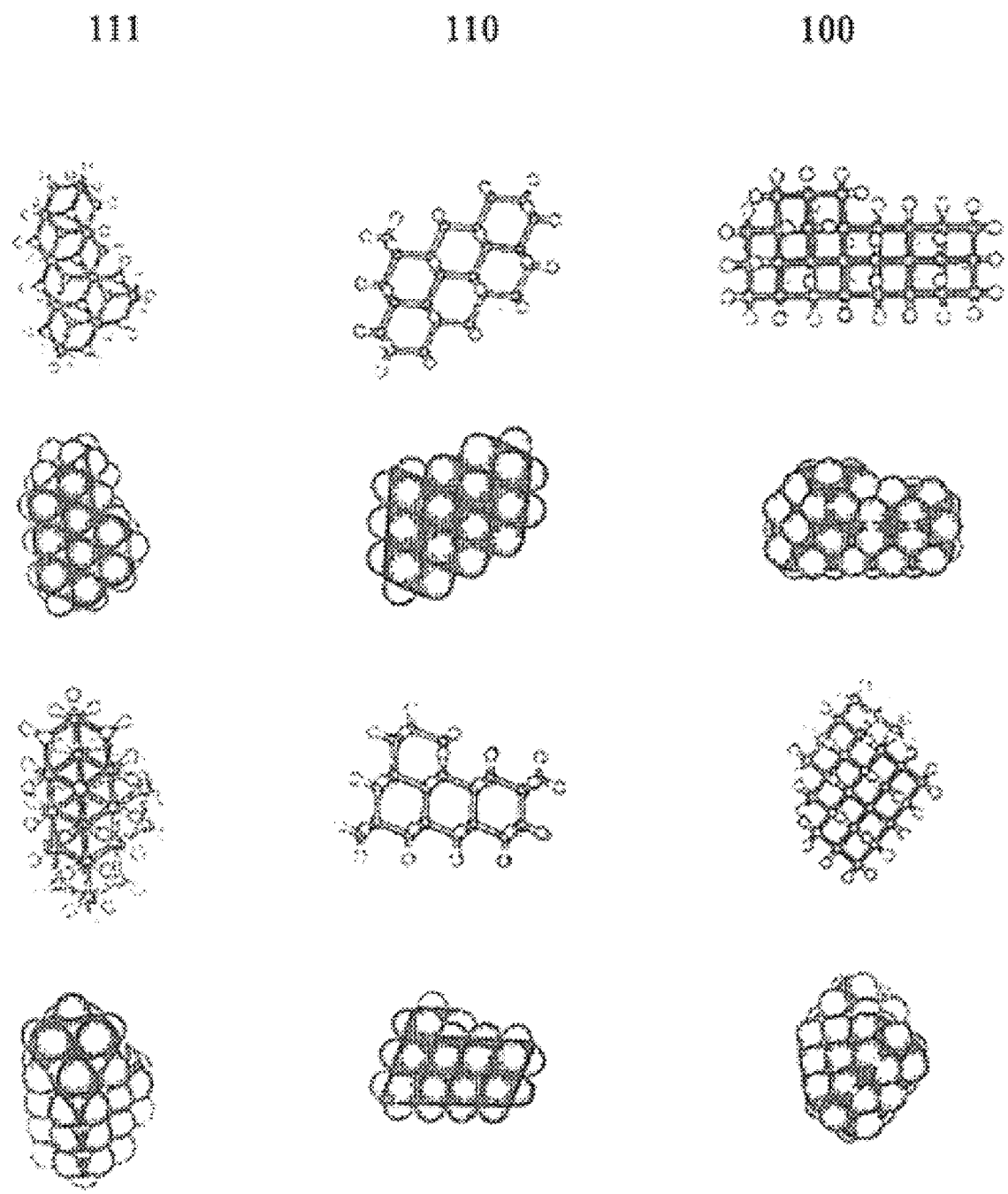
Figure 119:
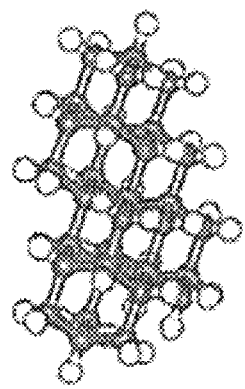
Figure 119:
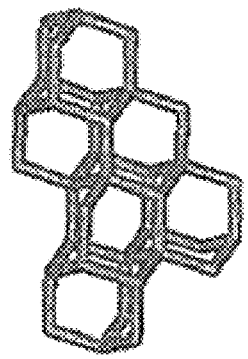
Figure 119:
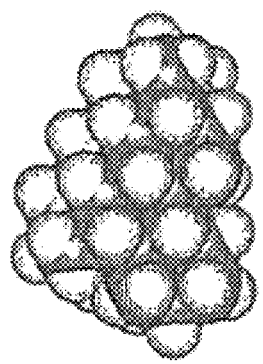
Figure 120:
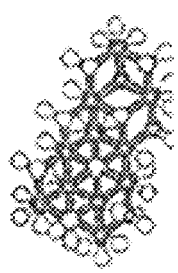
Figure 120:
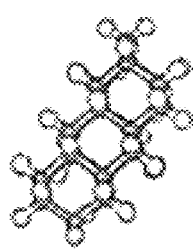
Figure 120:
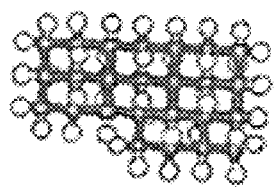
Figure 120:
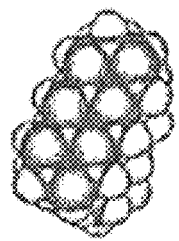
Figure 120:
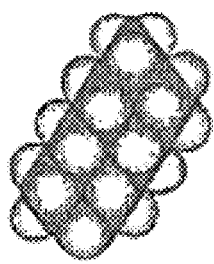
Figure 120:
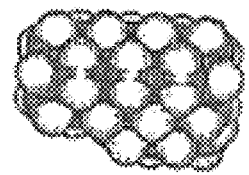

FIGS. 25 through 120, illustrate the size and structure with views into various diamond crystal lattice planes for thirty-nine heptamantanes.

Example 5

Isolation of Substituted Heptamantanes

Figure 24:
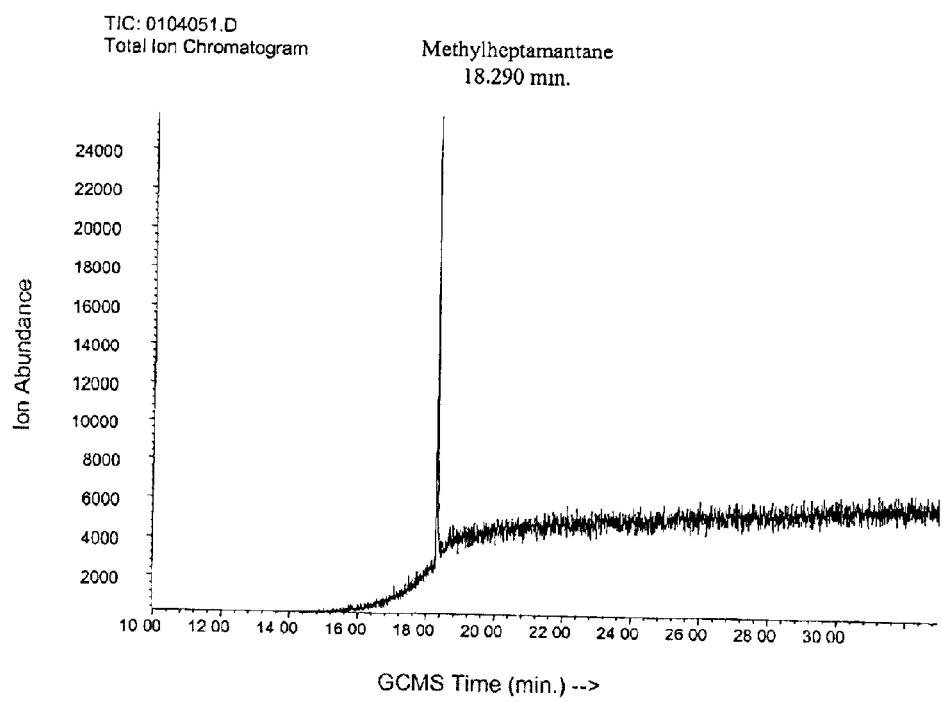
FIGS. 24A, B) illustrates GC/MS total ion chromatogram (TIC) and mass spectrum of a methylheptamantane component (mol. wt. 408) isolated in high purity in ODS HPLC fraction # 51.
Figure 24:
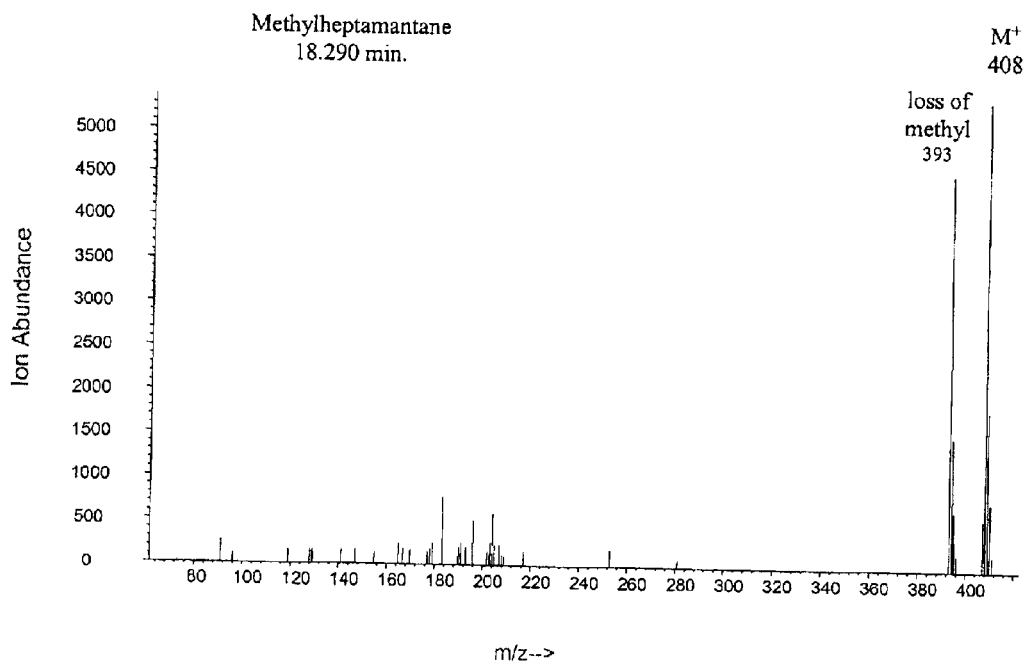

Substituted heptamantanes including alkylheptamantanes also are present in Feedstock A and B. These natural substituted heptamantanes have uses similar to the unsubstituted heptamantanes and can be de-alkylated to yield the corresponding unsubstituted heptamantanes. Accordingly, methods for the isolation of individual substituted heptamantanes were devised and exemplified by the isolation of alkyl substituted derivatives. Alkylheptamantanes can be purified by removal of nondiamondoid impurities from feedstocks using pyrolysis as shown in Example 2. Certain alkylheptamantanes survive pyrolysis processing, as do the heptamantane components previously identified. Substituted heptamantanes including alkylheptamantanes can be isolated in high purity using a single HPLC separation as exemplified by FIGS. 24A/B, and demonstrated for the heptamantanes in Example 3. FIGS. 24(A/B) shows an ODS HPLC separation (FIG. 15) of the saturated hydrocarbon fraction from Feedstock B, distillation fraction 7 pyrolysis contains a methylated heptamantane in high purity. Monomethylated heptamantanes have a molecular weight of 408 (yielding a mass spectrometric molecular ion of m/z 408, and show a mass spectrometric loss of the methyl group giving the m/z 393 mass spectrometric fragment ion indicative of a heptamantane moiety (FIG. 24B). Also, where more than one alkylheptamantane is present in an ODS or Hypercarb HPLC fraction, an additional HPLC separation of that fraction on an alternative HPLC system can yield high purity alkyl heptamantanes as demonstrated for the heptamantanes in Example 3. Alkylheptamantanes can also be isolated using additional chromatographic techniques, thermal diffusion techniques, zone refining, progressive recrystalization and size separation techniques.

What is claimed is:

1. A composition comprising diamondoids wherein at least about 25 weight percent of the diamondoids are one or more heptamantane components.

2. A composition of claim 1 wherein from 50 to 100 weight percent of the diamondoids are one or more heptamantane components.

3. A composition of claim 1 wherein from 70 to 100 weight percent of the diamondoids are one or more heptamantane components.

4. A composition of claim 1 wherein from 95 to 100 weight percent of the diamondoids are one or more heptamantane components.

5. A composition of claim 1 wherein from 99 to 100 weight percent of the diamondoids are one or more heptamantane components.

6. The composition of any of claims 1–5, wherein the one or more heptamantane components are a single heptamantane component.

7. The composition of any of claims 1–5 wherein the one or more heptamantane components are isolated optical isomers.

8. The composition of any of claims 1–5, wherein the one or more heptamantane components are isomeric heptamantane components.

9. The composition of any of claims 1–5, wherein the one or more heptamantane components are one or more isomeric heptamantane components represented by the formula $C_{30}H_{34}$.

10. The composition of any of claims 1–5, wherein the one or more heptamantane components are one or more isomeric heptamantane components represented by the formula $C_{32}H_{36}$.

11. The composition of any of claims 1–5, wherein the one or more heptamantane components are one or more isomeric heptamantane components represented by the formula $C_{33}H_{38}$.

12. The composition of any of claims 1–5, wherein the one or more heptamantane components are one or more isomeric heptamantane components represented by the formula $C_{34}H_{40}$.

13. The composition of any of claims 1–5 wherein the heptamantane components comprise unsubstituted heptamantane components.

14. The composition of any of claims 1–5 wherein the heptamantane components comprise substituted heptamantane components having from 1 to 10 alkyl substituents.

15. A composition comprising at least about 10% by weight of one or more heptamantane components.

16. The composition of claim 15 containing from 50 to 100% by weight of one or more heptamantane components.

17. The composition of claim 15 containing from 70 to 100% by weight of one or more heptamantane components.

18. The composition of claim 15 containing from 95 to 100% by weight of one or more heptamantane components.

19. The composition of claim 15 containing from 99 to 100% by weight of one or more heptamantane components.

20. The composition of claims 15–19 wherein the one or more heptamantane components are a single heptamantane component.

21. The composition of claim 1, wherein the one or more heptamantane components have a molecular weight of 394.

22. The composition of claim 1, wherein the one or more heptamantane components include [121321] heptamantane.

23. The composition of claim 1, wherein the one or more heptamantane components include [123124] heptamantane.

24. The composition of claim 1, wherein the one or more heptamantane components are in crystalline form.

25. A process for recovering a composition enriched in one or more heptamantane components which process comprises:
   a. selecting a feedstock comprising recoverable amounts of heptamantane components and nonheptamantane components;
   b. removing from the feedstock a sufficient amount of nonheptamantane components having boiling points less than the lowest boiling point heptamantane component under conditions to form a treated feedstock enriched in heptamantane components which can be recovered;
   c. recovering a composition enriched in one or more heptamantane components from said treated feedstock formed in b) above with one or more additional separation techniques selected from the group consisting of chromatographic techniques, thermal diffusion techniques, zone refining, progressive recrystallization and size separation techniques.

26. A process for recovering a composition enriched in heptamantane components which process comprises:
   a. selecting a feedstock comprising recoverable amounts of heptamantane components and nonheptamantane components including nondiamondoid components;
   b. removing from the feedstock a sufficient amount of nonheptamantane components having a boiling point less than the lowest boiling point heptamantane component under conditions to form a treated feedstock enriched in heptamantane components which can be recovered;
   c. thermally degrading said treated feedstock to pyrolyze at least a sufficient amount of nondiamondoid components therefrom under conditions to form a thermally treated feedstock retaining recoverable amounts of heptamantane;
   d. recovering a composition enriched in one or more heptamantane components from said thermally treated feedstock formed in c) above with one or more additional separation techniques selected from the group consisting of chromatographic techniques, thermal diffusion techniques, zone refining, progressive recrystallization and size separation techniques.

27. A process for recovering a composition enriched in one or more heptamantane components which process comprises:
   a. selecting a feedstock comprising recoverable amounts of heptamantane components and nonheptamantane components including nondiamondoid components;
   b. thermally degrading said feedstock to pyrolyze at least a sufficient amount of nondiamondoid components therefrom under conditions to provide a thermally treated feedstock retaining recoverable amounts of heptamantane;
   c. removing from the thermally treated feedstock a sufficient amount of nonheptamantane components having a boiling point less than the lowest boiling point of heptamantane component under conditions to form a treated feedstock enriched in heptamantanes components which can be recovered;
   d. recovering a composition enriched in one or more heptamantane components from said treated feedstock recovered in c) above with one or more additional separation techniques selected from the group consisting of chromatographic techniques, thermal diffusion techniques, zone refining, progressive recrystallization and size separation techniques.

28. A process for recovering a composition enriched in one or more heptamantane components which process comprises:
   a. selecting a feedstock comprising recoverable amounts of heptamantane components and nonheptamantane components;
   b. fractionating the feedstock to form one or more cuts enriched in materials having boiling points in the range of from just below the boiling point of the lowest boiling heptamantane component to just above the boiling point of the highest boiling heptamantane component;
   c. recovering a composition enriched in one or more heptamantane components from said one or more cuts formed in b) above with one or more additional separation techniques selected from the group consisting of chromatographic techniques, thermal diffusion techniques, zone refining, progressive recrystallization and size separation techniques.

29. A process for recovering a composition enriched in one or more heptamantane components which process comprises:
   a. selecting a feedstock comprising recoverable amounts of heptamantane components and nonheptamantane components including nondiamondoid components;
   b. fractionating the feedstock to form one or more cuts enriched in materials having boiling points in the range of from just below the boiling point of the lowest boiling heptamantane component to just above the boiling point of the highest boiling heptamantane component;
   c. thermally degrading one or more cuts said to pyrolyze at least a sufficient amount of nondiamondoid components therefrom under conditions to form one or more thermally treated cuts retaining recoverable amounts of heptamantane;
   d. recovering a composition comprising one or more heptamantane components from one or more said thermally treated cuts formed in c) above with one or more additional separation techniques selected from the group consisting of chromatographic techniques, thermal diffusion techniques, zone refining, progressive recrystallization and size separation techniques.

30. A process for recovering a composition enriched in one or more heptamantane components which process comprises:
   a. selecting a feedstock comprising recoverable amounts of heptamantane components and nonheptamantane compounds including nondiamondoid components;
   b. thermally degrading said feedstock to pyrolyze at least a sufficient amount of nondiamondoid components therefrom under conditions to provide a thermally treated feedstock retaining recoverable amounts of heptamantane;
   c. fractionating the thermally treated feedstock to form one or more cuts enriched in materials having boiling points in the range of from just below the boiling point of the lowest boiling heptamantane component to just above the boiling point of the highest boiling heptamantane component;
   d. recovering a composition enriched in one or more heptamantane components from one or more cuts formed c) above with one or more additional separation techniques selected from the group consisting of chromatographic techniques, thermal diffusion techniques, zone refining, progressive recrystallization and size separation techniques.

31. The process according to any of claims 28–30 wherein said boiling point range is a range having atmospheric equivalents of between about 350 to about 600° C.

32. The process according to any of claims 25–30 wherein said separation technique is a chromatographic technique.

33. The process according to claim 32 wherein said chromatographic technique is selected from the group consisting of liquid chromatography, preparative gas chromatography and high performance liquid chromatography.

34. The process according to claim 32 wherein said additional separation technique is high performance liquid chromatography comprising one or more high performance liquid chromatography columns.

35. The process according to claim 34 wherein the high performance liquid chromatography columns are selected to have a different specificity to the heptamantane components.

36. A product prepared by the process of claim 25.
37. A product prepared by the process of claim 26.
38. A product prepared by the process of claim 27.
39. A product prepared by the process of claim 28.
40. A product prepared by the process of claim 29.
41. A product prepared by the process of claim 30.

* * * * *